United States Patent
Minn et al.

(10) Patent No.: US 8,329,717 B2
(45) Date of Patent: Dec. 11, 2012

(54) PYRIMIDINE DERIVATIVES AND THEIR USE FOR CONTROLLING UNDESIRED PLANT GROWTH

(75) Inventors: Klemens Minn, Hattersheim (DE); Hansjörg Dietrich, Liederbach am Taunus (DE); Jan Dittgen, Frankfurt (DE); Dieter Feucht, Eschborn (DE); Isolde Häuser-Hahn, Leverkusen (DE); Christopher Hugh Rosinger, Hofheim (DE)

(73) Assignee: Bayer Cropscience AG, Monheim (DE)

( * ) Notice: Subject to any disclaimer, the term of this patent is extended or adjusted under 35 U.S.C. 154(b) by 107 days.

(21) Appl. No.: 12/646,070

(22) Filed: Dec. 23, 2009

(65) Prior Publication Data
US 2010/0167934 A1    Jul. 1, 2010

(30) Foreign Application Priority Data

Dec. 30, 2008   (EP) .................................. 08022523

(51) Int. Cl.
*A01N 43/54* (2006.01)
*A61K 31/505* (2006.01)
(52) U.S. Cl. ......... 514/275; 544/323; 544/324; 544/325
(58) Field of Classification Search .................. 544/323, 544/324, 325
See application file for complete search history.

(56) References Cited

U.S. PATENT DOCUMENTS

| | | | |
|---|---|---|---|
| 4,639,266 A | 1/1987 | Heubach et al. | |
| 4,785,105 A | 11/1988 | Hubele | |
| 4,881,966 A | 11/1989 | Nyffeler et al. | |
| 4,891,057 A | 1/1990 | Sohn et al. | |
| 4,902,340 A | 2/1990 | Hubele | |
| 5,013,659 A | 5/1991 | Bedbrook et al. | |
| 5,254,555 A * | 10/1993 | Stemp et al. | 514/256 |
| 5,280,009 A | 1/1994 | Hamprecht et al. | |
| 5,314,863 A | 5/1994 | Loeher et al. | |
| 2004/0157739 A1 | 8/2004 | Ahrens et al. | |
| 2010/0167935 A1 * | 7/2010 | Minn et al. | 504/239 |

FOREIGN PATENT DOCUMENTS

| | | |
|---|---|---|
| EP | 0 086 750 A2 | 2/1983 |
| EP | 0 094 349 A2 | 5/1983 |
| EP | 0131624 | 1/1985 |
| EP | 0142924 | 5/1985 |
| EP | 0 174 562 A2 | 8/1985 |
| EP | 0 191 736 A2 | 2/1986 |
| EP | 0193259 | 9/1986 |
| EP | 0221044 | 5/1987 |
| EP | 0 269 806 A1 | 9/1987 |
| EP | 0242236 | 10/1987 |
| EP | 0242246 | 10/1987 |
| EP | 0257993 | 3/1988 |
| EP | 0 268 554 A2 | 5/1988 |
| EP | 0309862 | 4/1989 |
| EP | 0 333 131 A1 | 9/1989 |
| EP | 0 346 620 A1 | 12/1989 |
| EP | 0 365 484 A1 | 4/1990 |
| EP | 0464461 | 1/1992 |
| EP | 0 492 366 A2 | 7/1992 |
| EP | 0 523 533 A1 | 8/1992 |
| EP | 523533 A1 * | 1/1993 |
| EP | 0 582 198 A2 | 2/1994 |
| JP | 60-87254 A | 5/1985 |
| WO | 91/07874 A1 | 6/1991 |
| WO | 91/08202 A1 | 6/1991 |
| WO | 91/13972 A1 | 9/1991 |
| WO | 91/19806 A | 12/1991 |
| WO | 92/00377 A1 | 1/1992 |
| WO | 92/11376 A1 | 7/1992 |
| WO | 92/14827 A1 | 9/1992 |
| WO | 95/07897 A1 | 3/1995 |
| WO | 97/45016 A1 | 12/1997 |
| WO | 98/13361 A1 | 4/1998 |
| WO | 98/27049 A1 | 6/1998 |
| WO | 98/38856 A1 | 9/1998 |
| WO | 99/00020 A1 | 1/1999 |

(Continued)

OTHER PUBLICATIONS

L. M. Abell et al. Target-Site Directed Herbicide Design in, Pest Control With Enhanced Environmental Safety 15-37 (ACS Symposium Series; American Chemical Society, S. Duke, et al. eds, 1993).*
W.T. Ruegg et al., Weed Research, 47(4), 271-275, 271 (2006).*
R.L Tominack, Clinical Toxicology, 38(2), 129-135, 131 (2000).*
K.Z.. Gadalla et al., Bulletin of the National Research Centre (Egypt) 18(2), 119-23 (1993).*
Braun et al., "The general mitochondrial processing peptidase from potato is an integral part of cytochrome c reductase of the respitory chain," The EMBO Journal, 11 (1992), 3219-3227.

(Continued)

*Primary Examiner* — James O Wilson
*Assistant Examiner* — Alexander R Pagano
(74) *Attorney, Agent, or Firm* — Baker Donelson Bearman Caldwell & Berkowitz, PC

(57) ABSTRACT

Compounds of the formula (I) and their agrochemically compatible salts

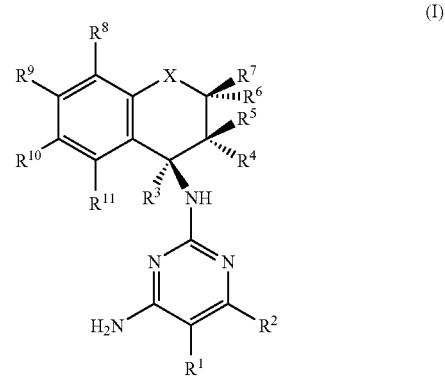

(I)

and their use in the field of crop protection are described.

21 Claims, No Drawings

FOREIGN PATENT DOCUMENTS

| | | |
|---|---|---|
| WO | 02/34048 A1 | 5/2002 |
| WO | 2004/069814 A1 | 8/2004 |
| WO | 2004/084631 A1 | 10/2004 |
| WO | 2005/015994 A1 | 2/2005 |
| WO | 2005/016001 A1 | 2/2005 |
| WO | WO 2005049033 A1 * | 6/2005 |
| WO | 2005/112630 A1 | 12/2005 |
| WO | 2007/023719 A1 | 1/2007 |
| WO | 2007/023764 A1 | 1/2007 |

OTHER PUBLICATIONS

Weed Research, 26 (1986), 441-445.
International Search Report, PCT/EP2009/009288, Mar. 3, 2010.
Kristinsson et al., "Synthesis of 5-Cyanopyrimidines," J. Chem. Soc., Chem. Commun., 1974, p. 350.
Schmidt et al., "A Convenient Synthesis of 2-Substituted 4-Amino-5-pyrimidinecarbonitriles," J Heterocycl. Chem., 1987, 24, pp. 1305-1307.
Wolter et al., "rbcS genes in *Solanum tuberosum*: Conservation of transit peptide and exon shuffling during evolution," Proc. Natl. Acad. Sci. USA 85 (1988), pp. 846-850.
Sonnewald et al., "Transgenic tobacco plants expressing yeast-derived invertase in either the cytosol, vacuole or apoplast: a powerful tool for studying sucrose metabolism and sink/source interactions," Plant J. 1 (1991), pp. 95-106.
Klingman, G.C., "Surface Active Agents," Weed Control as a Science, John Wiley and Sons, Inc., New York, 1961, pp. 81-96.

* cited by examiner

PYRIMIDINE DERIVATIVES AND THEIR USE FOR CONTROLLING UNDESIRED PLANT GROWTH

CROSS REFERENCE TO RELATED APPLICATIONS

This application claims priority to European Application 08022523.8 filed Dec. 30, 2008, the content of which is incorporated herein by reference in its entirety.

BACKGROUND OF THE INVENTION

1. Field of the Invention

The invention relates to the technical field of crop protection compositions, in particular to that of the herbicides for the selective control of weeds and weed grasses in crops of useful plants.

Specifically, it relates to 4-aminopyrimidines, to processes for their preparation and to their use for controlling harmful plants.

2. Description of Related Art

The prior art discloses pyrimidines which have a herbicidal effect. Thus, for example, EP 0 523 533 A1 describes certain substituted 4-aminopyrimidines and their use in the field of crop protection.

However, the use of the derivatives of this type as selective herbicides for controlling harmful plants or as plant growth regulators in various crops of useful plants often requires an excessive application rate or leads to undesired damage to the useful plants. Moreover, the use of the active ingredients is in many cases uneconomical on account of relatively high production costs.

It is therefore desirable to provide alternative chemical active ingredients based on pyrimidine derivatives which can be used as herbicides or plant growth regulators and with which certain advantages compared to systems known from the prior art are associated.

SUMMARY OF THE INVENTION

Consequently, in general, the object of the present invention is to provide alternative pyrimidine derivatives which can be used as herbicides or plant growth regulators, in particular with a satisfactory herbicidal effect against harmful plants, with a broad spectrum against harmful plants and/or with a high selectivity in crops of useful plants. These pyrimidine derivatives should here preferably exhibit a better profile of properties, in particular a better herbicidal effect against harmful plants, a broader spectrum in respect of harmful plants and/or a higher selectivity in crops of useful plants, than the pyrimidine derivatives known from the prior art.

According to the invention, then, novel pyrimidines have been found which can be used advantageously as herbicides and plant growth regulators. Besides a good activity profile and crop plant compatibility, the compounds of this series are characterized by cost-effective preparation processes and access options since the substances according to the invention can be prepared from inexpensive and readily accessible precursors and it is therefore possible to dispense with the use of costly and poor-availability intermediates.

Consequently, the present invention provides compounds of the formula (I) and their agrochemically compatible salts

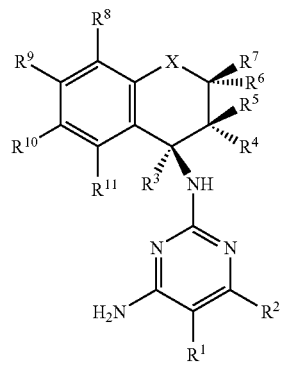

(I)

in welchen $R^1$ and $R^2$, independently of one another, are selected from the group consisting of hydrogen, halogen, hydroxy, cyano, nitro, amino, C(O)OH, $C(O)NH_2$;

$(C_1\text{-}C_6)$-alkyl, $(C_1\text{-}C_6)$-haloalkyl, $(C_1\text{-}C_6)$-alkylcarbonyl, $(C_1\text{-}C_6)$-haloalkylcarbonyl, $(C_1\text{-}C_6)$-alkylcarbonyloxy, $(C_1\text{-}C_6)$-haloalkylcarbonyloxy, $(C_1\text{-}C_6)$-alkylcarbonyl-$(C_1\text{-}C_4)$-alkyl;

$(C_1\text{-}C_6)$-alkoxy, $(C_1\text{-}C_6)$-haloalkoxy, $(C_1\text{-}C_6)$-alkoxycarbonyl, $(C_1\text{-}C_6)$-haloalkoxycarbonyl, $(C_1\text{-}C_6)$-alkoxycarbonyl-$(C_1\text{-}C_6)$-alkyl, $(C_1\text{-}C_6)$-haloalkoxycarbonyl-$(C_1\text{-}C_6)$-alkyl, $(C_1\text{-}C_6)$-alkoxycarbonyl-$(C_1\text{-}C_6)$-haloalkyl, $(C_1\text{-}C_6)$-haloalkoxycarbonyl-$(C_1\text{-}C_6)$-haloalkyl;

$(C_2\text{-}C_6)$-alkenyl, $(C_2\text{-}C_6)$-haloalkenyl, $(C_2\text{-}C_6)$-alkenylcarbonyl, $(C_2\text{-}C_6)$-haloalkenylcarbonyl, $(C_2\text{-}C_6)$-alkenyloxy, $(C_2\text{-}C_6)$-haloalkenyloxy, $(C_2\text{-}C_6)$-alkenyloxycarbonyl, $(C_2\text{-}C_6)$-haloalkenyloxycarbonyl;

$(C_2\text{-}C_6)$-alkynyl, $(C_2\text{-}C_6)$-haloalkynyl, $(C_2\text{-}C_6)$-alkynylcarbonyl, $(C_2\text{-}C_6)$-haloalkynylcarbonyl, $(C_2\text{-}C_6)$-alkynyloxy, $(C_2\text{-}C_6)$-haloalkynyloxy, $(C_2\text{-}C_6)$-alkynyloxycarbonyl, $(C_2\text{-}C_6)$-haloalkynyloxycarbonyl;

tri$(C_1\text{-}C_6)$-alkylsilyl-$(C_2\text{-}C_6)$-alkynyl, di$(C_1\text{-}C_6)$-alkylsilyl-$(C_2\text{-}C_6)$-alkynyl, mono$(C_1\text{-}C_6)$-alkylsilyl-$(C_2\text{-}C_6)$-alkynyl; phenylsilyl-$(C_2\text{-}C_6)$-alkynyl;

$(C_6\text{-}C_{14})$-aryl, $(C_6\text{-}C_{14})$-aryloxy, $(C_6\text{-}C_{14})$-arylcarbonyl and $(C_6\text{-}C_{14})$-aryl-oxycarbonyl, which may in each case be substituted on the aryl moiety by halogen, $(C_1\text{-}C_6)$-alkyl and/or $(C_1\text{-}C_6)$-haloalkyl;

$(C_6\text{-}C_{14})$-aryl-$(C_1\text{-}C_6)$-alkyl, $(C_6\text{-}C_{14})$-aryl-$(C_1\text{-}C_6)$-alkoxy, $(C_6\text{-}C_{14})$-aryl-$(C_1\text{-}C_6)$-alkylcarbonyl, $(C_6\text{-}C_{14})$-aryl-$(C_1\text{-}C_6)$-alkylcarbonyloxy, $(C_6\text{-}C_{14})$-aryl-$(C_1\text{-}C_6)$-alkoxycarbonyl, $(C_6\text{-}C_{14})$-aryl-$(C_1\text{-}C_6)$-alkoxycarbonyloxy;

mono$((C_1\text{-}C_6)$-alkyl)amino, mono$((C_1\text{-}C_6)$-haloalkyl)amino, di$((C_1\text{-}C_6)$-alkyl)amino, di$((C_1\text{-}C_6)$-haloalkyl)amino, $((C_1\text{-}C_6)$-alkyl-$(C_1\text{-}C_6)$-haloalkyl)amino, N—$((C_1\text{-}C_6)$-alkanoyl)amino, N—$((C_1\text{-}C_6)$-haloalkanoyl)-amino, aminocarbonyl-$(C_1\text{-}C_6)$-alkyl, di$(C_1\text{-}C_6)$-alkylaminocarbonyl-$(C_1\text{-}C_6)$-alkyl;

mono$((C_1\text{-}C_6)$-alkyl)aminocarbonyl, mono$((C_1\text{-}C_6)$-haloalkyl)amino-carbonyl, di$((C_1\text{-}C_6)$-alkyl)aminocarbonyl, di$((C_1\text{-}C_6)$-haloalkyl)amino-carbonyl, $((C_1\text{-}C_6)$-alkyl-$(C_1\text{-}C_6)$-haloalkyl)aminocarbonyl, N—$((C_1\text{-}C_6)$-alkanoyl)aminocarbonyl, N—$((C_1\text{-}C_6)$-haloalkanoyl)aminocarbonyl, mono$((C_6\text{-}C_{14})$-aryl)aminocarbonyl, di$((C_6\text{-}C_{14})$-aryl)aminocarbonyl, ($C_1$-$C_6$)-alkoxy-($C_1$-$C_6$)-alkyl, ($C_1$-$C_6$)-alkoxy-($C_1$-$C_6$)-alkoxy, ($C_1$-$C_6$)-alkoxycarbonyl-($C_1$-$C_6$)-alkoxy;

($C_3$-$C_8$)-cycloalkyl, which may be optionally substituted on the cycloalkyl radical by ($C_1$-$C_6$)-alkyl and/or halogen; ($C_3$-$C_8$)-cycloalkoxy, ($C_3$-$C_8$)-cycloalkyl-($C_1$-$C_6$)-alkyl, ($C_3$-$C_8$)-cycloalkyl-($C_1$-$C_6$)-haloalkyl, ($C_3$-$C_8$)-cycloalkyl-($C_1$-$C_6$)-alkoxy, ($C_3$-$C_8$)-cycloalkyl-($C_1$-$C_6$)-haloalkoxy, ($C_3$-$C_8$)-cycloalkylcarbonyl, ($C_3$-$C_8$)-cycloalkoxycarbonyl, ($C_3$-$C_8$)-cycloalkyl-($C_1$-$C_6$)-alkylcarbonyl, ($C_3$-$C_8$)-cycloalkyl-($C_1$-$C_6$)-haloalkylcarbonyl, ($C_3$-$C_8$)-cycloalkyl-($C_1$-$C_6$)-alkoxycarbonyl, ($C_3$-$C_8$)-cycloalkyl-($C_1$-$C_6$)-haloalkoxycarbonyl, ($C_3$-$C_8$)-cycloalkylcarbonyloxy, ($C_3$-$C_8$)-cycloalkoxycarbonyloxy, ($C_3$-$C_8$)-cycloalkyl-($C_1$-$C_6$)-alkylcarbonyloxy, ($C_3$-$C_8$)-cycloalkyl-($C_1$-$C_6$)-haloalkylcarbonyloxy, ($C_3$-$C_8$)-cycloalkyl-($C_1$-$C_6$)-alkoxycarbonyloxy, ($C_3$-$C_8$)-cycloalkyl-($C_1$-$C_6$)-haloalkoxycarbonyloxy;

($C_3$-$C_8$)-cycloalkenyl, ($C_3$-$C_8$)-cycloalkenyloxy, ($C_3$-$C_8$)-cycloalkenyl-($C_1$-$C_6$)-alkyl, ($C_3$-$C_8$)-cycloalkenyl-($C_1$-$C_6$)-haloalkyl, ($C_3$-$C_8$)-cycloalkenyl-($C_1$-$C_6$)-alkoxy, ($C_3$-$C_8$)-cycloalkenyl-($C_1$-$C_6$)-haloalkoxy, ($C_3$-$C_8$)-cycloalkenylcarbonyl, ($C_3$-$C_8$)-cycloalkenyloxycarbonyl, ($C_3$-$C_8$)-cycloalkenyl-($C_1$-$C_6$)-alkylcarbonyl, ($C_3$-$C_8$)-cycloalkenyl-($C_1$-$C_6$)-haloalkylcarbonyl, ($C_3$-$C_8$)-cycloalkenyl-($C_1$-$C_6$)-alkoxycarbonyl, ($C_3$-$C_8$)-cycloalkenyl-($C_1$-$C_6$)-haloalkoxycarbonyl, ($C_3$-$C_8$)-cycloalkenylcarbonyloxy, ($C_3$-$C_8$)-cycloalkenyloxycarbonyloxy, ($C_3$-$C_8$)-cycloalkenyl-($C_1$-$C_6$)-alkylcarbonyloxy, ($C_3$-$C_8$)-cycloalkenyl-($C_1$-$C_6$)-haloalkylcarbonyloxy, ($C_3$-$C_8$)-cycloalkenyl-($C_1$-$C_6$)-alkoxycarbonyloxy, ($C_3$-$C_8$)-cycloalkenyl-($C_1$-$C_6$)-haloalkoxycarbonyloxy;

hydroxy-($C_1$-$C_6$)-alkyl, hydroxy-($C_1$-$C_6$)-alkoxy, cyano-($C_1$-$C_6$)-alkoxy, cyano-($C_1$-$C_6$)-alkyl;

($C_1$-$C_6$)-alkylsulfonyl, ($C_1$-$C_6$)-alkylthio, ($C_1$-$C_6$)-alkylsulfinyl, ($C_1$-$C_6$)-haloalkylsulfonyl, ($C_1$-$C_6$)-haloalkylthio, ($C_1$-$C_6$)-haloalkylsulfinyl, ($C_1$-$C_6$)-alkylsulfonyl-($C_1$-$C_6$)-alkyl, ($C_1$-$C_6$)-alkylthio-($C_1$-$C_6$)-alkyl, ($C_1$-$C_6$)-alkylsulfinyl-($C_1$-$C_6$)-alkyl, ($C_1$-$C_6$)-haloalkylsulfonyl-($C_1$-$C_6$)-alkyl, ($C_1$-$C_6$)-haloalkylthio-($C_1$-$C_6$)-alkyl, ($C_1$-$C_6$)-haloalkylsulfinyl-($C_1$-$C_6$)-alkyl, ($C_1$-$C_6$)-alkylsulfonyl-($C_1$-$C_6$)-haloalkyl, ($C_1$-$C_6$)-alkylthio-($C_1$-$C_6$)-haloalkyl, ($C_1$-$C_6$)-alkylsulfinyl-($C_1$-$C_6$)-haloalkyl, ($C_1$-$C_6$)-haloalkylsulfonyl-($C_1$-$C_6$)-haloalkyl, ($C_1$-$C_6$)-haloalkylthio-($C_1$-$C_6$)-haloalkyl, ($C_1$-$C_6$)-haloalkylsulfinyl-($C_1$-$C_6$)-haloalkyl, ($C_1$-$C_6$)-alkylsulfonyloxy, ($C_1$-$C_6$)-haloalkylsulfonyloxy, ($C_1$-$C_6$)-alkylthiocarbonyl, ($C_1$-$C_6$)-haloalkylthiocarbonyl, ($C_1$-$C_6$)-alkylthiocarbonyloxy, ($C_1$-$C_6$)-haloalkyl-thiocarbonyloxy, ($C_1$-$C_6$)-alkylthio-($C_1$-$C_6$)-alkyl, ($C_1$-$C_6$)-alkylthio-($C_1$-$C_6$)-alkoxy, ($C_1$-$C_6$)-alkylthio-($C_1$-$C_6$)-alkylcarbonyl, ($C_1$-$C_6$)-alkylthio-($C_1$-$C_6$)-alkylcarbonyloxy, ($C_4$-$C_{14}$)-arylsulfonyl, ($C_6$-$C_{14}$)-arylthio, ($C_6$-$C_{14}$)-arylsulfinyl, ($C_3$-$C_8$)-cycloalkylthio, ($C_3$-$C_8$)-alkenylthio, ($C_3$-$C_8$)-cycloalkenylthio, ($C_3$-$C_6$)-alkynylthio;

the radicals $R^1$ and $R^2$ together form a ($C_2$-$C_6$)-alkylene group, which may comprise one or more oxygen and/or sulfur atoms, where the ($C_2$-$C_6$)-alkylene group may be mono- or polysubstituted by halogen and the respective halogen substituents may be identical or different; and $R^3$ is selected from the group consisting of hydrogen, ($C_1$-$C_6$)-alkyl and ($C_1$-$C_6$)-haloalkyl;

$R^4$ and $R^5$ in each case independently of one another are selected from the group consisting of hydrogen, ($C_1$-$C_6$)-alkyl, ($C_1$-$C_6$)-haloalkyl, hydroxy, ($C_1$-$C_6$)-alkoxy and ($C_1$-$C_6$)-haloalkoxy; or the radicals $R^4$ and $R^5$, together with the carbon atom to which they are bonded, form a three- to seven-membered ring;

$R^6$ and $R^7$ in each case independently of one another are selected from the group consisting of hydrogen, ($C_1$-$C_6$)-alkyl, ($C_1$-$C_6$)-haloalkyl, ($C_1$-$C_6$)-alkoxy, ($C_1$-$C_6$)-haloalkoxy, ($C_6$-$C_{14}$)-aryl, ($C_6$-$C_{14}$)-aryloxy, ($C_6$-$C_{14}$)-arylcarbonyl and ($C_6$-$C_{14}$)-aryloxycarbonyl; or the radicals $R^6$ and $R^7$ together form a ($C_2$-$C_7$)-alkylene group, which may comprise one or more oxygen and/or sulfur atoms, where the ($C_2$-$C_7$)-alkylene group may be mono- or polysubstituted by halogen and the respective halogen substituents may be identical or different, $R^8$, $R^9$, $R^{19}$ and $R^{11}$, independently of one another, are in each case selected from the group consisting of hydrogen, halogen, cyano, ($C_1$-$C_6$)-alkyl, ($C_1$-$C_6$)-alkylcarbonyl, ($C_1$-$C_6$)-alkyloxycarbonyl, ($C_1$-$C_6$)-alkylaminocarbonyl, ($C_1$-$C_6$)-dialkylaminocarbonyl, ($C_1$-$C_6$)-haloalkyl, ($C_1$-$C_6$)-alkoxy, ($C_1$-$C_6$)-haloalkoxy, ($C_2$-$C_6$)-alkynyl, ($C_2$-$C_6$)-haloalkynyl, ($C_2$-$C_6$)-alkynylcarbonyl, ($C_2$-$C_6$)-haloalkynylcarbonyl, ($C_2$-$C_6$)-alkynyloxy, ($C_2$-$C_6$)-haloalkynyloxy, ($C_2$-$C_6$)-alkynyloxycarbonyl and ($C_2$-$C_6$)-haloalkynyloxycarbonyl and nitro;

X is a bond, $CH_2$, O, S, carbonyl, NH, $CR^{12}R^{13}$ and $NR^{14}$;

$R^{12}$ and $R^{13}$ in each case independently of one another are selected from the group consisting of hydrogen, ($C_1$-$C_6$)-alkyl and ($C_1$-$C_6$)-haloalkyl; and $R^{14}$ is selected from the group consisting of hydrogen, ($C_1$-$C_6$)-alkyl, ($C_1$-$C_6$)-haloalkyl.

DETAILED DESCRIPTION OF A PREFERRED EMBODIMENT

According to the invention, it has been found that these compounds have a good activity profile and crop plant compatibility.

The compounds according to the invention differ from the compounds according to EP 0 523 533 A1 in that they are not substituted 4-aminopyrimidines, but bicyclically substituted 2-aminopyrimidine-4-amines.

Now, firstly preferred, particularly preferred and very particularly preferred meanings for the individual substituents are described below.

A first embodiment of the present invention encompasses compounds of the formula (I) in which $R^1$ is preferably selected from the group consisting of hydrogen, halogen, cyano, C(=O)$NH_2$, $NO_2$, ($C_1$-$C_6$)-alkyl, ($C_1$-$C_6$)-alkylcarbonyl, ($C_1$-$C_6$)-haloalkyl, ($C_3$-$C_6$)-cyclopropyl, ($C_1$-$C_6$)-alkoxy, ($C_1$-$C_6$)-thioalkyl, ($C_1$-$C_6$)-alkylthio, ($C_2$-$C_6$)-alkynyl, mono($C_1$-$C_6$)-alkylamino, di($C_1$-$C_6$)-alkylamino and tri($C_1$-$C_6$)-alkylsilyl-($C_2$-$C_6$)-alkynyl;

$R^1$ is particularly preferably selected from the group consisting of hydrogen, cyano, fluorine, chlorine, bromine, iodine, nitro, trimethylsilylethynyl, methyl, ethyl, propyl, isopropyl, butyl, tert-butyl, n-pentyl, n-heptyl, cyclopropyl, cyclobutyl, acetyl, ethynyl, amino, dimethylamino, trifluoromethyl, difluoromethyl, monofluoromethyl, methoxy, ethoxy and methoxymethyl; and $R^1$ is very particularly preferably cyano, acetyl and trifluoromethyl.

A second embodiment of the present invention encompasses compounds of the formula (I) in which $R^2$ is preferably selected from the group consisting of hydrogen, halogen, $(C_1-C_6)$-alkylphenyl; $(C_6-C_{14})$-aryl, which may be substituted on the aryl radical by $(C_1-C_6)$-alkyl, $(C_6-C_{14})$-haloalkyl and/or halogen; $C_6$-aryl-$(C_1-C_6)$-haloalkyl, $(C_1-C_6)$-alkyl, $(C_1-C_6)$-haloalkyl, $(C_1-C_6)$-alkoxy, $(C_1-C_6)$-alkoxy-$(C_1-C_6)$-alkyl; $(C_3-C_6)$-cycloalkyl, which may be substituted on the cycloalkyl radical by $(C_1-C_6)$-alkyl, $(C_6-C_{14})$-haloaryl and/or halogen; 1-$(C_1-C_6)$-alkylcyclopropyl, 1-$((C_1-C_6)$-alkyl-$C_6$-aryl)cyclopropyl, 1-(monohalophenyl)cyclopropyl, 1-(dihalophenyl)cyclopropyl, mono$(C_1-C_6)$-alkylamino, di$(C_1-C_6)$-alkylamino, $(C_1-C_6)$-thioalkyl, $(C_1-C_6)$-alkylthio, $(C_1-C_6)$-alkoxy and amino;

$R^2$ is particularly preferably selected from the group consisting of hydrogen, chlorine, phenyl, 2-methylphenyl, 3-trifluoromethylphenyl, methyl, ethyl, isopropyl, butyl, tert-butyl, n-pentyl, n-heptyl, trifluoromethyl, 1-methylcyclopropyl, 1-(p-xylyl)cyclopropyl, 1-(2,4-dichlorophenyl)cyclopropyl, amino, dimethylamino, trifluoromethyl, difluoromethyl, monofluoromethyl, $CHFCH_3$, $CF(CH_3)_2$, $CHF(CH_2CH_3)$, 1-fluorocyclopropyl, cyclopentyl, methoxy, ethoxy, methoxymethyl, ethoxymethyl, thiomethyl, methylthio and methoxy; and $R^2$ is very particularly preferably hydrogen, methyl or difluoromethyl.

A third embodiment of the present invention encompasses compounds of the formula (I) in which $R^1$ and $R^2$, preferably together with the carbon atoms to which they are bonded, form a five- or six-membered ring, which may be interrupted by one or two heteroatoms selected from the group consisting of oxygen and sulfur;
particularly preferably together with the carbon atoms to which they are bonded, form a five-membered ring, which may be interrupted by a heteroatom selected from the group consisting of oxygen and sulfur; and
are very particularly preferably —$CH_2$—$CH_2$—$CH_2$— or —$CH_2$—S—$CH_2$—.

A fourth embodiment of the present invention encompasses compounds of the formula (I) in which $R^3$ is preferably hydrogen or $(C_1-C_6)$-alkyl; and
$R^3$ is particularly preferably hydrogen.

A fifth embodiment of the present invention encompasses compounds of the formula (I) in which $R^4$ and $R^5$, in each case independently of one another, are preferably selected from the group consisting of hydrogen, $(C_1-C_6)$-alkyl, hydroxy, cyclopropyl and $(C_1-C_6)$-alkoxy;

$R^4$ and $R^5$, in each case independently of one another, are particularly preferably selected from the group consisting of hydrogen, methyl, ethyl, propyl, cyclopropyl, hydroxy and methoxy; and $R^4$ and $R^5$, in each case independently of one another, are very particularly preferably methyl, ethyl or hydrogen.

In this fifth embodiment, it is specifically preferred if at least one of the radicals $R^4$ or $R^5$ is hydrogen. It is further preferred if at least one of the radicals $R^4$ or $R^5$ is hydrogen and the other radical $R^4$ or $R^5$ is not hydrogen, in particular $(C_1-C_6)$-alkyl.

In this fifth embodiment, it is very specifically preferred if one of the radicals $R^4$ or $R^5$ is hydrogen and the other radical of $R^4$ or $R^5$ is methyl.

A sixth embodiment of the present invention encompasses compounds of the formula (I) in which $R^4$ and $R^5$ preferably together form a $(C_2-C_7)$-alkylene group which may comprise one or more oxygen and/or sulfur atoms, where the $(C_2-C_7)$-alkylene group may be mono- or polysubstituted by halogen and the respective halogen substituents may be identical or different; and $R^4$ and $R^5$, particularly preferably together with the carbon atom to which they are bonded, form a three- or four-membered ring; and
are particularly preferably —$CH_2$—$CH_2$—$CH_2$— or —$CH_2$—$CH_2$—.

A seventh embodiment of the present invention encompasses compounds of the formula (I) in which $R^6$ and $R^7$, independently of one another, are preferably selected from the group consisting of hydrogen, $(C_1-C_6)$-alkyl and $(C_6-C_{14})$-aryl;

$R^6$ and $R^7$, independently of one another, are particularly preferably selected from the group consisting of hydrogen, methyl and phenyl; and $R^6$ and $R^7$ are very particularly preferably hydrogen.

An eighth embodiment of the present invention encompasses compounds of the formula (I) in which $R^8$ is preferably selected from the group consisting of hydrogen, $(C_1-C_6)$-alkyl or halogen;

$R^8$ is particularly preferably selected from the group consisting of hydrogen, methyl or fluorine; and $R^8$ is very particularly preferably hydrogen.

A ninth embodiment of the present invention encompasses compounds of the formula (I) in which $R^9$ is preferably selected from the group consisting of hydrogen and $(C_1-C_6)$-alkyl;

$R^9$ is particularly preferably selected from the group consisting of hydrogen and methyl; and $R^9$ is very particularly preferably hydrogen.

A tenth embodiment of the present invention encompasses compounds of the formula (I) in which $R^{10}$ is preferably selected from the group consisting of hydrogen, $(C_1-C_6)$-alkyl, di$(C_1-C_6)$-alkylamino, halogen, $(C_2-C_6)$-alkenyl, $(C_2-C_6)$-alkynyl, $(C_1-C_6)$-alkyl-$(C_2-C_6)$-alkynyl, $(C_1-C_6)$-alkoxy-$(C_1-C_6)$-alkyl-$(C_2-C_6)$-alkynyl, cyano, $(C_1-C_6)$-alkoxycarbonyl and aminocarbonyl;

$R^{10}$ is particularly preferably selected from the group consisting of hydrogen, methyl, propyl, isopropyl, butyl, tert-butyl, dimethylamino, fluorine, chlorine, bromine, iodine, ethenyl, ethynyl, methylethynyl, ethylethynyl, $MeOCH_2C{\equiv}C$—, cyano, COOMe and $CONH_2$; and $R^{10}$ is very particularly preferably hydrogen or methyl.

An eleventh embodiment of the present invention encompasses compounds of the formula (I) in which $R^{11}$ is preferably selected from the group consisting of hydrogen and $(C_1-C_6)$-alkyl;

$R^{11}$ is particularly preferably selected from the group consisting of hydrogen and methyl; and $R^{11}$ is very particularly preferably hydrogen.

A twelfth embodiment of the present invention encompasses compounds of the formula (I) in which X is particularly preferably selected from the group consisting of $CH_2$, O and a chemical bond.

Within the context of the present invention, it is possible to combine the individual preferred, particularly preferred and very particularly preferred meanings for the substituents $R^1$ to $R^{11}$ and X with one another as desired. This means that compounds of the formula (I) are encompassed by the present invention in which, for example, the substituent $R^1$ has a preferred meaning and the substituents $R^2$ to $R^{11}$ have the general meaning, or else the substituent $R^2$ has a preferred meaning, the substituent $R^3$ has a particularly preferred meaning and the other substituents have a general meaning.

Within the context of the present invention, the compound of the formula (I) also encompasses compounds which have been quaternized by a) protonation, b) alkylation or c) oxidation on a nitrogen atom. In particular, the corresponding N-oxides are to be mentioned in this connection.

The compounds of the formula (I) can form salts.

Salt formation can take place as a result of the action of a base on those compounds of the formula (I) which carry an acidic hydrogen atom, e.g. when $R^1$ comprises a COOH group or a sulfonamide group —NHSO$_2$—. Suitable bases are, for example, organic amines, such as trialkylamines, morpholine, piperidine or pyridine, and also ammonium, alkali metal or alkaline earth metal hydroxides, carbonates and hydrogencarbonates, in particular sodium hydroxide and potassium hydroxide, sodium carbonate and potassium carbonate and sodium hydrogencarbonate and potassium hydrogencarbonate. These salts are compounds in which the acidic hydrogen is replaced by a cation suitable for agriculture, for example metal salts, in particular alkali metal salts or alkaline earth metal salts, in particular sodium salts and potassium salts, and also ammonium salts, salts with organic amines or quaternary ammonium salts, for example with cations of the formula [NRR'R''R''']$^+$, in which R to R''', in each case independently of one another, are an organic radical, in particular alkyl, aryl, aralkyl or alkylaryl. Also suitable are alkylsulfonium and alkylsulfoxonium salts, such as ($C_1$-$C_4$)-trialkylsulfonium and ($C_1$-$C_4$)-trialkylsulfoxonium salts.

The compounds of the formula (I) can form salts through addition reaction of a suitable inorganic or organic acid, such as, for example, mineral acids, such as, for example, HCl, HBr, $H_2SO_4$, $H_3PO_4$ or $HNO_3$, or organic acids, for example carboxylic acids, such as formic acid, acetic acid, propionic acid, oxalic acid, lactic acid or salicylic acid, or sulfonic acids, such as, for example, p-toluenesulfonic acid, onto a basic group, such as, for example, amino, alkylamino, dialkylamino, piperidino, morpholino or pyridino. These salts then comprise the conjugated base of the acid as anion.

Suitable substituents which are present in deprotonated form, such as, for example, sulfonic acids or carboxylic acids, can form internal salts with groups that for their part are protonatable, such as amino groups.

The compounds of the formula (I) and their salts are also referred to below for short as "compounds (I)" according to the invention or used according to the invention.

In the formula (I) and all of the other formulae in the present invention, the radicals alkyl, alkoxy, haloalkyl, haloalkoxy, alkylamino, alkylthio, haloalkylthio, and the corresponding unsaturated and/or substituted radicals in the carbon backbone may in each case be straight-chain or branched. Unless specifically stated, in the case of these radicals, preference is given to the lower carbon backbones, e.g. having 1 to 6 carbon atoms, in particular 1 to 4 carbon atoms, or in the case of unsaturated groups having 2 to 6 carbon atoms, in particular 2 to 4 carbon atoms. Alkyl radicals, including in the composite meanings such as alkoxy, haloalkyl etc., mean, for example, methyl, ethyl, n-propyl or isopropyl, n-butyl, isobutyl, t-butyl or 2-butyl, pentyls, hexyls, such as n-hexyl, isohexyl and 1,3-dimethylbutyl, heptyls, such as n-heptyl, 1-methylhexyl and 1,4-dimethylpentyl; alkenyl and alkynyl radicals have the meaning of the possible unsaturated radicals corresponding to the alkyl radicals; where at least one double bond or triple bond, preferably one double bond or triple bond, is present. Alkenyl is, for example, vinyl, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl; alkynyl is, for example, ethynyl, propargyl, but-2-yn-1-yl, but-3-yn-1-yl and 1-methylbut-3-yn-1-yl.

Cycloalkyl groups are, for example, cyclopropyl, cyclobutyl, cyclopentyl, cyclohexyl, cycloheptyl and cyclooctyl. The cycloalkyl groups can occur in bi- or tricyclic form.

If haloalkyl groups and haloalkyl radicals of haloalkoxy, haloalkylthio, haloalkenyl, haloalkynyl etc. are given, in these radicals, the lower carbon backbones, e.g. having 1 to 6 carbon atoms or 2 to 6, in particular 1 to 4 carbon atoms or preferably 2 to 4 carbon atoms, and also the corresponding unsaturated and/or substituted radicals in the carbon backbone are in each case straight-chain or branched. Examples are difluoromethyl, 2,2,2-trifluoroethyl, trifluoroallyl, 1-chloroprop-1-yl-3-yl.

In these radicals, alkylene groups are the lower carbon backbones, e.g. having 1 to 10 carbon atoms, in particular 1 to 6 carbon atoms or preferably 2 to 4 carbon atoms, and the corresponding unsaturated and/or substituted radicals in the carbon backbone, which may in each case be straight-chain or branched. Examples are methylene, ethylene, n-propylene and isopropylene and n-butylene, sec-butylene, isobutylene, t-butylene.

In these radicals, hydroxyalkyl groups are the lower carbon backbones, e.g. having 1 to 6 carbon atoms, in particular 1 to 4 carbon atoms, and the corresponding unsaturated and/or substituted radicals in the carbon backbone, which may in each case be straight-chain or branched. Examples thereof are 1,2-dihydroxyethyl and 3-hydroxypropyl.

Halogen is fluorine, chlorine, bromine or iodine. Haloalkyl, haloalkenyl and haloalkynyl are alkyl, alkenyl or alkynyl, respectively, partially or completely substituted by halogen, preferably by fluorine, chlorine or bromine, in particular by fluorine and/or chlorine, e.g. monohaloalkyl, perhaloalkyl, $CF_3$, $CHF_2$, $CH_2F$, $CF_3CF_2$, $CH_2FCHCl$, $CCl_3$, $CHCl_2$, $CH_2CH_2Cl$; haloalkoxy is e.g. $OCF_3$, $OCHF_2$, $OCH_2F$, $CF_3CF_2O$, $OCH_2CF_3$ and $OCH_2CH_2Cl$; the same applies for haloalkenyl and other radicals substituted by halogen.

Aryl is a mono-, bi- or polycyclic aromatic system, for example phenyl or naphthyl, preferably phenyl.

Primarily for reasons of higher herbicidal effect, better selectivity and/or better producibility, compounds of the formula (I) according to the invention or their agrochemical salts or quaternary N derivatives are of particular interest in which individual radicals have one of the preferred meanings already specified or specified below, or in particular those in which one or more of the preferred meanings already specified or specified below occur in combination.

The radical definitions given above in general or given in preferred ranges apply both for the end products of the formula (I) and also correspondingly for the starting materials and intermediates required in each case for the preparation. These radical definitions can be exchanged among one another, and also between the stated preferred ranges.

The present compounds of the formula (I) have a chiral carbon atom which is shown in the structure depicted below by the symbol (*):

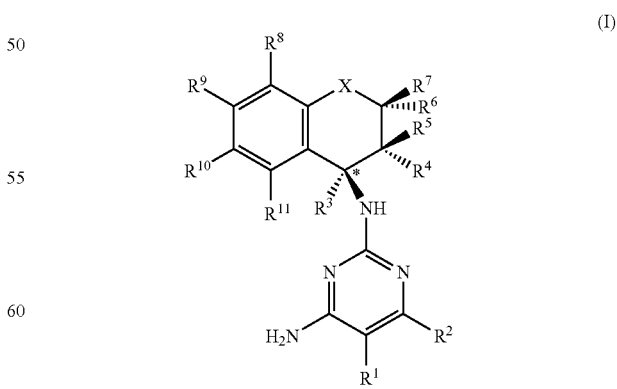

(I)

According to the rules in accordance with Cahn, Ingold and Prelog (CIP rules), this carbon atom can have either an (R) configuration or an (S) configuration.

The present invention encompasses compounds of the formula (I) both with (S) and with (R) configuration, i.e. the present invention encompasses the compounds of the formula (I) in which the carbon atom in question has
(1) an (R) configuration; or
(2) an (S) configuration.
Moreover, the present invention also encompasses
(3) any desired mixtures of compounds of the formula (I) which have an (R) configuration (compounds of the formula (I-(R)), with compounds of the formula (I) which have an (S) configuration (compounds of the formula (I-(S)),
where a racemic mixture of the compounds of the formula (I) with (R) and (S) configuration is likewise encompassed by the present invention.

However, within the context of the present invention, preference is given in particular to compounds of the formula (I) having (R) configuration with a selectivity of 60 to 100%, preferably 80 to 100%, in particular 90 to 100%, very particularly 95 to 100%, where the particular (R) compound is present with an enantioselectivity of in each case more than 50% ee, preferably 60 to 100% ee, in particular 80 to 100% ee, very particularly 90 to 100% ee, most preferably 95 to 100% ee, based on the total content of (R) compound in question.

Consequently, the present invention relates in particular to compounds of the formula (I) in which the stereochemical configuration on the carbon atom indicated by (*) is present with a stereochemical purity of 60 to 100% (R), preferably 80 to 100% (R), in particular 90 to 100% (R), very particularly 95 to 100% (R).

Taking into consideration the Cahn, Ingold and Prelog rules, on the carbon atom indicated by (*), a situation may also arise in which, on account of the priority of the respective substituents, the (S) configuration is preferred on the carbon atom indicated by (*). This is the case, for example, when the radicals $R^4$ and/or $R^5$ are a $C_1$-$C_6$-alkoxy radical.

Consequently, within the context of the present invention, preference is given in particular to compounds of the formula (I) which, in their spatial arrangement, correspond to those compounds of the formula (I) where $R^4$ and $R^5$=hydrogen with (R) configuration, with a selectivity of 60 to 100%, preferably 80 to 100%, in particular 90 to 100%, very particularly 95 to 100%, where the particular (R)-analogous compound is present with an enantioselectivity of in each case more than 50% ee, preferably 60 to 100% ee, in particular 80 to 100% ee, very particularly 90 to 100% ee, most preferably 95 to 100% ee, based on the total content of (R)-analogous compound in question. Consequently, the present invention relates in particular to compounds of the formula (I) in which the stereochemical configuration on the carbon atom indicated by (*) is present with a stereochemical purity of 60 to 100% (R, or analogous-R), preferably 80 to 100% (R, or analogous-R), in particular 90 to 100% (R, or analogous-R), very particularly 95 to 100% (R, or analogous-R).

In particular, the compounds of the formula (I) according to the invention can also have further chirality centers on the carbon atoms indicated by () and (*):

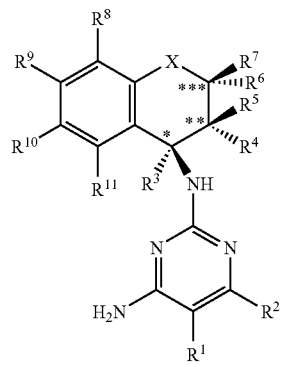

Within the context of the present invention, any desired stereochemical configurations on the carbon atoms indicated by (*), () and (*) are possible:

| Configuration of carbon atom (*) | Configuration of carbon atom () | Configuration of carbon atom (*) |
| --- | --- | --- |
| R | R | R |
| R | R | S |
| R | S | R |
| S | R | R |
| R | S | S |
| S | R | S |
| S | S | R |
| S | S | S |

Moreover, depending on the selection of the particular radicals, further stereoelements may be present in the compounds of the formula (I) according to the invention.

If, for example, one or more alkenyl groups are present, then diastereomers (Z and E isomers) can occur.

If, for example, one or more asymmetric carbon atoms are present, then enantiomers and diastereomers can occur.

Corresponding stereoisomers can be obtained from the mixtures produced during the preparation by customary separation methods, for example by chromatographic separation methods. Stereoisomers can likewise be selectively prepared by employing stereoselective reactions using optically active starting materials and/or auxiliaries. The invention thus also relates to all stereoisomers which are encompassed by the formula (I), but are not stated with their specific stereoform, and mixtures thereof.

The combination possibilities of the various substituents of the formula (I) are to be understood such that the general principles of constructing chemical compounds are observed, i.e. the formula (I) does not encompass compounds which the person skilled in the art knows are not chemically possible.

The table below gives specific examples of the compounds of the formula (I) according to the invention:

TABLE

| | $R^1$ | $R^2$ | $R^3$ | Stereo N, $R^3$ | $R^4$ | $R^5$ |
| --- | --- | --- | --- | --- | --- | --- |
| 1.1. | H | $CF_3$ | H | rac | H | H |
| 1.2. | H | $CF_3$ | H | rac | H | H |
| 1.3. | H | $CF_3$ | H | rac | H | H |
| 1.4. | H | $CF_2H$ | H | rac | H | H |
| 1.5. | H | $CF_2H$ | H | rac | H | H |

TABLE-continued

| | | | | | | |
|---|---|---|---|---|---|---|
| 1.6. | H | CF₂H | H | rac | H | H |
| 1.7. | OCH₃ | CF₃ | H | rac | H | H |
| 1.8. | H | CF₃ | H | rac | CH₃ | H |
| 1.9. | H | C(CH₃)₃ | H | rac | H | H |
| 1.10. | H | C(CH₃)₃ | H | rac | H | H |
| 1.11. | H | C(CH₃)₃ | H | rac | H | H |
| 1.12. | H | CH₂CH₃ | H | rac | H | H |
| 1.13. | H | CH₂CH₃ | H | rac | H | H |
| 1.14. | H | CH₂CH₃ | H | rac | H | H |
| 1.15. | OCH₃ | CH₂CH₃ | H | rac | H | H |
| 1.16. | H | CH₂CH₃ | H | rac | CH₃ | H |
| 1.17. | CN | CH₃ | H | R | CH₃ | H |
| 1.18. | CN | CH₃ | H | R | H | H |
| 1.19. | C(=O)OCH₃ | CH₃ | H | R | H | H |
| 1.20. | C(=O)NH₂ | CH₃ | H | R | H | H |
| 1.21. | C(=O)NHPh | CH₃ | H | R | H | H |
| 1.22. | C(=O)N(CH₃)₂ | CH₃ | H | R | H | H |
| 1.23. | CN | CH₃ | H | rac | CH₃ | H |
| 1.24. | CN | CH₃ | H | rac | H | H |
| 1.25. | CN | CH₃ | H | rac | H | H |
| 1.26. | CN | CH₃ | H | R | H | H |
| 1.27. | CN | CH₃ | H | rac | H | H |
| 1.28. | CN | CH₃ | H | rac | H | H |
| 1.29. | CN | CF₃ | H | rac | H | H |
| 1.30. | CN | H | H | R | H | H |
| 1.31. | CN | CF₂H | H | rac | H | H |
| 1.32. | CN | CF₂CF₂H | H | rac | H | H |
| 1.33. | CN | H | H | R | H | H |
| 1.34. | CN | H | H | rac | H | H |
| 1.35. | CN | H | H | R | CH₃ | H |
| 1.36. | C(=O)OH | H | H | R | CH₃ | H |
| 1.37. | I | H | H | R | H | H |
| 1.38. | H | H | H | R | CH₃ | H |
| 1.39. | C≡CSi(CH₃)₃ | H | H | R | H | H |
| 1.40. | H | CH₃ | H | R | H | H |
| 1.41. | H | CH₃ | H | R | CH₃ | H |
| 1.42. | H | CH₃ | H | rac | H | H |
| 1.43. | CH₃ | CH₃ | H | rac | H | H |
| 1.44. | CH₃ | CH₃ | H | rac | H | H |
| 1.45. | CH₃ | CH₃ | H | rac | H | H |
| 1.46. | I | CH₃ | H | R | CH₃ | H |
| 1.47. | C≡CSi(CH₃)₃ | CH₃ | H | R | CH₃ | H |
| 1.48. | C≡CH | CH₃ | H | R | CH₃ | H |
| 1.49. | C≡CPh | CH₃ | H | R | CH₃ | H |
| 1.50. | CH=CHPh | CH₃ | H | R | CH₃ | H |
| 1.51. | CH₃ | H | H | R | CH₃ | H |
| 1.52. | CH₃ | H | CH₃ | rac | H | H |
| 1.53. | CH₃ | H | CH₂CH₃ | rac | H | H |
| 1.54. | CH₃ | H | CH₃ | rac | H | H |
| 1.55. | CH₃ | H | CH₃ | rac | H | H |
| 1.56. | F | H | H | R | CH₃ | H |
| 1.57. | F | CH₃ | H | R | CH₃ | H |
| 1.58. | F | CF₂H | H | R | CH₃ | H |
| 1.59. | Cl | CH₃ | H | R | CH₃ | H |
| 1.60. | Cl | CF₂H | H | R | CH₃ | H |
| 1.61. | CN | CH₂CH₃ | H | R | CH₃ | H |
| 1.62. | CN | CH₂CH₃ | H | R | H | H |
| 1.63. | CN | CH₂CH₃ | H | R | H | H |
| 1.64. | CN | CH(CH₃)₂ | H | R | CH₃ | H |
| 1.65. | CN | CH(CH₃)₂ | H | R | H | H |
| 1.66. | CN | CH(CH₃)₂ | H | R | H | H |
| 1.67. | Br | H | H | R | CH₃ | H |
| 1.68. | CN | CF₂H | H | R | CH₃ | H |
| 1.69. | CN | CF₂H | H | rac | H | H |
| 1.70. | CN | CF₂H | H | R | H | H |
| 1.71. | CN | CF₂H | H | rac | H | H |
| 1.72. | CN | CF₂H | H | rac | CH₃ | CH₃ |
| 1.73. | CN | CF₂H | H | rac | CH₃ | CH₃ |
| 1.74. | CN | CF₂H | H | rac | —CH₂CH₂— | |
| 1.75. | H | Cl | H | R | CH₃ | H |
| 1.76. | H | Cl | H | R | H | H |
| 1.77. | CN | 2-(CH₃)-Ph | H | R | CH₃ | H |
| 1.78. | CN | 2-(CH₃)-Ph | H | R | H | H |
| 1.79. | CN | 2-(CH₃)-Ph | H | rac | H | H |
| 1.80. | CN | 3-(CF₃)-Ph | H | R | CH₃ | H |
| 1.81. | CN | 3-(CF₃)-Ph | H | R | H | H |
| 1.82. | CN | 3-(CF₃)-Ph | H | rac | H | H |
| 1.83. | H | Ph | H | R | CH₃ | H |
| 1.84. | CN | 1-(CH₃)-Cyclopropyl | H | R | H | H |

TABLE-continued

| | | | | | | |
|---|---|---|---|---|---|---|
| 1.85. | CN | 1-(4-(CH$_3$)Ph)-Cyclopropyl | H | R | H | H |
| 1.86. | CN | 1-(2,4-Cl-Ph)-Cyclopropyl | H | R | H | H |
| 1.87. | I | H | H | rac | CH$_3$ | H |
| 1.88. | H | CH$_2$OCH$_3$ | H | R | CH$_3$ | H |
| 1.89. | C(=O)NH$_2$ | CH$_2$OCH$_3$ | H | R | CH$_3$ | H |
| 1.90. | H | OCH$_3$ | H | R | CH$_3$ | H |
| 1.91. | H | N(CH$_3$)$_2$ | H | R | CH$_3$ | H |
| 1.92. | H | OCH$_2$C≡CH | H | R | CH$_3$ | H |
| 1.93. | CN | 1-(CH$_3$)-Cyclopropyl | H | R | CH$_3$ | H |
| 1.94. | CN | 1-(2,4-Cl-Ph-Cyclopropyl | H | R | CH$_3$ | H |
| 1.95. | CN | H | H | R | CH$_2$CH$_3$ | H |
| 1.96. | CN | CH$_3$ | H | R | CH$_2$CH$_3$ | H |
| 1.97. | Br | H | H | R | H | H |
| 1.98. | C≡C—Si(CH$_3$)$_3$ | H | H | R | CH$_3$ | H |
| 1.99. | CN | 2-F-Ph | H | R | H | H |
| 1.100. | H | H | H | R | H | H |
| 1.101. | CH$_3$ | H | H | R | H | H |
| 1.102. | H | H | H | R | H | H |
| 1.103. | CH$_3$ | H | H | R | H | H |
| 1.104. | CN | 2-F-Ph | H | R | CH$_3$ | H |
| 1.105. | Cl | H | H | R | CH$_3$ | H |
| 1.106. | Cl | H | H | R | H | H |
| 1.107. | CF$_3$ | H | H | R | CH$_3$ | H |
| 1.108. | CF$_3$ | H | H | R | H | H |
| 1.109. | H | CF$_3$ | H | R | CH$_3$ | H |
| 1.110. | Br | CH$_3$ | H | R | CH$_3$ | H |
| 1.111. | Br | CH$_3$ | H | R | H | H |
| 1.112. | CH$_3$ | CH$_3$ | H | R | CH$_3$ | H |
| 1.113. | CH$_3$ | CH$_3$ | H | R | H | H |
| 1.114. | CF$_3$ | CH$_3$ | H | R | H | H |
| 1.115. | CF$_3$ | CH$_3$ | H | R | CH$_3$ | H |
| 1.116. | C≡CH | H | H | R | H | H |
| 1.117. | C≡C—Si(CH$_3$)$_3$ | H | H | R | CH$_3$ | H |
| 1.118. | H | C(=O)OCH$_3$ | H | R | CH$_3$ | H |
| 1.119. | C≡CH | H | H | R | CH$_3$ | H |
| 1.120. | NO$_2$ | CH$_3$ | H | R | CH$_3$ | H |
| 1.121. | NO$_2$ | CH$_3$ | H | rac | H | H |
| 1.122. | NO$_2$ | CH$_3$ | H | S | H | H |
| 1.123. | NO$_2$ | CH$_3$ | H | R | H | H |
| 1.124. | NO$_2$ | CH$_3$ | H | rac | H | H |
| 1.125. | NO$_2$ | CH$_3$ | H | rac | CH$_3$ | H |
| 1.126. | NO$_2$ | CH$_3$ | H | R | CH$_2$CH$_3$ | H |
| 1.127. | CN | CH$_3$ | H | rac | H | H |
| 1.128. | CN | H | H | rac | H | H |
| 1.129. | CN | H | H | R | CH$_2$CH$_3$ | H |
| 1.130. | CN | CH$_2$CH$_3$ | H | R | CH$_2$CH$_3$ | H |
| 1.131. | CN | CH(CH$_3$)$_2$ | H | R | CH$_2$CH$_3$ | H |
| 1.132. | Cl | Cyclopropyl | H | S | H | H |
| 1.133. | Cl | 4-F-Ph | H | R | H | H |
| 1.134. | Cl | CF$_3$ | H | S | H | H |
| 1.135. | Cl | CF$_3$ | H | R | CH$_3$ | H |
| 1.136. | H | CF$_3$ | H | S | H | H |
| 1.137. | H | 4-Cl-Ph | H | S | H | H |
| 1.138. | Cl | 4-Cl-Ph | H | rac | H | H |
| 1.139. | Br | CF$_3$ | H | rac | H | H |
| 1.140. | H | C(=O)NHCH$_3$ | H | R | CH$_3$ | H |
| 1.141. | CN | H | H | R | CH$_3$ | H |
| 1.142. | CN | CH$_3$ | H | R | CH$_3$ | H |
| 1.143. | CN | CF$_3$ | H | R | CH$_3$ | H |
| 1.144. | CN | CF$_2$H | H | R | CH$_3$ | H |
| 1.145. | CN | CF$_2$H | H | R | CH$_3$ | H |
| 1.146. | CN | CF$_2$H | H | R | CH$_3$ | H |
| 1.147. | CN | CF$_3$ | H | R | CH$_3$ | H |
| 1.148. | CN | CF$_2$H | H | R | CH$_3$ | H |
| 1.149. | CN | CF$_3$ | H | R | H | H |
| 1.150. | CN | CF$_2$H | H | rac | H | H |
| 1.151. | Cl | CF$_3$ | H | rac | H | H |
| 1.152. | Cl | CF$_3$ | H | rac | H | H |
| 1.153. | Cl | CF$_3$ | H | rac | H | H |
| 1.154. | CH$_3$ | CF$_3$ | H | rac | H | H |
| 1.155. | CH$_3$ | CF$_3$ | H | rac | H | H |
| 1.156. | CN | H | CH$_3$ | rac | H | H |
| 1.157. | CN | H | CH$_3$ | rac | H | H |
| 1.158. | CN | CH$_2$CH$_3$ | CH$_3$ | rac | H | H |
| 1.159. | CN | CH$_3$ | H | R | CH$_3$ | H |
| 1.160. | CN | CH$_2$CH$_3$ | H | R | CH$_3$ | H |

TABLE-continued

| | | | | | | |
|---|---|---|---|---|---|---|
| 1.161. | CN | CH(CH$_3$)$_2$ | H | R | CH$_3$ | H |
| 1.162. | Cl | CH$_2$CH$_3$ | H | R | CH$_3$ | H |
| 1.163. | Cl | CH$_3$ | H | R | CH$_3$ | H |
| 1.164. | Cl | CH(CH$_3$)$_2$ | H | R | CH$_3$ | H |
| 1.165. | Cl | CH(CH$_3$)$_2$ | H | R | CH$_3$ | H |
| 1.166. | CH$_3$ | CF$_2$H | H | rac | H | H |
| 1.167. | Cl | CF$_2$H | H | rac | H | H |
| 1.168. | Cl | CClF$_2$ | H | rac | H | H |
| 1.169. | Cl | CF$_3$ | H | rac | H | H |
| 1.170. | Cl | CF$_2$H | H | rac | H | H |
| 1.171. | Cl | CF$_2$H | H | rac | H | H |
| 1.172. | CH$_3$ | CClF$_2$ | H | rac | H | H |
| 1.173. | CH$_3$ | CClF$_2$ | H | rac | H | H |
| 1.174. | CH$_3$ | CF$_2$H | H | rac | H | H |
| 1.175. | CN | CF$_2$H | H | rac | H | H |
| 1.176. | Cl | CF$_2$H | H | rac | H | H |
| 1.177. | CN | H | H | rac | H | H |
| 1.178. | CN | CH$_3$ | H | rac | H | H |
| 1.179. | CN | CH(CH$_3$)$_2$ | H | rac | H | H |
| 1.180. | CN | Cyclopropyl | H | rac | H | H |
| 1.181. | CN | 1-CH$_3$-Cyclopropyl | H | rac | H | H |
| 1.182. | CN | 1-CH$_3$-Cyclopropyl | H | rac | H | H |
| 1.183. | CN | 1-CH$_3$-Cyclopropyl | H | rac | H | H |
| 1.184. | C(=O)—CH$_3$ | H | H | R | CH$_3$ | H |
| 1.185. | C(=O)—CH$_2$—CH$_3$ | H | H | R | CH$_3$ | H |
| 1.186. | C(=O)—CH$_3$ | H | H | R | H | H |
| 1.187. | C(=O)—CH$_3$ | CH$_3$ | H | R | H | H |
| 1.188. | C(=O)—CH$_3$ | CF$_3$ | H | R | CH$_3$ | H |
| 1.189. | C(=O)—CH$_3$ | CF$_2$H | H | R | CH$_3$ | H |
| 1.190. | C≡CH | CF$_3$ | H | R | CH$_3$ | H |
| 1.191. | C≡CH | CF$_2$H | H | R | CH$_3$ | H |
| 1.192. | C(=O)—CH$_3$ | CF$_3$ | H | R | H | H |
| 1.193. | C(=O)—CH$_3$ | CF$_2$H | H | R | H | H |
| 1.194. | H | CN | H | R | CH$_3$ | H |
| 1.195. | Cl | CN | H | R | CH$_3$ | H |
| 1.196. | Br | CN | H | R | CH$_3$ | H |
| 1.197. | I | CN | H | R | CH$_3$ | H |
| 1.198. | C≡CH | CN | H | R | CH$_3$ | H |
| 1.199. | C(=O)—CH$_3$ | CN | H | R | CH$_3$ | H |
| 1.200. | H | CN | H | R | H | H |
| 1.201. | CH$_3$ | CN | H | R | H | H |
| 1.202. | Cl | CN | H | R | H | H |
| 1.203. | Br | CN | H | R | H | H |
| 1.204. | I | CN | H | R | H | H |
| 1.205. | C≡CCH$_3$ | CN | H | R | H | H |
| 1.206. | H | C(=O)NH$_2$ | H | R | H | H |
| 1.207. | H | CN | H | R | H | H |
| 1.208. | H | CN | H | rac | H | H |
| 1.209. | H | CN | H | rac | H | H |
| 1.210. | H | CN | H | rac | H | H |
| 1.211. | H | CN | H | rac | H | H |
| 1.212. | H | C(=O)OCH$_3$ | H | rac | H | H |
| 1.213. | H | C(=O)OCH$_2$CH$_3$ | H | rac | H | H |
| 1.214. | H | CF$_3$ | H | R | CH$_3$ | H |
| 1.215. | H | CF$_3$ | H | R | H | H |
| 1.216. | CN | H | H | rac | H | H |
| 1.217. | CN | CH$_3$ | H | rac | H | H |
| 1.218. | CN | CH$_2$CH$_3$ | H | rac | H | H |
| 1.219. | OCH$_3$ | H | H | R | CH$_3$ | H |
| 1.220. | OCH$_3$ | H | H | R | H | H |
| 1.221. | C≡C-(3-OCH$_3$)-Ph | H | H | R | CH$_3$ | H |
| 1.222. | CC—CH$_2$OH | H | H | R | CH$_3$ | H |
| 1.223. | CN | H | CH$_3$ | rac | H | H |
| 1.224. | CN | CH$_3$ | CH$_3$ | rac | H | H |
| 1.225. | C(=S)NH$_2$ | CH$_3$ | H | R | CH$_3$ | H |
| 1.226. | C(=S)-1-Morpholinyl | CH$_3$ | H | R | CH$_3$ | H |
| 1.227. | SCH$_3$ | CH$_3$ | H | R | CH$_3$ | H |
| 1.228. | S(=O)CH$_3$ | CH$_3$ | H | R | CH$_3$ | H |
| 1.229. | S(=O)$_2$CH$_3$ | CH$_3$ | H | R | CH$_3$ | H |
| 1.230. | S(=O)$_2$CH$_3$ | CH$_3$ | H | R | H | H |
| 1.231. | S(=O)CH$_3$ | CH$_3$ | H | R | H | H |
| 1.232. | SCH$_3$ | CH$_3$ | H | R | H | H |
| 1.233. | C(=O)CH$_3$ | CH$_3$ | H | R | H | H |
| 1.234. | C≡CH | CH$_3$ | H | R | H | H |
| 1.235. | C≡C—C(CH$_3$)$_3$ | CH$_3$ | H | R | H | H |

TABLE-continued

| | | | | | | | |
|---|---|---|---|---|---|---|---|
| 1.236. | C≡C—Si(CH₃)₃ | CH₃ | H | R | H | H | |
| 1.237. | CF₃ | H | H | R | H | H | |
| 1.238. | CF₃ | H | H | rac | H | H | |
| 1.239. | CF₃ | H | H | rac | H | H | |
| 1.240. | CF₃ | H | H | rac | H | H | |
| 1.241. | CF₃ | H | H | rac | H | H | |
| 1.242. | C≡C—CH(OH)—CH₂CH₃ | CH₃ | H | R | CH₃ | H | |
| 1.243. | CF₃ | H | H | rac | CH₃ | H | |
| 1.244. | CF₃ | H | H | rac | CH₃ | H | |
| 1.245. | CF₃ | H | H | rac | H | H | |
| 1.246. | C≡C-4-(2-CH₃)-thiazole | H | H | R | CH₃ | H | |
| 1.247. | C≡C-(3CF₃)Ph | H | H | R | CH₃ | H | |
| 1.248. | C≡C-(3Cl,4F)Ph | H | H | R | CH₃ | H | |
| 1.249. | C≡C—CH₂—CH(CH₃)₂ | H | H | R | CH₃ | H | |
| 1.250. | C(=O)CH₂CH₂CH—(CH₃)₂ | H | H | R | CH₃ | H | |
| 1.251. | C≡C—CH(OH)—CH₂CH₃ | H | H | R | CH₃ | H | |
| 1.252. | C≡C—CH₂—O—C(=O)CH₃ | H | H | R | CH₃ | H | |
| 1.253. | CF₃ | H | H | rac | H | H | |
| 1.254. | CF₃ | H | H | rac | H | H | |
| 1.255. | C(=O)—O-cyclohexyl | CH₃ | H | R | H | H | |
| 1.256. | C≡CCH₂OH | H | H | R | H | H | |
| 1.257. | CF₃ | H | H | S | OH | H | |
| 1.258. | CF₃ | H | H | S | OH | H | |
| 1.259. | CF₃ | H | H | S | OCH₃ | H | |
| 1.260. | CF₃ | H | H | S | OCH₃ | H | |
| 1.261. | I | H | H | R | CH₃ | H | |
| 1.262. | CF₃ | H | H | R | CH₃ | H | |
| 1.263. | CF₃ | H | H | R | H | H | |
| 1.264. | CN | H | H | R | H | H | |
| 1.265. | CN | H | H | R | CH₃ | H | |
| 1.266. | CN | CH₃ | H | R | CH₃ | H | |
| 1.267. | CN | CH₃ | H | R | H | H | |
| 1.268. | C(=O)CH₃ | H | H | R | CH₃ | H | |
| 1.269. | C(=O)CH₃ | CH₃ | H | R | CH₃ | H | |
| 1.270. | C(=O)CH₃ | CH₃ | H | R | H | H | |
| 1.271. | CN | H | H | rac | H | H | |

| | Stereo R⁴, R⁵ | R⁶ | R⁷ | Stereo R⁶, R⁷ | R⁸ | R⁹ | R¹⁰ | R¹¹ | X |
|---|---|---|---|---|---|---|---|---|---|
| 1.1. | | H | H | | CH₃ | H | CH₃ | H | —CH₂— |
| 1.2. | | H | H | | H | H | CH₃ | H | —O— |
| 1.3. | | H | H | | H | H | CH₂CH₃ | H | —O— |
| 1.4. | | H | H | | CH₃ | H | CH₃ | H | —CH₂— |
| 1.5. | | H | H | | H | H | CH₃ | H | —O— |
| 1.6. | | H | H | | H | H | CH₂CH₃ | H | —O— |
| 1.7. | | H | H | | CH₃ | H | CH₃ | H | —CH₂— |
| 1.8. | rac | H | H | | H | H | CH₃ | H | — |
| 1.9. | | H | H | | CH₃ | H | CH₃ | H | —CH₂— |
| 1.10. | | H | H | | H | H | CH₃ | H | —O— |
| 1.11. | | H | H | | H | H | CH₂CH₃ | H | —O— |
| 1.12. | | H | H | | CH₃ | H | CH₃ | H | —CH₂— |
| 1.13. | | H | H | | H | H | CH₃ | H | —O— |
| 1.14. | | H | H | | H | H | CH₂CH₃ | H | —O— |
| 1.15. | | H | H | | CH₃ | H | CH₃ | H | —CH₂— |
| 1.16. | rac | H | H | | H | H | CH₃ | H | — |
| 1.17. | S | H | H | | H | H | CH₃ | H | — |
| 1.18. | | H | H | | H | H | H | H | —CH₂— |
| 1.19. | | H | H | | H | H | H | H | —CH₂— |
| 1.20. | | H | H | | H | H | H | H | —CH₂— |
| 1.21. | | H | H | | H | H | H | H | —CH₂— |
| 1.22. | | H | H | | H | H | H | H | —CH₂— |
| 1.23. | rac | H | H | | H | H | H | H | — |
| 1.24. | | H | H | | H | H | H | H | — |
| 1.25. | | H | H | | H | H | H | H | —O— |
| 1.26. | | H | H | | F | H | H | H | —O— |
| 1.27. | | H | H | | H | H | CH(CH₃)₂ | H | —O— |
| 1.28. | | H | H | | H | H | CH(CH₃)₂ | H | — |
| 1.29. | | H | H | | H | H | H | H | —CH₂— |
| 1.30. | | H | H | | H | H | H | H | —CH₂— |
| 1.31. | | H | H | | H | H | H | H | —CH₂— |
| 1.32. | | H | H | | H | H | H | H | —CH₂— |
| 1.33. | | H | H | | H | H | CH₃ | H | —CH₂— |
| 1.34. | | H | H | | H | H | H | H | —CH₂— |
| 1.35. | S | H | H | | H | H | CH₃ | H | — |
| 1.36. | S | H | H | | H | H | CH₃ | H | — |
| 1.37. | | H | H | | H | H | H | H | —CH₂— |
| 1.38. | S | H | H | | H | H | CH₃ | H | — |

TABLE-continued

| | | | | | | | | |
|---|---|---|---|---|---|---|---|---|
| 1.39. | | H | H | H | H | H | H | —CH$_2$— |
| 1.40. | | H | H | H | H | H | H | —CH$_2$— |
| 1.41. | S | H | H | H | H | CH$_3$ | H | — |
| 1.42. | | H | H | H | H | H | H | —CH$_2$— |
| 1.43. | | H | H | H | H | H | H | —CH$_2$— |
| 1.44. | | H | H | H | H | H | H | — |
| 1.45. | | H | H | H | H | CH$_3$ | H | — |
| 1.46. | S | H | H | H | H | CH$_3$ | H | — |
| 1.47. | S | H | H | H | H | CH$_3$ | H | — |
| 1.48. | S | H | H | H | H | CH$_3$ | H | — |
| 1.49. | S | H | H | H | H | CH$_3$ | H | — |
| 1.50. | S | H | H | H | H | CH$_3$ | H | — |
| 1.51. | S | H | H | H | H | CH$_3$ | H | — |
| 1.52. | S | H | H | H | H | H | H | — |
| 1.53. | | H | H | H | H | H | H | — |
| 1.54. | | H | H | H | H | H | H | —CH$_2$— |
| 1.55. | | H | H | H | H | H | H | —O— |
| 1.56. | S | H | H | H | H | CH$_3$ | H | — |
| 1.57. | S | H | H | H | H | CH$_3$ | H | — |
| 1.58. | S | H | H | H | H | CH$_3$ | H | — |
| 1.59. | S | H | H | H | H | CH$_3$ | H | — |
| 1.60. | S | H | H | H | H | CH$_3$ | H | — |
| 1.61. | S | H | H | H | H | CH$_3$ | H | — |
| 1.62. | | H | H | H | H | H | H | — |
| 1.63. | | H | H | H | H | H | H | —CH$_2$— |
| 1.64. | S | H | H | H | H | CH$_3$ | H | — |
| 1.65. | | H | H | H | H | H | H | — |
| 1.66. | | H | H | H | H | H | H | —CH$_2$— |
| 1.67. | S | H | H | H | H | CH$_3$ | H | — |
| 1.68. | S | H | H | H | H | CH$_3$ | H | — |
| 1.69. | S | H | H | H | H | H | H | — |
| 1.70. | | H | H | H | H | CH$_3$ | H | — |
| 1.71. | | H | H | H | H | H | H | —O— |
| 1.72. | | H | H | H | H | CH$_2$CH$_3$ | H | —O— |
| 1.73. | | H | H | H | H | H | H | — |
| 1.74. | | H | H | H | H | H | H | — |
| 1.75. | S | H | H | H | H | CH$_3$ | H | — |
| 1.76. | | H | H | H | H | H | H | —CH$_2$— |
| 1.77. | S | H | H | H | H | CH$_3$ | H | — |
| 1.78. | | H | H | H | H | H | H | —CH$_2$— |
| 1.79. | | H | H | H | H | H | H | — |
| 1.80. | S | H | H | H | H | CH$_3$ | H | — |
| 1.81. | | H | H | H | H | H | H | —CH$_2$— |
| 1.82. | | H | H | H | H | H | H | — |
| 1.83. | S | H | H | H | H | CH$_3$ | H | — |
| 1.84. | | H | H | H | H | H | H | —CH$_2$— |
| 1.85. | | H | H | H | H | H | H | —CH$_2$— |
| 1.86. | | H | H | H | H | H | H | —CH$_2$— |
| 1.87. | S | H | H | H | H | CH$_3$ | H | — |
| 1.88. | | H | H | H | H | CH$_3$ | H | — |
| 1.89. | S | H | H | H | H | CH$_3$ | H | — |
| 1.90. | S | H | H | H | H | CH$_3$ | H | — |
| 1.91. | S | H | H | H | H | CH$_3$ | H | — |
| 1.92. | | H | H | H | H | CH$_3$ | H | — |
| 1.93. | | H | H | H | H | CH$_3$ | H | — |
| 1.94. | S | H | H | H | H | CH$_3$ | H | — |
| 1.95. | | H | H | H | H | CH$_3$ | H | — |
| 1.96. | S | H | H | H | H | CH$_3$ | H | — |
| 1.97. | | H | H | H | H | H | H | —CH$_2$— |
| 1.98. | S | H | H | H | H | CH$_3$ | H | — |
| 1.99. | | H | H | H | H | H | H | —CH$_2$— |
| 1.100. | | H | H | H | H | H | H | —CH$_2$— |
| 1.101. | | H | H | H | H | H | H | —CH$_2$— |
| 1.102. | | H | H | H | H | H | H | — |
| 1.103. | | H | H | H | H | H | H | — |
| 1.104. | S | H | H | H | H | CH$_3$ | H | — |
| 1.105. | S | H | H | H | H | CH$_3$ | H | — |
| 1.106. | | H | H | H | H | H | H | —CH$_2$— |
| 1.107. | S | H | H | H | H | CH$_3$ | H | — |
| 1.108. | | H | H | H | H | H | H | —CH$_2$— |
| 1.109. | S | H | H | H | H | CH$_3$ | H | — |
| 1.110. | S | H | H | H | H | CH$_3$ | H | — |
| 1.111. | | H | H | H | H | H | H | —CH$_2$— |
| 1.112. | S | H | H | H | H | CH$_3$ | H | — |
| 1.113. | | H | H | H | H | H | H | —CH$_2$— |
| 1.114. | | H | H | H | H | H | H | —CH$_2$— |
| 1.115. | S | H | H | H | H | CH$_3$ | H | — |
| 1.116. | | H | H | H | H | H | H | —CH$_2$— |
| 1.117. | S | H | H | H | H | F | H | — |
| 1.118. | S | H | H | H | H | CH$_3$ | H | — |

TABLE-continued

| | | | | | | | | |
|---|---|---|---|---|---|---|---|---|
| 1.119. | S | H | H | | H | H | $CH_3$ | H | — |
| 1.120. | S | H | H | | H | H | $CH_3$ | H | — |
| 1.121. | | H | H | | H | H | H | H | —O— |
| 1.122. | | H | H | | H | H | H | H | — |
| 1.123. | | H | H | | H | H | H | H | — |
| 1.124. | | H | H | | H | H | H | H | —$CH_2$— |
| 1.125. | rac | H | H | | H | H | H | H | — |
| 1.126. | S | H | H | | H | H | H | H | — |
| 1.127. | rac | $CH_3$ | H | rac | H | H | H | H | — |
| 1.128. | rac | $CH_3$ | H | rac | H | H | H | H | — |
| 1.129. | S | H | H | | H | H | H | H | — |
| 1.130. | S | H | H | | H | H | H | H | — |
| 1.131. | S | H | H | | H | H | H | H | — |
| 1.132. | | H | H | | H | H | H | H | —$CH_2$— |
| 1.133. | | H | H | | H | H | H | H | —$CH_2$— |
| 1.134. | | H | H | | H | H | H | H | —$CH_2$— |
| 1.135. | S | H | H | | H | H | $CH_3$ | H | — |
| 1.136. | | H | H | | H | H | H | H | —$CH_2$— |
| 1.137. | | H | H | | H | H | H | H | —$CH_2$— |
| 1.138. | | H | H | | H | H | H | H | —$CH_2$— |
| 1.139. | | H | H | | H | H | H | H | —$CH_2$— |
| 1.140. | S | H | H | | H | H | $CH_3$ | H | — |
| 1.141. | rac | H | H | | H | H | Cl | H | — |
| 1.142. | S | H | H | | H | H | Cl | H | — |
| 1.143. | S | H | H | | H | H | Cl | H | — |
| 1.144. | S | H | H | | H | H | CN | H | — |
| 1.145. | S | H | H | | H | H | $CH_2CH_3$ | H | — |
| 1.146. | S | H | H | | H | H | $OCH_3$ | H | — |
| 1.147. | S | H | H | | H | H | $OCH_2CH_3$ | H | — |
| 1.148. | S | H | H | | $CH_3$ | H | $CH_3$ | H | — |
| 1.149. | | H | H | | F | H | H | H | —O— |
| 1.150. | | H | H | | $CH_3$ | H | H | H | —O— |
| 1.151. | | H | H | | $CH_3$ | H | H | H | —O— |
| 1.152. | | H | H | | F | H | $CH_3$ | H | —O— |
| 1.153. | | H | H | | $CH_3$ | H | H | $CH_3$ | —O— |
| 1.154. | | H | H | | F | H | $CH_3$ | H | —O— |
| 1.155. | | H | H | | H | H | H | H | —O— |
| 1.156. | | H | H | | H | H | H | H | —O— |
| 1.157. | | H | H | | H | H | H | H | — |
| 1.158. | | H | H | | H | H | H | H | — |
| 1.159. | S | H | H | | $CH_3$ | H | Cl | H | — |
| 1.160. | S | H | H | | H | H | Cl | H | — |
| 1.161. | S | H | H | | H | H | Cl | H | — |
| 1.162. | S | H | H | | H | H | Cl | H | — |
| 1.163. | S | H | H | | H | H | Cl | H | — |
| 1.164. | S | H | H | | H | H | Cl | H | — |
| 1.165. | S | H | H | | H | H | $CH_3$ | H | — |
| 1.166. | | H | H | | H | H | $CH_3$ | H | —$CH_2$— |
| 1.167. | | H | H | | H | H | $CH_3$ | H | —$CH_2$— |
| 1.168. | | H | H | | H | H | $CH_3$ | H | —$CH_2$— |
| 1.169. | | H | H | | H | H | $CH_3$ | H | —$CH_2$— |
| 1.170. | | H | H | | H | H | $OCH_3$ | H | —$CH_2$— |
| 1.171. | | H | H | | H | H | $OCH_2CH_3$ | H | —$CH_2$— |
| 1.172. | | H | H | | H | H | $OCH_2CH_3$ | H | —$CH_2$— |
| 1.173. | | H | H | | $OCH_3$ | H | H | H | —$CH_2$— |
| 1.174. | | H | H | | H | H | $OCH_2CH_3$ | H | —O— |
| 1.175. | | H | H | | H | H | $OCH_2CH_3$ | H | —O— |
| 1.176. | | H | H | | H | H | $OCH_2CH_3$ | H | —O— |
| 1.177. | | H | H | | H | H | $OCH_3$ | H | —O— |
| 1.178. | | H | H | | H | H | $OCH_2CH_3$ | H | —O— |
| 1.179. | | H | H | | H | H | $OCH_3$ | H | —O— |
| 1.180. | | H | H | | H | H | $OCH_3$ | H | —O— |
| 1.181. | | H | H | | H | H | $OCH_3$ | H | —O— |
| 1.182. | | H | H | | H | H | H | H | —O— |
| 1.183. | | H | H | | H | H | $CH_3$ | H | —$CH_2$— |
| 1.184. | S | H | H | | H | H | $CH_3$ | H | — |
| 1.185. | S | H | H | | H | H | $CH_3$ | H | — |
| 1.186. | | H | H | | H | H | H | H | —$CH_2$— |
| 1.187. | | H | H | | H | H | H | H | — |
| 1.188. | S | H | H | | H | H | $CH_3$ | H | — |
| 1.189. | | H | H | | H | H | $CH_3$ | H | — |
| 1.190. | S | H | H | | H | H | $CH_3$ | H | — |
| 1.191. | S | H | H | | H | H | $CH_3$ | H | — |
| 1.192. | | H | H | | H | H | H | H | —$CH_2$— |
| 1.193. | | H | H | | H | H | H | H | —$CH_2$— |
| 1.194. | S | H | H | | H | H | $CH_3$ | H | — |
| 1.195. | S | H | H | | H | H | $CH_3$ | H | — |
| 1.196. | S | H | H | | H | H | $CH_3$ | H | — |
| 1.197. | S | H | H | | H | H | $CH_3$ | H | — |
| 1.198. | S | H | H | | H | H | $CH_3$ | H | — |

TABLE-continued

| No. | | | | | | | | |
|---|---|---|---|---|---|---|---|---|
| 1.199. | S | H | H | H | H | CH₃ | H | — |
| 1.200. |   | H | H | H | H | H | H | —CH₂— |
| 1.201. |   | H | H | H | H | H | H | —CH₂— |
| 1.202. |   | H | H | H | H | H | H | —CH₂— |
| 1.203. |   | H | H | H | H | H | H | —CH₂— |
| 1.204. |   | H | H | H | H | H | H | —CH₂— |
| 1.205. |   | H | H | H | H | H | H | —CH₂— |
| 1.206. |   | H | H | H | H | H | H | —CH₂— |
| 1.207. |   | H | H | H | H | H | H | —O— |
| 1.208. |   | H | H | CH₃ | H | H | H | —O— |
| 1.209. |   | H | H | CH₃ | H | CH₃ | H | —O— |
| 1.210. |   | H | H | F | H | CH₃ | H | —O— |
| 1.211. |   | H | H | CH₃ | H | H | CH₃ | —O— |
| 1.212. |   | H | H | H | H | H | H | —CH₂— |
| 1.213. |   | H | H | H | H | H | H | —CH₂— |
| 1.214. | S | H | H | H | H | CH₃ | H | — |
| 1.215. |   | H | H | H | H | H | H | —CH₂— |
| 1.216. |   | H | H | H | Cl | H | H | — |
| 1.217. |   | H | H | H | Cl | H | H | — |
| 1.218. |   | H | H | H | Cl | H | H | — |
| 1.219. | S | H | H | H | H | CH₃ | H | — |
| 1.220. |   | H | H | H | H | H | H | —CH₂— |
| 1.221. | S | H | H | H | H | CH₃ | H | — |
| 1.222. | S | H | H | H | H | CH₃ | H | — |
| 1.223. |   | H | H | H | H | H | H | —CH₂— |
| 1.224. |   | H | H | H | H | H | H | —CH₂— |
| 1.225. | S | H | H | H | H | CH₃ | H | — |
| 1.226. | S | H | H | H | H | CH₃ | H | — |
| 1.227. | S | H | H | H | H | CH₃ | H | — |
| 1.228. | S | H | H | H | H | CH₃ | H | — |
| 1.229. | S | H | H | H | H | CH₃ | H | — |
| 1.230. |   | H | H | H | H | H | H | —CH₂— |
| 1.231. |   | H | H | H | H | H | H | —CH₂— |
| 1.232. |   | H | H | H | H | H | H | —CH₂— |
| 1.233. |   | H | H | H | H | H | H | —CH₂— |
| 1.234. |   | H | H | H | H | H | H | —CH₂— |
| 1.235. |   | H | H | H | H | H | H | —CH₂— |
| 1.236. |   | H | H | H | H | H | H | —CH₂— |
| 1.237. |   | H | H | H | H | H | H | — |
| 1.238. |   | H | H | H | H | CH₂CH₃ | H | —O— |
| 1.239. |   | H | H | H | H | OCH₃ | H | —O— |
| 1.240. |   | H | H | H | H | OCH₃ | H | —CH₂— |
| 1.241. |   | CH₃ | CH₃ | H | Cl | F | H | —O— |
| 1.242. | S | H | H | H | H | CH₃ | H | — |
| 1.243. | rac | H | H | H | H | F | H | — |
| 1.244. | rac | H | H | H | H | Cl | H | — |
| 1.245. |   | H | H | H | H | Cl | H | — |
| 1.246. | S | H | H | H | H | CH₃ | H | — |
| 1.247. | S | H | H | H | H | CH₃ | H | — |
| 1.248. | S | H | H | H | H | CH₃ | H | — |
| 1.249. | S | H | H | H | H | CH₃ | H | — |
| 1.250. | S | H | H | H | H | CH₃ | H | — |
| 1.251. | S | H | H | H | H | CH₃ | H | — |
| 1.252. | S | H | H | H | H | CH₃ | H | — |
| 1.253. |   | H | H | H | OCH₃ | H | H | —CH₂— |
| 1.254. |   | H | H | CH₃ | H | H | H | — |
| 1.255. |   | H | H | H | H | H | H | —CH₂— |
| 1.256. |   | H | H | H | H | H | H | —CH₂— |
| 1.257. | S | H | H | H | H | H | H | — |
| 1.258. | R | H | H | H | H | H | H | — |
| 1.259. | S | H | H | H | H | H | H | — |
| 1.260. | R | H | H | H | H | H | H | — |
| 1.261. | S | H | H | H | H | CH₃ | H | — |
| 1.262. | S | H | H | H | H | CH₃ | H | — |
| 1.263. |   | H | H | H | H | H | H | —CH₂— |
| 1.264. |   | H | H | H | H | H | H | —CH₂— |
| 1.265. | S | H | H | H | H | CH₃ | H | — |
| 1.266. | S | H | H | H | H | CH₃ | H | — |
| 1.267. |   | H | H | H | H | H | H | —CH₂— |
| 1.268. | S | H | H | H | H | CH₃ | H | — |
| 1.269. | S | H | H | H | H | CH₃ | H | — |
| 1.270. |   | H | H | H | H | H | H | —CH₂— |
| 1.271. |   | H | H | CH₃ | H | CH₃ | H | —CH₂— |

The compounds 1.261 to 1.270 are each in the form of their hydrochlorides.

The present invention further provides processes for the preparation of corresponding compounds of the formula (I) and/or their salts and/or their agrochemically compatible quaternized nitrogen derivatives:

a.) for the preparation of compounds of the formula (I)

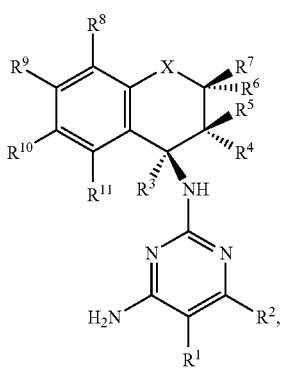
(I)

in which the radicals $R^1$ to $R^{11}$ and X have the above meanings, it is possible to react a compound of the formula (II)

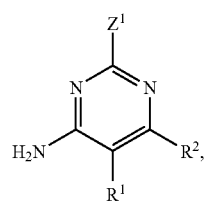
(II)

in which $R^1$ and $R^2$ have the above meaning and $Z^1$ is an exchangeable radical or a leaving group, such as in particular chlorine, trichloromethyl, $(C_1$-$C_4)$-alkylsulfonyl, unsubstituted or substituted phenyl-$(C_1$-$C_4)$-alkylsulfonyl or $(C_1$-$C_4)$-alkylphenylsulfonyl, with an amine of the formula (III) or an acid addition salt thereof.

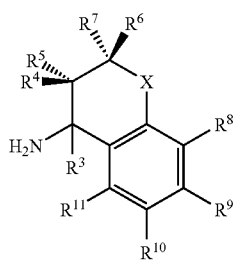
(III)

where the radicals $R^3$ to $R^{11}$ and X have the above meaning.

The compounds of the formula (II) can be obtained for Z=chlorine by reacting compounds of the formula (IV) with ammonia in accordance with the following reaction scheme:

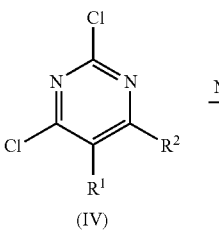
(IV)

NH$_3$ →

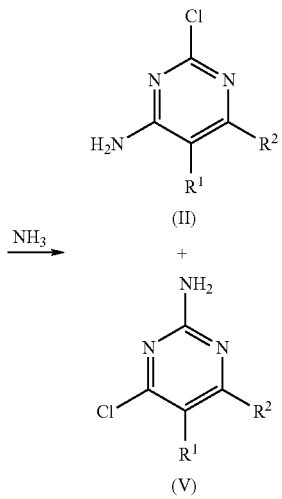
(II)

+

(V)

The resulting isomer mixture of (II) and (V) can be separated by chromatography or be used as a mixture in the subsequent reaction.

The amines of the formula (III) or the acid addition salt thereof are commercially available and their synthesis is described in WO2004/069814 A1.

The pyrimidines of the formula (II) are commercially available, special derivatives can be prepared by known processes. For example, cyanopyrimidines can be prepared from malonodinitrile (H. KRISTINSSON, *J. Chem. Soc., Chem. Commun.*, 1974, 350) or from cyanamide (H. W. SCHMIDT, G. KOITZ, H. JUNEK; *J. Heterocycl. Chem.*, 1987, 24, 1305).

b.) For the preparation of compounds of the formula (I), compounds can be used as precursors and be converted into other compounds according to the invention.

(1) For example, derivatives of the formula (I) where $R^1$, $R^2$ or $R^{10}$=Hal, in particular iodine or bromine, can be reacted with acetylenes or trimethylsilyl-protected acetylene with transition metal catalysis, e.g. with bis(triphenylphosphine)palladium(II) chloride in protic or aprotic solvents and the addition of a base at temperatures between 20 and 150° C. to give compounds of the formula (I) where $R^1$, $R^2$ or $R^{10}$=alkynyl.

(2) For example, derivatives of the formula (I) where $R^1$=CN can be saponified with acidic or basic catalysis and the carboxylic acids obtained in this way can be converted by known processes into acid chlorides and, in turn, these can be converted into amides.

(3) For example, derivatives of the formula (I) where $R^2$=Hal can be converted in protic or aprotic solvents and the addition of a base at temperatures between 100 and 200° C. through reaction with alcoholates or amines to give compounds of the formula (I) where $R^2$=alkoxyalkyl or aminoalkyl or diaminoalkyl.

Collections of compounds of the formula (I) and/or salts thereof which can be synthesized by the aforementioned reactions can also be prepared in a parallel manner, it being possible for this to take place in a manual, partly automated or completely automated manner. In this connection, it is, for example, possible to automate the reaction procedure, the work-up or the purification of the products and/or intermediates. Overall, this is understood as meaning a procedure as described, for example, by D. Tiebes in Combinatorial Chemistry—Synthesis, Analysis, Screening (editor Günther Jung), Verlag Wiley 1999, on pages 1 to 34.

For the parallel reaction procedure and work-up, it is possible to use a series of commercially available instruments, for example Calpyso reaction blocks from Barnstead International, Dubuque, Iowa 52004-0797, USA or reaction stations from Radleys, Shirehill, Saffron Walden, Essex, CB 11 3AZ, England or MultiPROBE Automated Workstations from Perkin Elmer, Waltham, Mass. 02451, USA. For the parallel purification of compounds of the formula (I) and salts thereof or of intermediates produced during the preparation, there are available, inter alia, chromatography apparatuses, for example from ISCO, Inc., 4700 Superior Street, Lincoln, Nebr. 68504, USA.

The apparatuses listed lead to a modular procedure in which the individual process steps are automated, but between the process steps manual operations have to be carried out. This can be circumvented by using partly or completely integrated automation systems in which the respective automation modules are operated, for example, by robots. Automation systems of this type can be acquired, for example, from Caliper, Hopkinton, Mass. 01748, USA.

The implementation of single or several synthesis steps can be supported through the use of polymer-supported reagents/scavenger resins. The specialist literature describes a series of experimental protocols, for example in ChemFiles, Vol. 4, No. 1, Polymer-Supported Scavengers and Reagents for Solution-Phase Synthesis (Sigma-Aldrich).

Besides the methods described here, the preparation of compounds of the formula (I) and salts thereof can take place completely or partially by solid-phase supported methods. For this purpose, individual intermediates or all intermediates in the synthesis or a synthesis adapted for the corresponding procedure are bonded to a synthesis resin. Solid-phase supported synthesis methods are sufficiently described in the specialist literature, e.g. Barry A. Bunin in "The Combinatorial Index", Verlag Academic Press, 1998 and Combinatorial Chemistry—Synthesis, Analysis, Screening (editor Günther Jung), Verlag Wiley, 1999. The use of solid-phase supported synthesis methods permits a series of protocols known in the literature, which again can be carried out manually or in an automated manner. The reactions can be carried out, for example, by means of IRORI technology in microreactors from Nexus Biosystems, 12140 Community Road, Poway, Calif. 92064, USA.

Both on a solid phase and in liquid phase can the procedure of individual or several synthesis steps be supported through the use of microwave technology. The specialist literature describes a series of experimental protocols, for example in Microwaves in Organic and Medicinal Chemistry (editor C. O. Kappe and A. Stadler), Verlag Wiley, 2005.

The preparation according to the process described here produces compounds of the formula (I) and their salts in the form of substance collections which are called libraries. The present invention also provides libraries which comprise at least two compounds of the formula (I) and their salts.

On account of the herbicidal property of the compounds of the formula (I), the invention also further provides the use of the compounds of the formula (I) according to the invention as herbicides for controlling harmful plants.

Herbicides are used in agriculturally utilized crops during various cultivation phases. For example, the application of some products even takes place before or during sowing. Others are applied before the crop plant emerges, i.e. before the seedling breaks through the earth's surface (pre-emergence herbicides). Finally, post-emergence herbicides are used if either already the seed leaves or foliage leaves have been formed by the crop plant.

Here, the compounds according to the invention can be used either pre-emergence or post-emergence, with use of the compounds according to the invention pre-emergence being preferred.

The pre-emergence treatment includes both the treatment of the area under cultivation prior to sowing (ppi=pre plant incorporation), and also the treatment of the sown areas of cultivation which do not yet sustain any growth.

The compounds of the formula (I) according to the invention and their salts, also referred to synonymously below together as compounds of the formula (I), have excellent herbicidal effectiveness in respect of a broad spectrum of economically important monocotyledonous and dicotyledonous harmful plants. Difficult-to-control perennial weeds which produce shoots from rhizomes, root stocks or other perennial organs are also well controlled by the active ingredients. Here, it is unimportant whether the substances are applied in the presowing method, pre-emergence method or post-emergence method.

Specifically, examples which may be mentioned are some of the representatives of the monocotyledonous and dicotyledonous weed flora which can be controlled by the compounds of the formula (I) according to the invention, without a limitation to certain species being intended through the naming.

On the side of the monocotyledonous weed species, e.g. *Agrostis, Alopecurus, Apera, Avena, Brachicaria, Bromus, Dactyloctenium, Digitaria, Echinochloa, Eleocharis, Eleusine, Festuca, Fimbristylis, Ischaemum, Lolium, Monochoria, Panicum, Paspalum, Phalaris, Phleum, Poa, Sagittaria, Scirpus, Setaria, Sphenoclea*, and also *Cyperus* species predominantly from the annual group and on the sides of the perennial species *Agropyron, Cynodon, Imperata* and *Sorghum* and also perennial *Cyperus* species are well controlled.

In the case of dicotyledonous weed species, the spectrum of action extends to species such as, for example, *Galium, Viola, Veronica, Lamium, Stellaria, Amaranthus, Sinapis, Ipomoea, Matricaria, Abutilon* and *Sida* on the annual side, and *Convolvulus, Cirsium, Rumex* and *Artemisia* in the case of the perennial weeds. Moreover, herbicidal effect in the case of dicotyledonous weeds such as *Ambrosia, Anthemis, Carduus, Centaurea, Chenopodium, Cirsium, Convolvulus, Datura, Emex, Galeopsis, Galinsoga, Lepidium, Lindernia, Papaver, Portlaca, Polygonum, Ranunculus, Rorippa, Rotala, Seneceio, Sesbania, Solanum, Sonchus, Taraxacum, Trifolium, Urtica* and *Xanthium* is observed.

If the compounds of the formula (I) according to the invention are applied to the soil surface prior to germination, then the weed seedlings are either prevented completely from emerging, or the weeds grow until they have reached the seed leaf stage, but then their growth stops and, eventually, after three to four weeks have elapsed, they die completely.

If the active ingredients of the formula (I) are applied post-emergence to the green parts of the plants, growth likewise stops drastically a very short time after the treatment and the weed plants remain at the growth stage at the time of application, or they die completely after a certain time, so that in this manner competition by the weeds, which is harmful to the crop plants, is eliminated very early on and in a lasting manner.

Although the compounds of the formula (I) according to the invention have excellent herbicidal activity in respect of monocotyledonous and dicotyledonous weeds, crop plants of economically important crops, such as, for example, wheat, barley, rye, rice, corn, sugarbeet, cotton, rapeseed and soybean, are only damaged negligibly, if at all. For these reasons, the present compounds are very highly suitable for the selective control of undesired plant growth in agricultural useful plantations. Moreover, the substances of the formula (I) according to the invention have excellent growth regulatory properties in crop plants. They intervene in a plant's metabolism in a regulatory fashion and can thus be used for the targeted influencing of plant ingredients and for facilitating harvesting, such as, for example, by triggering desiccation and stunted growth. Moreover, they are also suitable for generally controlling and inhibiting unwanted vegetative growth without destroying the plants in the process. Inhibiting the vegetative growth plays a large role in many monocotyledonous and dicotyledonous crops, allowing lodging to be reduced or prevented completely.

On account of their herbicidal and plant growth regulatory properties, the active ingredients can also be used for controlling harmful plants in crops of known plants or genetically modified plants which are yet to be developed. As a rule, the transgenic plants are distinguished by particular advantageous properties, for example by resistances to certain pesticides, primarily certain herbicides, resistances to plant diseases or pathogens of plant diseases, such as certain insects or microorganisms such as fungi, bacteria or viruses. Other particular properties relate, for example, to the harvested material with respect to quantity, quality, storability, composition and specific ingredients. For example, transgenic plants with increased starch content or modified quality of the starch or those with a different fatty acid composition of the harvested material are known. Further particular properties can lie in a tolerance or resistance to abiotic stress factors, for example heat, cold, drought, salt and ultraviolet radiation.

Preference is given to using the compounds of the formula (I) according to the invention or salts thereof in economically important transgenic crops of useful plants and ornamental plants, for example of cereals such as wheat, barley, rye, oats, millet, rice, manioc and corn, or else crops of sugarbeet, cotton, soybean, rapeseed, potatoes, tomatoes, peas and other vegetable varieties.

Preferably, the compounds of the formula (I) can be used as herbicides in crops of useful plants which are resistant to, or have been rendered genetically resistant to, the phytotoxic actions of the herbicides.

Conventional ways of producing new plants which have modified properties compared to existing plants consist, for example, in classic cultivation methods and the generation of mutants. Alternatively, new plants with modified properties can be produced using genetic engineering methods (see e.g. EP 0221044, EP 0131624). For example, in several cases the following have been described:

genetic modifications of crop plants for the purpose of modifying the starch synthesized in the plants (e.g. WO 92/011376, WO 92/014827, WO 91/019806), transgenic crop plants which are resistant to certain herbicides of the glufosinate type (cf. e.g. EP 0242236, EP 0242246) or of the glyphosate type (WO 92/000377) or of the sulfonylurea type (EP 0257993, U.S. Pat. No. 5,013,659), transgenic crop plants, for example cotton, with the ability to produce *Bacillus thuringiensis* toxins (Bt toxins) which make the plants resistant to certain pests (EP 0142924, EP 0193259), transgenic crop plants with a modified fatty acid composition (WO 91/013972), genetically modified crop plants with new ingredients or secondary substances, e.g. new phytoalexins, which bring about increased resistance to disease (EP 0309862, EP 0464461), genetically modified plants with reduced photorespiration which have higher yields and higher stress tolerance (EP 0305398), transgenic crop plants which produce pharmaceutically or diagnostically important proteins ("molecular pharming"), transgenic crop plants distinguished by higher yields or better quality, transgenic crop plants distinguished by a combination e.g. of the aforementioned new properties ("gene stacking").

Numerous molecular biological techniques with which new transgenic plants with modified properties can be produced are known in principle; see e.g. I. Potrykus and G. Spangenberg (eds.) Gene Transfer to Plants, Springer Lab Manual (1995), Springer Verlag Berlin, Heidelberg or Christou, "Trends in Plant Science" 1 (1996) 423-431.

For such genetic manipulations, nucleic acid molecules which permit a mutagenesis or a sequence modification by recombination of DNA sequences can be introduced into plasmids. For example, with the help of standard methods, it is possible to carry out base exchanges, to remove part sequences or to add natural or synthetic sequences. Adapters or linkers may be added to the fragments in order to link the DNA fragments to one another, see e.g. Sambrook et al., 1989, Molecular Cloning, A Laboratory Manual, $2^{nd}$ edition, Cold Spring Harbor Laboratory Press, Cold Spring Harbor, N.Y.; or Winnacker "Gene and Klone [Genes and Clones]", VCH Weinheim $2^{nd}$ edition 1996.

The preparation of plant cells with reduced activity of a gene product can be achieved, for example, through the expression of at least one corresponding antisense-RNA, a sense-RNA to achieve a cosuppression effect or the expression of at least one correspondingly constructed ribozyme which specifically cleaves transcripts of the aforementioned gene product.

To this end, it is possible to use firstly DNA molecules which encompass the entire coding sequence of a gene product including any flanking sequences which may be present, and also DNA molecules which only encompass parts of the coding sequence, it being necessary for these parts to be long enough to bring about an antisense effect in the cells. Also possible is the use of DNA sequences which have a high degree of homology to the coding sequences of a gene product but are not entirely identical thereto.

During the expression of nucleic acid molecules in plants, the synthesized protein can be localized in any compartment of the plant cell. However, in order to achieve localization in a certain compartment, it is possible, for example, to link the coding region with DNA sequences which ensure localization in a certain compartment. Sequences of this type are known to the person skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The expression of the nucleic acid molecules can also take place in the organelles of the plant cells.

The transgenic plant cells can be regenerated by known techniques to give whole plants. In principle, the transgenic plants may be plants of any desired plant species, i.e. both monocotyledonous and dicotyledonous plants.

Transgenic plants are thus obtainable which have modified properties as a result of overexpression, suppression or inhibition of homologous (=natural) genes or gene sequences, or expression of heterologous (=foreign) genes or gene sequences.

The compounds of the formula (I) according to the invention can preferably be used in transgenic crops which are resistant to growth regulators, such as, for example, dicamba, or to herbicides which inhibit essential plant enzymes, e.g. acetolactate synthases (ALS), EPSP synthases, glutamine synthases (GS) or hydroxyphenylpyruvate dioxygenases (HPPD), or to herbicides from the group of sulfonylureas, glyphosates, glufosinates or benzoylisoxazoles and analogous active ingredients.

When using the active ingredients of the formula (I) according to the invention in transgenic crops, besides the effects against harmful plants that are observed in other crops, effects often arise which are specific to the application in the particular transgenic crop, for example a modified or specifically expanded weed spectrum which can be controlled, modified application rates which can be used for the application, preferably good combinability with the herbicides against which the transgenic crop is resistant, and also influencing of growth and yield of the transgenic crop plants.

The invention therefore also provides the use of the compounds of the formula (I) according to the invention as herbicides for controlling harmful plants in transgenic crop plants.

The compounds of the formula (I) can be formulated in different ways depending on which biological and/or chemical-physical parameters are prescribed. Suitable formulation options are, for example: spray powders (WP), water-soluble powders (SP), water-soluble concentrates, emulsifiable concentrates (EC), emulsions (EW), such as oil-in-water and water-in-oil emulsions, sprayable solutions, suspension concentrates (SC), dispersions based on oil or water, oil-miscible solutions, capsule suspensions (CS), dusting agents (DP), seed dressings, granules for scattering and soil application, granules (GR) in the form of microgranules, spray granules, coated granules and adsorption granules, water-dispersible granules (WG), water-soluble granules (SG), ULV formulations, microcapsules and waxes.

These individual formulation types are known in principle and are described, for example, in: Winnacker-Küchler, "Chemische Technologie [Chemical Technology]", Volume 7, C. Hanser Verlag Munich, 4$^{th}$ edition 1986; Wade van Valkenburg, "Pesticide Formulations", Marcel Dekker, N.Y., 1973; K. Martens, "Spray Drying" Handbook, 3rd Ed. 1979, G. Goodwin Ltd. London.

The necessary formulation auxiliaries such as inert materials, surfactants, solvents and further additives are likewise known and are described, for example, in: Watkins, "Handbook of Insecticide Dust Diluents and Carriers", 2nd Ed., Darland Books, Caldwell N.J., H. v. Olphen, "Introduction to Clay Colloid Chemistry", 2nd Ed., J. Wiley & Sons, N.Y.; C. Marsden, "Solvents Guide", 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte [Surface-active ethylene oxide adducts]", Wiss. Verlagsgesell., Stuttgart 1976; Winnacker-Küchler, "Chemische Technologie [Chemical Technology]", Volume 7, C. Hanser Verlag Munich, 4$^{th}$ edition, 1986.

On the basis of these formulations, it is also possible to prepare combinations with other pesticidally active substances, such as, for example, insecticides, acaricides, herbicides, fungicides, and also with safeners, fertilizers and/or growth regulators, e.g. in the form of a ready mix or as tank mix.

Spray powders are preparations which can be dispersed uniformly in water and which comprise, besides the active ingredient, apart from a diluent or inert substance, also surfactants of ionic and/or nonionic type (wetting agents, dispersants), e.g. polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate and also sodium oleoylmethyltaurate. To prepare the spray powders, the herbicidal active ingredients are finely ground for example in customary apparatus such as hammer mills, blowing mills and air-jet mills and are mixed simultaneously or subsequently with the formulation auxiliaries.

Emulsifiable concentrates are prepared by dissolving the active ingredient in an organic solvent, e.g. butanol, cyclohexanone, dimethylformamide, xylene or else higher-boiling aromatics or hydrocarbons or mixtures of the organic solvents with the addition of one or more surfactants of an ionic and/or nonionic type (emulsifiers). Emulsifiers which can be used are, for example: alkylarylsulfonic calcium salts, such as Ca dodecylbenzenesulfonate, or nonionic emulsifiers, such as fatty acid polyglycol esters, alkylarylpolyglycol ethers, fatty alcohol polyglycol ethers, propylene oxide-ethylene oxide condensation products, alkyl polyethers, sorbitan esters, such as sorbitan fatty acid esters, or polyoxyethylene sorbitan esters, such as, for example, polyoxyethylene sorbitan fatty acid esters.

Dusting agents are obtained by grinding the active ingredient with finely divided solid substances, for example talc, natural clays, such as kaolin, bentonite or pyrophyllite, or diatomaceous earth.

Suspension concentrates may be water-based or oil-based. They can be produced, for example, by wet grinding by means of standard commercial bead mills and if appropriate addition of surfactants, as have for example already been listed above in connection with the other types of formulation.

Emulsions, e.g. oil-in-water emulsions (EW), can be prepared, for example, by means of stirrers, colloid mills and/or static mixers using aqueous organic solvents and if appropriate surfactants, as have for example already been listed above in connection with the other types of formulation.

Granules can be prepared either by atomizing the active ingredient onto granulated inert material that is capable of adsorption or by applying active ingredient concentrates by means of adhesives, e.g. polyvinyl alcohol, sodium polyacrylate or else mineral oils, onto the surface of carrier substances such as sand, kaolinites or of granulated inert material. Suitable active ingredients can also be granulated in the manner customary for producing fertilizer granules—if desired in a mixture with fertilizers.

Water-dispersible granules are usually prepared by customary methods such as spray-drying, fluidized-bed granulation, pan granulation, mixing with high-speed mixers and extrusion without solid inert material.

For the preparation of pan granules, fluidized-bed granules, extruder granules and spray granules, see, for example, methods in "Spray-Drying Handbook" 3rd ed. 1979, G. Goodwin Ltd., London; J. E. Browning, "Agglomeration", Chemical and Engineering 1967, pages 147 ff; "Perry's Chemical Engineer's Handbook", 5th Ed., McGraw-Hill, New York 1973, pp. 8-57.

For further details relating to the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical preparations comprise generally 0.1 to 99% by weight, in particular 0.1 to 95% by weight, of active ingredient of the formula (I).

In spray powders, the active ingredient concentration is, for example, about 10 to 90% by weight, the remainder to 100% by weight consists of customary formulation constituents. In the case of emulsifiable concentrates, the active ingredient concentration can be about 1 to 90, preferably 5 to 80% by weight. Dust-like formulations comprise 1 to 30% by weight of active ingredient, preferably in most cases 5 to 20% by weight of active ingredient, sprayable solutions comprise about 0.05 to 80, preferably 2 to 50% by weight of active ingredient. In the case of water-dispersible granules, the active ingredient content depends partly on whether the active compound is present in liquid or solid form and which granulation auxiliaries, fillers etc. are used. In the case of the water-dispersible granules, the content of active ingredient is, for example, between 1 and 95% by weight, preferably between 10 and 80% by weight.

In addition, the specified active ingredient formulations optionally comprise the adhesives, wetting agents, dispersants, emulsifiers, penetration agents, preservatives, antifreezes and solvents, fillers, carriers and colorants, antifoams, evaporation inhibitors and agents which influence the pH and the viscosity that are customary in each case.

The compounds of the formula (I) or their salts can be used as such or combined in the form of their preparations (formulations) with other pesticidally active substances, such as, for example, insecticides, acaricides, nematicides, herbicides, fungicides, safeners, fertilizers and/or growth regulators, e.g. as ready mix or as tank mixes.

Combination partners which can be used for the compounds according to the invention in mixture formulations or in the tank mix are, for example, known active ingredients which are based on an inhibition of, for example, acetolactate synthase, acetyl-coenzyme-A-carboxylase, cellulose synthase, enolpyruvylshikimate-3-phosphate synthase, glutamine synthetase, p-hydroxyphenylpyruvate dioxygenase, phytoene desaturase, photosystem I, photosystem II, protoporphyrinogen oxidase, as described, for example, in Weed Research 26 (1986) 441-445 or "The Pesticide Manual", 13th edition, The British Crop Protection Council and the Royal Soc. of Chemistry, 2003 and literature cited therein. Known herbicides or plant growth regulators which can be combined with the compounds according to the invention are, for example, the following active ingredients (the compounds are designated either with the "common name" in accordance with the International Organization for Standardization (ISO) or with the chemical name or with the code number) and always encompass all of the application forms such as acids, salts, esters and isomers such as stereoisomers and optical isomers. Here, by way of example, one and sometimes also more application forms are specified:

acetochlor, acibenzolar, acibenzolar-S-methyl, acifluorfen, acifluorfen-sodium, aclonifen, alachlor, allidochlor, alloxydim, alloxydim-sodium, ametryn, amicarbazone, amidochlor, amidosulfuron, aminopyralid, amitrole, ammonium sulfamate, ancymidol, anilofos, asulam, atrazine, azafenidin, azimsulfuron, aziprotryn, BAH-043, BAS-140H, BAS-693H, BAS-714H, BAS-762H, BAS-776H, BAS-800H, beflubutamid, benazolin, benazolin-ethyl, bencarbazone, benfluralin, benfuresate, bensulide, bensulfuron-methyl, bentazone, benzfendizone, benzobicyclon, benzofenap, benzofluor, benzoylprop, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat chloride, chlornitrofen, chlorophthalim, chlorthal-dimethyl, chlorotoluron, chlorsulfuron, cinidon, cinidon-ethyl, cinmethylin, cinosulfuron, clethodim, clodinafop, clodinafop-propargyl, clofencet, clomazone, clomeprop, cloprop, clopyralid, cloransulam, cloransulam-methyl, cumyluron, cyanamide, cyanazine, cyclanilide, cycloate, cyclosulfamuron, cycloxydim, cycluron, cyhalofop, cyhalofop-butyl, cyperquat, cyprazine, cyprazole, 2,4-D, 2,4-DB, daimuron/dymron, dalapon, daminozide, dazomet, n-decanol, desmedipham, desmetryn, detosyl-pyrazolate (DTP), diallate, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dimefuron, dikegulac-sodium, dimefuron, dimepiperate, dimethachlor, dimethametryn, dimethenamid, dimethenamid-P, dimethipin, dimetrasulfuron, dinitramine, dinoseb, dinoterb, diphenamid, dipropetryn, diquat, diquat-dibromide, dithiopyr, diuron, DNOC, eglinazine-ethyl, endothal, EPTC, esprocarb, ethalfluralin, ethametsulfuron-methyl, ethephon, ethidimuron, ethiozin, ethofumesate, ethoxyfen, ethoxyfen-ethyl, ethoxysulfuron, etobenzanid, F-5331, i.e. N-[2-chloro-4-fluoro-5-[4-(3-fluoropropyl)-4,5-dihydro-5-oxo-1H-tetrazol-1-yl]phenyl]-ethanesulfonamide, fenoprop, fenoxaprop, fenoxaprop-P, fenoxaprop-ethyl, fenoxaprop-P-ethyl, fentrazamide, fenuron, flamprop, flamprop-M-isopropyl, flamprop-M-methyl, flazasulfuron, florasulam, fluazifop, fluazifop-P, fluazifop-butyl, fluazifop-P-butyl, fluazolate, flucarbazone, flucarbazone-sodium, flucetosulfuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, fluorochloridone, fluoroxypyr, fluoroxypyr-meptyl, flurprimidol, flurtamone, fluthiacet, fluthiacet-methyl, fluthiamide, fomesafen, foramsulfuron, forchlorfenuron, fosamine, furyloxyfen, gibberellic acid, glufosinate, L-glufosinate, L-glufosinate-ammonium, glufosinate-ammonium, glyphosate, glyphosate-isopropylammonium, H-9201, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HNPC-9908, HOK-201, HW-02, imazamethabenz, imazamethabenz-methyl, imazamox, imazapic, imazapyr, imazaquin, imazethapyr, imazosulfuron, inabenfide, indanofan, indole acetic acid (IAA), 4-indol-3-ylbuttyric acid (IBA), iodosulfuron, iodosulfuron-methyl-sodium, ioxynil, isocarbamid, isopropalin, isoproturon, isouron, isoxaben, isoxachlortole, isoxaflutole, isoxapyrifop, IDH-100, KUH-043, KUH-071, karbutilate, ketospiradox, lactofen, lenacil, linuron, maleic hydrazide, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat chloride, mesosulfuron, mesosulfuron-methyl, mesotrione, methabenzthiazuron, metam, metamifop, metamitron, metazachlor, methazole, methoxyphenone, methyldymron, 1-methylcyclopropene, methyl isothiocyanate, metobenzuron, metobromuron, metolachlor, S-metolachlor, metosulam, metoxuron, metribuzin, metsulfuron, metsulfuron-methyl, molinate, monalide, monocarbamide, monocarbamide dihydrogensulfate, monolinuron, monosulfuron, monuron, MT 128, MT-5950, i.e. N-[3-chloro-4-(1-methylethyl)phenyl]-2-methylpentanamide, NGGC-011, naproanilide, napropamide, naptalam, NC-310, i.e. 4-(2,4-dichlorobenzoyl)-1-methyl-5-benzyloxypyrazole, neburon, nicosulfuron, nipyraclofen, nitralin, nitrofen, nitrophenolat-sodium (isomer mixture), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazol, paraquat, paraquat dichloride, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazol, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyzamide, prosulfalin, prosulfocarb, prosulfuron, prynachlor, pyraclonil, pyraflufen, pyraflufen-ethyl, pyrasulfotole, pyrazolynate (pyrazolate), pyrazosulfuron-ethyl, pyrazoxyfen, pyribambenz, pyribambenz-isopropyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, secbumeton, sethoxydim, siduron, simazine, simetryn, SN-106279, sulcotrione, sulfallate (CDEC), sulfentrazone, sulfometuron, sulfometuron-methyl, sulfosate (glyphosate-trimesium), sulfosulfuron, SYN-523, SYP-249, SYP-298, SYP-300, tebutam, tebuthiuron, tecnazene, tefuryltrione, tembotrione, tepraloxydim, terbacil, terbucarb, terbuchlor, terbumeton, terbuthylazine, terbutryn, TH-547, thenylchlor, thiafluamide, thiazafluoron, thiazopyr, thidiazimin, thidiazuron, thiencarbazone, thiencarbazone-methyl, thifensulfuron, thifensulfuron-methyl, thiobencarb, tiocarbazil, topramezone, tralkoxydim, triallate, triasulfuron, triaziflam, triazofenamide, tribenuron, tribenuron-methyl, trichloroacetic acid (TCA), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate, ZJ-0166, ZJ-0270, ZJ-0543, ZJ-0862 and the following compounds

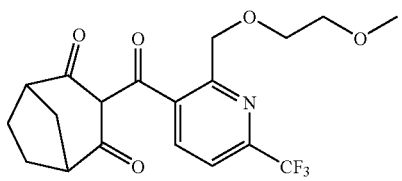

-continued

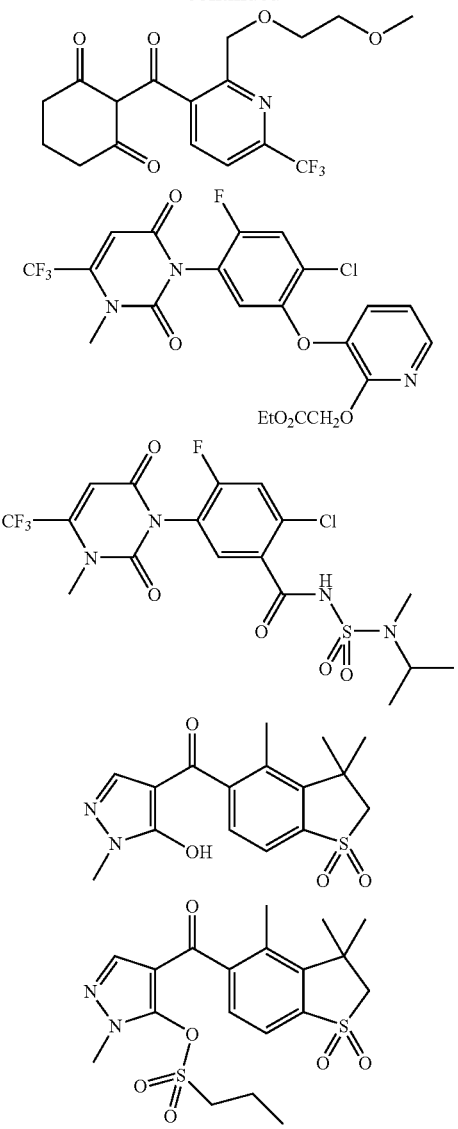

Of particular interest is the selective control of harmful plants in crops of useful plants and ornamental plants. Although the compounds of the formula (I) according to the invention already have very good to adequate selectivity in many crops, it is in principle possible, in some crops and primarily also in the case of mixtures with other herbicides which are less selective, for phytotoxicities on the crop plants to occur. In this connection, combinations of compounds of the formula (I) according to the invention are of particular interest which comprise the compounds of the formula (I) or their combinations with other herbicides or pesticides and safeners. The safeners which are used in an antidotically effective content reduce the phytotoxic side-effects of the herbicides/pesticides used, e.g. in economically important crops such as cereals (wheat, barley, rye, corn, rice, millet), sugarbeet, sugarcane, rapeseed, cotton and soybean, preferably cereals. The following groups of compounds are suitable, for example, as safeners for the compounds (I) alone or else in their combinations with further pesticides:

The safeners are preferably selected from the group consisting of:

S1) compounds of the formula (S1),

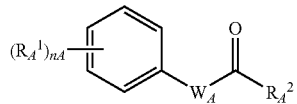

(S1)

where the symbols and indices have the following meanings:

$n_A$ is a natural number from 0 to 5, preferably 0 to 3;

$R_A{}^1$ is halogen, $(C_1-C_4)$-alkyl, $(C_1-C_4)$-alkoxy, nitro or $(C_1-C_4)$-haloalkyl;

$W_A$ is an unsubstituted or substituted divalent heterocyclic radical from the group of the partially unsaturated or aromatic five-ring heterocycles having 1 to 3 heteroring atoms from the group consisting of N and O, where at least one N atom and at most one O atom is present in the ring, preferably a radical from the group $(W_A{}^1)$ to $(W_A{}^4)$,

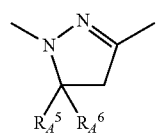

$(W_A{}^1)$

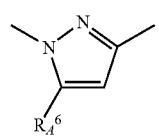

$(W_A{}^2)$

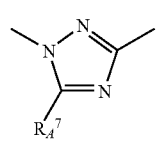

$(W_A{}^3)$

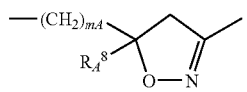

$(W_A{}^4)$ $m_A$ is 0 or 1;

$R_A{}^2$ is $OR_A{}^3$, $SR_A{}^3$ or $NR_A{}^3R_A{}^4$ or a saturated or unsaturated 3- to 7-membered heterocycle with at least one N atom and up to 3 heteroatoms, preferably from the group consisting of O and S, which is bonded to the carbonyl group in (S1) via the N atom and is unsubstituted or substituted by radicals from the group consisting of $(C_1-C_4)$-alkyl, $(C_1-C_4)$-alkoxy or optionally substituted phenyl, preferably a radical of the formula $OR_A{}^3$, $NHR_A{}^4$ or $N(CH_3)_2$, in particular of the formula $OR_A{}^3$;

$R_A{}^3$ is hydrogen or an unsubstituted or substituted aliphatic hydrocarbon radical, preferably having in total 1 to 18 carbon atoms;

$R_A{}^4$ is hydrogen, $(C_1-C_6)$-alkyl, $(C_1-C_6)$-alkoxy or substituted or unsubstituted phenyl;

$R_A{}^5$ is H, $(C_1-C_8)$-alkyl, $(C_1-C_8)$-haloalkyl, $(C_1-C_4)$-alkoxy-$(C_1-C_8)$-alkyl, cyano or $COOR_A{}^9$, in which $R_A{}^9$ is hydrogen, $(C_1-C_8)$-alkyl, $(C_1-C_8)$-haloalkyl, $(C_1-C_4)$-alkoxy-$(C_1-C_4)$-alkyl, $(C_1-C_6)$-hydroxyalkyl, $(C_3-C_{12})$-cycloalkyl or tri-$(C_1-C_4)$-alkylsilyl;

$R_A{}^6$, $R_A{}^7$, $R_A{}^8$ are identical or different, hydrogen, $(C_1-C_8)$-alkyl, $(C_1-C_8)$-haloalkyl, $(C_3-C_{12})$-cycloalkyl or substituted or unsubstituted phenyl;

preferably:

a) compounds of the dichlorophenylpyrazoline-3-carboxylic acid type ($S1^a$), preferably compounds such as 1-(2,4-dichlorophenyl)-5-(ethoxycarbonyl)-5-methyl-2-pyrazoline-3-carboxylic acid, ethyl 1-(2,4-dichlorophenyl)-5-(ethoxycarbonyl)-5-methyl-2-pyrazoline-3-carboxylate (S1-1) ("mefenpyr-diethyl"), and related compounds, as described in WO-A-91/07874;

b) derivatives of dichlorophenylpyrazolecarboxylic acid ($S1^b$), preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl)pyrazole-3-carboxylate (S1-4) and related compounds, as described in EP-A-333 131 and EP-A-269 806;

c) derivatives of 1,5-diphenylpyrazole-3-carboxylic acid ($S1^c$), preferably compounds such as ethyl 1-(2,4-dichlorophenyl)-5-phenylpyrazole-3-carboxylate (S1-5), methyl 1-(2-chlorophenyl)-5-phenylpyrazole-3-carboxylate (S1-6) and related compounds, as described, for example, in EP-A-268554;

d) compounds of the triazolecarboxylic acid type ($S1^d$), preferably compounds such as fenchlorazole(-ethyl), i.e. ethyl 1-(2,4-dichlorophenyl)-5-trichloromethyl-(1H)-1,2,4-triazole-3-carboxylate (S1-7), and related compounds, as described in EP-A-174 562 and EP-A-346 620;

e) compounds of the 5-benzyl- or 5-phenyl-2-isoxazoline-3-carboxylic acid type or of the 5,5-diphenyl-2-isoxazoline-3-carboxylic acid type ($S1^e$), preferably compounds such as ethyl 5-(2,4-dichlorobenzyl)-2-isoxazoline-3-carboxylate (S1-8) or ethyl 5-phenyl-2-isoxazoline-3-carboxylate (S1-9) and related compounds, as described in WO-A-91/08202, or 5,5-diphenyl-2-isoxazoline-carboxylic acid (S1-10) or ethyl 5,5-diphenyl-2-isoxazoline-carboxylate (S1-11) ("isoxadifen-ethyl") or n-propyl 5,5-diphenyl-2-isoxazoline-carboxylate (S1-12) or of the ethyl 5-(4-fluorophenyl)-5-phenyl-2-isoxazoline-3-carboxylate type (S1-13), as described in the patent application WO-A-95/07897.

S2) Quinoline derivatives of the formula (S2),

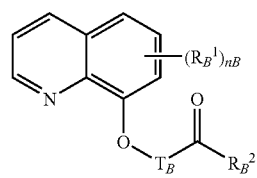

(S2)

where the symbols and indices have the following meanings:

$R_B{}^1$ is halogen, $(C_1-C_4)$-alkyl, $(C_1-C_4)$-alkoxy, nitro or $(C_1-C_4)$-haloalkyl;

$n_B$ is a natural number from 0 to 5, preferably 0 to 3;

$R_B{}^2$ is $OR_B{}^3$, $SR_B{}^3$ or $NR_B{}^3R_B{}^4$ or a saturated or unsaturated 3- to 7-membered heterocycle having at least one N atom and up to 3 heteroatoms, preferably from the group consisting of O and S, which is joined to the carbonyl group in (S2) via the N atom and is unsubstituted or substituted by radicals from the group consisting of $(C_1-C_4)$-alkyl, $(C_1-C_4)$-alkoxy or optionally substituted phenyl, preferably a radical of the formula $OR_B{}^3$, $NHR_B{}^4$ or $N(CH_3)_2$, in particular of the formula $OR_B{}^3$;

$R_B^3$ is hydrogen or an unsubstituted or substituted aliphatic hydrocarbon radical, preferably having in total 1 to 18 carbon atoms;

$R_B^4$ is hydrogen, $(C_1-C_6)$-alkyl, $(C_1-C_6)$-alkoxy or substituted or unsubstituted phenyl;

$T_B$ is a $(C_1$ or $C_2)$-alkanediyl chain which is unsubstituted or substituted by one or two $(C_1-C_4)$-alkyl radicals or by $[(C_1-C_3)$-alkoxy]carbonyl;

preferably:

a) compounds of the 8-quinolinoxy acetic acid type ($S2^a$), preferably
  1-methylhexyl (5-chloro-8-quinolinoxy)acetate ("cloquintocet-mexyl") (S2-1),
  1,3-dimethylbut-1-yl (5-chloro-8-quinolinoxy)acetate (S2-2),
  4-allyloxybutyl (5-chloro-8-quinolinoxy)acetate (S2-3),
  1-allyloxyprop-2-yl (5-chloro-8-quinolinoxy)acetate (S2-4),
  ethyl (5-chloro-8-quinolinoxy)acetate (S2-5),
  methyl (5-chloro-8-quinolinoxy)acetate (S2-6),
  allyl (5-chloro-8-quinolinoxy)acetate (S2-7),
  2-(2-propylideneiminoxy)-1-ethyl (5-chloro-8-quinolinoxy)acetate (S2-8),
  2-oxoprop-1-yl (5-chloro-8-quinolinoxy)acetate (S2-9) and related compounds, as described in EP-A-86 750, EP-A-94 349 and EP-A-191 736 or EP-A-0 492 366, and also (5-chloro-8-quinolinoxy)acetic acid (S2-10), its hydrates and salts, for example its lithium, sodium, potassium, calcium, magnesium, aluminum, iron, ammonium, quaternary ammonium, sulfonium or phosphonium salts, as described in WO-A-2002/34048;

b) compounds of the (5-chloro-8-quinolinoxy)malonic acid type ($S2^b$), preferably compounds such as diethyl (5-chloro-8-quinolinoxy)malonate, diallyl (5-chloro-8-quinolinoxy)malonate, methyl ethyl (5-chloro-8-quinolinoxy)-malonate and related compounds, as described in EP-A-0 582 198.

S3) Compounds of the formula (S3)

$$R_C^1 \underset{\underset{R_C^3}{|}}{\overset{\overset{O}{\|}}{C}} N R_C^2 \quad (S3)$$

where the symbols and indices have the following meanings:

$R_C^1$ is $(C_1-C_4)$-alkyl, $(C_1-C_4)$-haloalkyl, $(C_2-C_4)$-alkenyl, $(C_2-C_4)$-haloalkenyl, $(C_3-C_7)$-cycloalkyl, preferably dichloromethyl;

$R_C^2$, $R_C^3$ are identical or different, hydrogen, $(C_1-C_4)$-alkyl, $(C_2-C_4)$-alkenyl, $(C_2-C_4)$-alkynyl, $(C_1-C_4)$-haloalkyl, $(C_2-C_4)$-haloalkenyl, $(C_1-C_4)$-alkylcarbamoyl-$(C_1-C_4)$-alkyl, $(C_2-C_4)$-alkenylcarbamoyl-$(C_1-C_4)$-alkyl, $(C_1-C_4)$-alkoxy-$(C_1-C_4)$-alkyl, dioxolanyl-$(C_1-C_4)$-alkyl, thiazolyl, furyl, furylalkyl, thienyl, piperidyl, substituted or unsubstituted phenyl, or $R_C^2$ and $R_C^3$ form together a substituted or unsubstituted heterocyclic ring, preferably an oxazolidine, thiazolidine, piperidine, morpholine, hexahydropyrimidine or benzoxazine ring;

preferably:

active ingredients of the dichloroacetamide type, which are often used as pre-emergence safeners (soil-acting safeners), such as, for example, "dichlormid" (N,N-diallyl-2,2-dichloroacetamide) (S3-1), "R-29148" (3-dichloroacetyl-2,2,5-trimethyl-1,3-oxazolidine) from Stauffer (S3-2), "R-28725" (3-dichloroacetyl-2,2-dimethyl-1,3-oxazolidine) from Stauffer (S3-3), "benoxacor" (4-dichloroacetyl-3,4-dihydro-3-methyl-2H-1,4-benzoxazine) (S3-4), "PPG-1292" (N-allyl-N-[(1,3-dioxolan-2-yl)methyl] dichloroacetamide) from PPG Industries (S3-5), "DKA-24" (N-allyl-N-[(allylaminocarbonyl)methyl] dichloroacetamide) from Sagro-Chem (S3-6), "AD-67" or "MON 4660" (3-dichloroacetyl-1-oxa-3-azaspiro[4,5]decane) from Nitrokemia or Monsanto (S3-7), "TI-35" (1-dichloroacetylazepane) from TR1-Chemical RT (S3-8), "diclonon" (dicyclonone) or "BAS145138" or "LAB145138" (S3-9) ((RS)-1-dichloroacetyl-3,3,8a-trimethylperhydropyrrolo[1,2-a]pyrimidin-6-one) from BASF, "furilazole" or "MON 13900" ((RS)-3-dichloroacetyl-5-(2-furyl)-2,2-dimethyl-oxazolidine) (S3-10); and also its (R)-isomer (S3-11).

S4) N-Acylsulfonamides of the formula (S4) and their salts, in which the symbols and indices have the following meanings:

$X_D$ is CH or N;

$R_D^1$ is CO—$NR_D^5R_D^6$ or NHCO—$R_D^7$;

$R_D^2$ is halogen, $(C_1-C_4)$-haloalkyl, $(C_1-C_4)$-haloalkoxy, nitro, $(C_1-C_4)$-alkyl, $(C_1-C_4)$-alkoxy, $(C_1-C_4)$-alkylsulfonyl, $(C_1-C_4)$-alkoxycarbonyl or $(C_1-C_4)$-alkylcarbonyl;

$R_D^3$ is hydrogen, $(C_1-C_4)$-alkyl, $(C_2-C_4)$-alkenyl or $(C_2-C_4)$-alkynyl;

$R_D^4$ is halogen, nitro, $(C_1-C_4)$-alkyl, $(C_1-C_4)$-haloalkyl, $(C_1-C_4)$-haloalkoxy, $(C_3-C_6)$-cycloalkyl, phenyl, $(C_1-C_4)$-alkoxy, cyano, $(C_1-C_4)$-alkylthio, $(C_1-C_4)$-alkyl-sulfinyl, $(C_1-C_4)$-alkylsulfonyl, $(C_1-C_4)$-alkoxycarbonyl or $(C_1-C_4)$-alkylcarbonyl;

$R_D^5$ is hydrogen, $(C_1-C_6)$-alkyl, $(C_3-C_6)$-cycloalkyl, $(C_2-C_6)$-alkenyl, $(C_2-C_6)$-alkynyl, $(C_5-C_6)$-cycloalkenyl, phenyl or 3- to 6-membered heterocyclyl comprising $v_D$ heteroatoms from the group consisting of nitrogen, oxygen and sulfur, where the seven last-mentioned radicals are substituted by $v_D$ substituents from the group consisting of halogen, $(C_1-C_6)$-alkoxy, $(C_1-C_6)$-haloalkoxy, $(C_1-C_2)$-alkylsulfinyl, $(C_1-C_2)$-alkylsulfonyl, $(C_3-C_6)$-cycloalkyl, $(C_1-C_4)$-alkoxycarbonyl, $(C_1-C_4)$-alkylcarbonyl and phenyl and, in the case of cyclic radicals, also $(C_1-C_4)$-alkyl and $(C_1-C_4)$-haloalkyl;

$R_D^6$ is hydrogen, $(C_1-C_6)$-alkyl, $(C_2-C_6)$-alkenyl or $(C_2-C_6)$-alkynyl, where the three last-mentioned radicals are substituted by $v_D$ radicals from the group consisting of halogen, hydroxy, $(C_1-C_4)$-alkyl, $(C_1-C_4)$-alkoxy and $(C_1-C_4)$-alkylthio, or $R_D^5$ and $R_D^6$ together with the nitrogen atom carrying them form a pyrrolidinyl or piperidinyl radical;

$R_D^7$ is hydrogen, $(C_1-C_4)$-alkylamino, di$(C_1-C_4)$-alkylamino, $(C_1-C_6)$-alkyl, $(C_3-C_6)$-cycloalkyl, where the 2 last-mentioned radicals are substituted by $v_D$ substituents from the group consisting of halogen, $(C_1-C_4)$-alkoxy, $(C_1-C_6)$-haloalkoxy and $(C_1-C_4)$-alkylthio and, in the case of cyclic radicals, also $(C_1-C_4)$-alkyl and $(C_1-C_4)$-haloalkyl;

$n_D$ is 0, 1 or 2;

$m_D$ is 1 or 2;

$v_D$ is 0, 1, 2 or 3;

of which preference is given to compounds of the N-acylsulfonamide type, for example of the following formula (S4$^a$), which are known, for example, from WO-A-97/45016

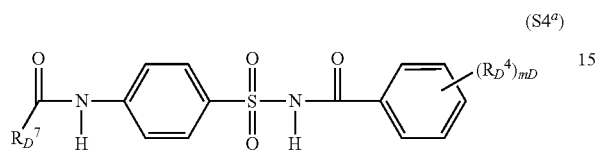

(S4$^a$)

in which $R_D^7$ is $(C_1-C_6)$-alkyl, $(C_3-C_6)$-cycloalkyl, where the 2 last-mentioned radicals are substituted by $v_D$ substituents from the group consisting of halogen, $(C_1-C_4)$-alkoxy, $(C_1-C_6)$-haloalkoxy and $(C_1-C_4)$-alkylthio and, in the case of cyclic radicals, also $(C_1-C_4)$-alkyl and $(C_1-C_4)$-haloalkyl;

$R_D^4$ is halogen, $(C_1-C_4)$-alkyl, $(C_1-C_4)$-alkoxy, $CF_3$, $m_D$ is 1 or 2;

$v_D$ is 0, 1, 2 or 3;

and acylsulfamoylbenzamides, e.g. of the following formula (S4$^b$), which are known, for example, from WO-A-99/16744,

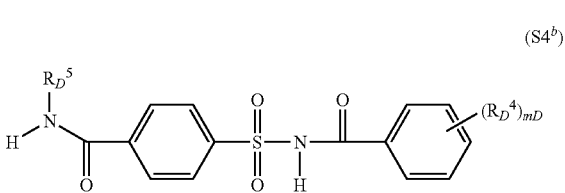

(S4$^b$)

e.g. those in which $R_D^5$=cyclopropyl and $(R_D^4)$=2-OMe ("cyprosulfamide", S4-1), $R_D^5$=cyclopropyl and $(R_D^4)$=5-Cl-2-OMe (S4-2), $R_D^5$=ethyl and $(R_D^4)$=2-OMe (S4-3), $R_D^5$=isopropyl and $(R_D^4)$=5-Cl-2-OMe (S4-4) and $R_D^5$=isopropyl and $(R_D^4)$=2-OMe (S4-5), and compounds of the N-acylsulfamoylphenylurea type of the formula (S4$^c$), which are known, for example, from EP-A-365484,

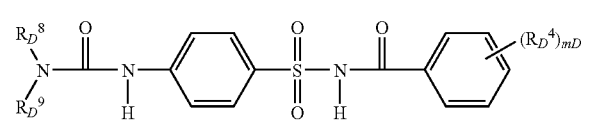

(S4$^c$)

in which $R_D^8$ and $R_D^9$, independently of one another, are hydrogen, $(C_1-C_8)$-alkyl, $(C_3-C_8)$-cycloalkyl, $(C_3-C_6)$-alkenyl, $(C_3-C_6)$-alkynyl, $R_D^4$ is halogen, $(C_1-C_4)$-alkyl, $(C_1-C_4)$-alkoxy, $CF_3$ $m_D$ is 1 or 2;

for example

1-[4-(N-2-methoxybenzoylsulfamoyl)phenyl]-3-methylurea,

1-[4-(N-2-methoxybenzoylsulfamoyl)phenyl]-3,3-dimethylurea,

1-[4-(N-4,5-dimethylbenzoylsulfamoyl)phenyl]-3-methylurea.

S5) Active ingredients from the class of hydroxyaromatics and aromatic-aliphatic carboxylic acid derivatives (S5), e.g. ethyl 3,4,5-triacetoxybenzoate, 3,5-dimethoxy-4-hydroxybenzoic acid, 3,5-dihydroxybenzoic acid, 4-hydroxysalicylic acid, 4-fluorosalicyclic acid, 2-hydroxycinnamic acid, 2,4-dichlorocinnamic acid, as described in WO-A-2004/084631, WO-A-2005/015994, WO-A-2005/016001.

S6) Active ingredients from the class of the 1,2-dihydroquinoxalin-2-ones (S6), e.g. 1-methyl-3-(2-thienyl)-1,2-dihydroquinoxaline-2-one, 1-methyl-3-(2-thienyl)-1,2-dihydroquinoxaline-2-thione, 1-(2-aminoethyl)-3-(2-thienyl)-1,2-dihydro-quinoxalin-2-one hydrochloride, 1-(2-methylsulfonylaminoethyl)-3-(2-thienyl)-1,2-dihydroquinoxalin-2-one, as described in WO-A-2005/112630.

S7) Compounds of the formula (S7), as described in WO-A-1998/38856

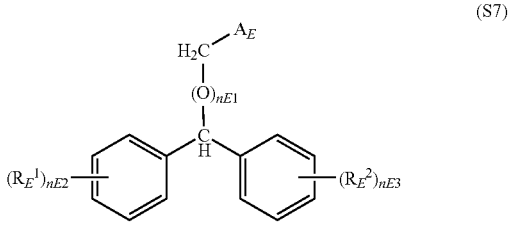

(S7)

in which the symbols and the indices have the following meanings:

$R_E^1$, $R_E^2$ independently of one another are halogen, $(C_1-C_4)$-alkyl, $(C_1-C_4)$-alkoxy, $(C_1-C_4)$-haloalkyl, $(C_1-C_4)$-alkylamino, di$(C_1-C_4)$-alkylamino, nitro;

$A_E$ is $COOR_E^3$ or $COSR_E^4$ $R_E^3$, $R_E^4$ independently of one another are hydrogen, $(C_1-C_4)$-alkyl, $(C_2-C_6)$-alkenyl, $(C_2-C_4)$-alkynyl, cyanoalkyl, $(C_1-C_4)$-haloalkyl, phenyl, nitrophenyl, benzyl, halobenzyl, pyridinylalkyl and alkylammonium, $n_E^1$ is 0 or 1

$n_E^2$, $n_E^3$ independently of one another are 0, 1 or 2, preferably:

diphenylmethoxyacetic acid, ethyl diphenylmethoxyacetate, methyl diphenylmethoxyacetate (CAS Reg. No. 41858-19-9) (S7-1).

S8) Compounds of the formula (S8), as described in WO-A-98/27049

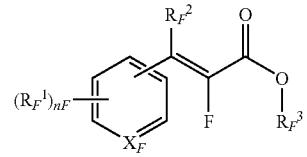

in which
X$_F$ is CH or N,
n$_F$ if X$_F$=N, is an integer from 0 to 4 and
if X$_F$=CH, is an integer from 0 to 5,
R$_F^1$ is halogen, (C$_1$-C$_4$)-alkyl, (C$_1$-C$_4$)-haloalkyl, (C$_1$-C$_4$)-alkoxy, (C$_1$-C$_4$)-haloalkoxy, nitro, (C$_1$-C$_4$)-alkylthio, (C$_1$-C$_4$)-alkylsulfonyl, (C$_1$-C$_4$)-alkoxycarbonyl, optionally substituted phenyl, optionally substituted phenoxy,
R$_F^2$ is hydrogen or (C$_1$-C$_4$)-alkyl,
R$_F^3$ is hydrogen, (C$_1$-C$_8$)-alkyl, (C$_2$-C$_4$)-alkenyl, (C$_2$-C$_4$)-alkynyl, or aryl, where each of the aforementioned C-containing radicals is unsubstituted or substituted by one or more, preferably up to three, identical or different radicals from the group consisting of halogen and alkoxy; or salts thereof, preferably compounds in which
X$_F$ is CH,
n$_F$ is an integer from 0 to 2,
R$_F^1$ is halogen, (C$_1$-C$_4$)-alkyl, (C$_1$-C$_4$)-haloalkyl, (C$_1$-C$_4$)-alkoxy, (C$_1$-C$_4$)-haloalkoxy,
R$_F^2$ is hydrogen or (C$_1$-C$_4$)-alkyl,
R$_F^3$ is hydrogen, (C$_1$-C$_8$)-alkyl, (C$_2$-C$_4$)-alkenyl, (C$_2$-C$_4$)-alkynyl, or aryl, where each of the aforementioned C-containing radicals is unsubstituted or substituted by one or more, preferably up to three, identical or different radicals from the group consisting of halogen and alkoxy, or salts thereof.

S9) Active ingredients from the class of the 3-(5-tetrazolylcarbonyl)-2-quinolones (S9), e.g.
1,2-dihydro-4-hydroxy-1-ethyl-3-(5-tetrazolylcarbonyl)-2-quinolone (CAS Reg. No. 219479-18-2), 1,2-dihydro-4-hydroxy-1-methyl-3-(5-tetrazolylcarbonyl)-2-quinolone (CAS Reg. No. 95855-00-8), as described in WO-A-1999/000020.

S10) Compounds of the formulae (S10$^a$) or (S10$^b$)
as described in WO-A-2007/023719 and WO-A-2007/023764

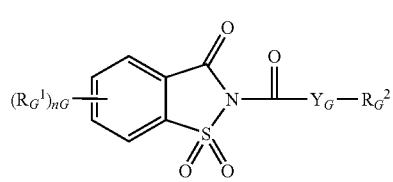

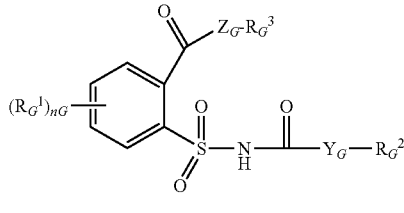

in which
R$_G^1$ is halogen, (C$_1$-C$_4$)-alkyl, methoxy, nitro, cyano, CF$_3$, OCF$_3$
Y$_G$, Z$_G$ independently of one another are O or S,
n$_G$ is an integer from 0 to 4,
R$_G^2$ is (C$_1$-C$_{16}$)-alkyl, (C$_2$-C$_6$)-alkenyl, (C$_3$-C$_6$)-cycloalkyl, aryl; benzyl, halobenzyl,
R$_G^3$ is hydrogen or (C$_1$-C$_6$)-alkyl.

S11) Active ingredients of the oxyimino compound type (S11), which are known as seed dressings, such as, for example,
"oxabetrinil" ((Z)-1,3-dioxolan-2-ylmethoxyimino(phenyl)acetonitrile) (S11-1), which is known as seed dressing safener for millet against metolachlor damage,
"fluxofenim" (1-(4-chlorophenyl)-2,2,2-trifluoro-1-ethanone O-(1,3-dioxolan-2-ylmethyl)oxime) (S11-2), which is known as seed dressing safener for millet against metolachlor damage, and
"cyometrinil" or "CGA-43089" ((Z)-cyanomethoxyimino(phenyl)acetonitrile) (S11-3), which is known as seed dressing safener for millet against metolachlor damage.

S12) Active ingredients from the class of the isothiochromanones (S12), such as, for example, methyl [(3-oxo-1H-2-benzothiopyran-4(3H)-ylidene)methoxy]acetate (CAS Reg. No. 205121-04-6) (S12-1) and related compounds from WO-A-1998/13361.

S13) One or more compounds from group (S13):
"naphthalic anhydride" (1,8-naphthalenedicarboxylic anhydride) (S13-1), which is known as seed dressing safener for corn against thiocarbamate herbicide damage,
"fenclorim" (4,6-dichloro-2-phenylpyrimidine) (S13-2), which is known as safener for pretilachlor in sown rice,
"flurazole" (benzyl 2-chloro-4-trifluoromethyl-1,3-thiazole-5-carboxylate) (S13-3), which is known as seed dressing safener for millet against alachlor and metolachlor damage,
"CL 304415" (CAS Reg. No. 31541-57-8) (4-carboxy-3,4-dihydro-2H-1-benzopyran-4-acetic acid) (S13-4) from American Cyanamid, which is known as safener for corn against imidazolinone damage,
"MG 191" (CAS Reg. No. 96420-72-3) (2-dichloromethyl-2-methyl-1,3-dioxolane) (S13-5) from Nitrokemia, which is known as safener for corn,
"MG-838" (CAS Reg. No. 133993-74-5) (2-propenyl 1-oxa-4-azaspiro[4.5]decane-4-carbodithioate) (S13-6) from Nitrokemia,
"disulfoton" (O,O-diethyl S-2-ethylthioethyl phosphorodithioate) (S13-7),
"dietholate" (O,O-diethylO-phenylphosphorothioate) (S13-8),
"mephenate" (4-chlorophenyl methylcarbamate) (S13-9).

S14) Active ingredients which, besides a herbicidal effect against harmful plants, also have a safener effect on crop plants such as rice, such as, for example, "dimepiperate" or "MY-93" (S-1-methyl-1-phenylethyl piperidine-1-carbothioate), which is known as safener for rice against molinate herbicide damage, "daimuron" or "SK 23" (1-(1-methyl-1-phenylethyl)-3-p-tolylurea), which is known as safener for rice against imazosulfuron herbicide damage, "cumyluron"="JC-940" (3-(2-chlorophenylmethyl)-1-(1-methyl-1-phenyl-ethyl)urea, see JP-A-60087254), which is known as safener for rice against some herbicide damage, "methoxyphenone" or "NK 049" (3,3'-dimethyl-4-methoxybenzophenone), which is known as safener for rice against some herbicide damage, "CSB" (1-bromo-4-(chloromethylsulfonyl)benzene) from Kumiai, (CAS Reg. No. 54091-06-4), which is known as safener against some herbicide damage in rice.

S15) Active ingredients which are primarily used as herbicides, but also have safener effect on crop plants, for example (2,4-dichlorophenoxy)acetic acid (2,4-D),
(4-chlorophenoxy)acetic acid,
(R,S)-2-(4-chloro-o-tolyloxy)propionic acid (mecoprop),
4-(2,4-dichlorophenoxy)butyric acid (2,4-DB),
(4-chloro-o-tolyloxy)acetic acid (MCPA),
4-(4-chloro-o-tolyloxy)butyric acid,
4-(4-chlorophenoxy)butyric acid,
3,6-dichloro-2-methoxybenzoic acid (dicamba),
1-(ethoxycarbonyl)ethyl 3,6-dichloro-2-methoxybenzoate (lactidichlor-ethyl).

Some of the safeners are already known as herbicides and thus, besides the herbicidal effect in respect of harmful plants, at the same time also develop a protective effect in respect of the crop plants.

The weight ratios of herbicide (mixture) to safener generally depend on the application rate of herbicide and the effectiveness of the particular safener and can vary within wide limits, for example in the range from 200:1 to 1:200, preferably 100:1 to 1:100, in particular 20:1 to 1:20. The safeners can be formulated analogously to the compounds of the formula (I) or mixtures thereof with further herbicides/pesticides and can be provided and applied as ready mix or tank mix with the herbicides.

For use, the formulations present in standard commercial form are, if appropriate, diluted in the usual manner, e.g. in the case of spray powders, emulsifiable concentrates, dispersions and water-dispersible granules by means of water. Dust-like preparations, soil and scatter granules, and also sprayable solutions are usually no longer diluted with further inert substances prior to use.

The required application rate of the compounds of the formula (I) varies inter alia with the external conditions such as temperature, humidity, the type of herbicide used. It can fluctuate within wide limits, e.g. between 0.001 and 10.0 kg/ha or more of active substance, but is preferably between 0.005 and 5 kg/ha.

The present invention is illustrated in more detail by reference to the examples below, although these do not limit the invention in any way.

A. Synthesis Examples

4-Amino-2-[(1R)-1,2,3,4-tetrahydronaphthalen-1-ylamino]pyrimidine-5-carbonitrile (Ex.: 1.30)

0.25 g (1.61 mmol) of 4-amino-2-chloropyrimidine-5-carbonitrile, 0.31 g (2.10 mmol) of (1R)-1,2,3,4-tetrahydronaphthalen-1-amine and 0.67 g (4.85 mmol) of potassium carbonate in 3 ml of N,N-dimethylformamide are heated at 120° C. for 4 hours, the crude mixture is concentrated by evaporation under a high vacuum, the remaining crude mixture is absorbed on silica gel and purified by means of column chromatography using heptane/ethyl acetate as eluent. Following concentration by evaporation, 0.22 g of 4-amino-2-[(1R)-1,2,3,4-tetrahydronaphthalen-1-ylamino]pyrimidine-5-carbonitrile (m.p. 167.6° C.) is obtained (yield 48% at 95% purity).

4-Amino-2-[(1R)-2,3-dihydro-1H-inden-1-ylamino]-6-ethylpyrimidine-5-carbonitrile (Ex.: 1.62)

0.25 g (1.09 mmol) of 4-amino-2-chloro-6-ethylpyrimidine-5-carbonitrile, 0.19 g (1.31 mmol) of (1R)-1,2,3,4-tetrahydronaphthalen-1-amine and 0.45 g (3.28 mmol) of potassium carbonate in 2 ml of N,N-dimethylacetamide are heated at 140° C. in a closed cell in a microwave for 30 minutes. The crude mixture obtained in this way is absorbed on silica gel and purified by means of column chromatography using heptane/ethyl acetate as eluent. Following concentration by evaporation, 0.28 g of 4-amino-2-[(1R)-2,3-dihydro-1H-inden-1-ylamino]-6-ethylpyrimidine-5-carbonitrile is obtained (yield 82% at 95% purity).

4-Amino-2-chloro-6-ethylpyrimidine-5-carbonitrile

With stirring, 200 ml of conc. hydrochloric acid are slowly added dropwise to 37.57 g of ca. 80% strength (178.76 mmol) of sodium cyano[1-(dicyanomethylidene)propyl]-azanide such that the reaction temperature does not exceed 30° C. The reaction mixture is then added to ca. 600 ml of ice water and the solid that is formed is isolated by filtering off with suction. After drying, 33.89 g of 4-amino-2-chloro-6-ethylpyrimidine-5-carbonitrile with the melting point 226.5° C. are obtained.

Sodium cyano[1-(dicyanomethylidene)propyl]azanide

In portions, 7.56 g of cyanamide are added to a solution of 32.38 g (33.4 ml, density=0.97 g/l) of 30% sodium methanolate solution and 100 ml of ethanol and the mixture is stirred at 25° C. for ca. 5 minutes; then, over the course of ca. 25 minutes, 30 g (ca. 90% strength, 180 mmol) of (1-ethoxypropylidene)malononitrile are added dropwise. The mixture is stirred for two hours, then the volatile constituents are largely removed by distillation, and the remaining residue is taken up in methylene chloride. The methylene chloride phase is separated off and the remaining 37.57 g of sodium cyano[1-(dicyanomethylidene)propyl]azanide with ca. 80% purity are used in the following stage.

(1-Ethoxypropylidene)malononitrile 33.03 g (0.5 mol) of malonodinitrile and 88.13 g (99.02 ml, 0.5 mol) of triethyl orthopropionate are heated at 100° C. for two hours, and the ethanol which is formed during this is distilled off overhead. The reaction mixture is left to cool and added to ca. 500 ml of water. The aqueous phase is extracted with ethyl acetate, then the organic phase is dried with sodium sulfate and, after filtering off the drying agent, is concentrated by evaporation. The resulting 72 g (purity ca. 90%) of (1-ethoxy-propylidene)malononitrile are used in the subsequent step without further purification.

5-Bromo-N2-[(1R,2S)-2,6-dimethyl-2,3-dihydro-1H-inden-1-yl]pyrimidine-2,4-diamine (Ex.: 1.67)

0.2 g (0.96 mmol) of 4-amino-5-bromo-2-chloropyrimidine, 0.196 g (1.15 mmol) of (1R,2S)-2,6-dimethyl-2,3-dihydro-1H-inden-1-amine and 0.399 g of potassium carbonate are heated in 1.5 ml of N,N-dimethylacetamide at 170° C. in a closed cell in a microwave for 60 minutes (Biotage initiator, http://www.biotage.com/DynPage.aspx?id=22001). The resulting crude mixture is absorbed on silica gel and purified by means of column chromatography using heptane/ethyl acetate as eluent. Following concentration by evaporation, 0.13 g of 5-bromo-N2-[(1R,2S)-2,6-dimethyl-2,3-dihydro-1H-inden-1-yl]pyrimidine-2,4-diamine is obtained (yield 37% at 95% purity).

N2-[(1R,2S)-2,6-Dimethyl-2,3-dihydro-1H-inden-1-yl]-5-[(trimethylsilyl)ethynyl]-pyrimidine-2,4-diamine (Ex.: 1.98)

A mixture of 0.310 g (0.93 mmol) of 5-bromo-N2-[(1R,2S)-2,6-dimethyl-2,3-dihydro-1H-inden-1-yl]pyrimidine-2,4-diamine, 0.183 g (0.26 ml, 1.86 mmol) of (trimethylsilyl)-acetylene, 0.050 g (0.05 mmol) of bis(triphenylphosphine) palladium(II) chloride and 0.01 g (0.05 mmol) of copper(I) iodide in 2 ml of triethylamine is stirred at 70° C. for 8 hours. After cooling, the resulting crude mixture is absorbed on silica gel and purified by means of column chromatography using heptane/ethyl acetate as eluent. Following concentration by evaporation, 0.04 g of 5-bromo-N2-N2-[(1R,2S)-2,6-dimethyl-2,3-dihydro-1H-inden-1-yl]-5-[(trimethylsilyl)ethynyl]pyrimidine-2,4-diamine was obtained (yield 10% at 85% purity).

N2-[(1R,2S)-2,6-Dimethyl-2,3-dihydro-1H-inden-1-yl]-5-ethynylpyrimidine-2,4-diamine (Ex.: 1.119)

0.427 g of potassium hydroxide is added to a mixture of 0.47 g (1.34 mmol) of N2-[(1R,2S)-2,6-dimethyl-2,3-dihydro-1H-inden-1-yl]-5-[(trimethylsilyl)ethynyl]pyrimidine-2,4-diamine (Ex.: 1.98) in 3 ml of methanol and 1 ml of water, the mixture is stirred for one hour at 25° C., concentrated by evaporation and taken up in water. Then, extraction is carried out with ethyl acetate, and the organic phase is dried and concentrated by evaporation. Following purification of the crude mixture by column-chromatographic separation, 0.139 g of N2-[(1R,2S)-2,6-dimethyl-2,3-dihydro-1H-inden-1-yl]-5-ethynylpyrimidine-2,4-diamine is obtained (yield 33% at 90% purity).

N2-[(1R)-1,2,3,4-Tetrahydronaphthalen-1-yl]-5-(trifluoromethyl)pyrimidine-2,4-diamine (Ex.: 1.108)

With stirring, 1.0 g of 2,4-dichloro-5-(trifluoromethyl)pyrimidine (Aldrich; order No. 684864) is added to a methanol ammonia solution (ca. 8 mol of ammonia in methanol), cooled to ca. 5° C., and the mixture is heated to 25° C. and stirred for two hours at the temperature. The mixture is concentrated by evaporation and added to water. Filtering with suction gives 0.56 g of a mixture of 4-amino-2-chloro-5-trifluoromethylpyrimidine (ca. 45%) and 2-amino-4-chloro-5-trifluoromethylpyrimidine (ca. 45%).

Then, a mixture of 0.25 g of the solid obtained above and 0.224 g (1.47 mmol) of (R)-1,2,3,4-tetrahydro-1-naphthylamine and 0.35 g (2.53 mmol) of potassium carbonate in 1 ml of N-methylpyrrolidone as solvent is heated in a closed cell in a microwave appliance (Biotage initiator, http://www.biotage.com/DynPage.aspx?id=22001) at 160° C. for 60 min. The crude mixture is absorbed on silica gel and, following separation by means of column chromatography, 0.167 g of N2-[(1R)-1,2,3,4-tetrahydronaphthalen-1-yl]-5-(trifluoromethyl)pyrimidine-2,4-diamine with a melting point of 130-131° C., (95% purity) is obtained.

4-Amino-2-{[(1R,2S)-2,6-dimethyl-2,3-dihydro-1H-inden-1-yl]amino}-6-(2-fluorophenyl)pyrimidine-5-carbonitrile (Ex.: 104)

A mixture of 0.20 g (0.76 mmol) of 4-amino-6-(2-fluorophenyl)-2-(methylsulfanyl)pyrimidine-5-carbonitrile and 0.5 g of (1R,2S)-2,6-dimethyl-2,3-dihydro-1H-inden-1-amine in 1 ml of N-methylpyrrolidone as solvent is heated at 180° C. in a microwave appliance (Biotage initiator, http://www.biotage.com/DynPage.aspx?id=22001) for 180 min. The crude mixture is absorbed on silica gel and, following separation by means of column chromatography, 0.034 g of 4-amino-2-{[(1R,2S)-2,6-dimethyl-2,3-dihydro-1H-inden-1-yl]amino}-6-(2-fluorophenyl)pyrimidine-5-carbonitrile with a melting point of 67-68° C. (12% yield, 95% purity) is obtained.

| Chemicophysical data: | |
| --- | --- |
| Compound | Description |
| 1.1 | wax-like; 1H-NMR (CDCl$_3$, 300 MHZ, δ in ppm): 1.60-2.00 (m, 2 * CH$_2$); 2.20 (s, 3H, CH$_3$); 2.25 (s, 3H, CH$_3$); 2.50 (m, 2H, CH$_2$); 3.10 (dd, 1H, CH); 5.20-5.90 (m, 4H, CH, NH$_2$, NH); 6.40 (s, 1H, PYR-H); 6.90 (s, 1H, Ar—H); 6.95 (s, 1H, Ar—H); |
| 1.17 | solid, m.p.: 166.4° C.; logp (HCOOH): 2.40; 1H-NMR (CDCl$_3$, 400 MHZ, δ in ppm): 1.25 (d, 3H, CH$_3$); 2.25 (m, 1H, 1H from CH$_2$); 2.30 (s, 3H, CH$_3$); 2.40 (br, 3H, CH$_3$); 2.50 (dd, 1H, 1H from CH$_2$); 3.05 (dd, 1H, CH); 5.15 (t, 1H, CH); 5.25 (br, 2H, NH$_2$); 5.45 (br, 1H, NH); 6.95-7.10 (m, 3H, Ar—H) |
| 1.18 | wax-like; 1H-NMR (CDCl$_3$, 400 MHZ, δ in ppm): 1.45 (m, 2H, CH$_2$); 1.85 (m, 2H, CH$_2$); 1.85 and 2.10 (in each case m, 1H, 1H from CH$_2$); 2.40 (br, 3H, CH$_3$); 2.85 (m, 2H, CH$_2$); 5.05-5.50 (m, 4H, CH, NH$_2$, NH); 7.05-7.20 (m, 4H, Ar—H) |
| 1.23 | solid; logp (HCOOH): 1.99; 1H-NMR (CDCl$_3$, 400 MHZ, δ in ppm): 1.25 (d, 3H, CH$_3$); 2.25 (m, 1H, 1H from CH$_2$); 2.40 (br, 3H, CH$_3$); 2.50 (m, 1H, 1H from CH$_2$); 3.10 (dd, 1H, CH); 5.05-5.50 (m, 4H, CH, NH$_2$, NH); 6.95-7.10 (m, 3H, Ar—H) |
| 1.24 | solid, m.p.: 153.3° C.; logp (HCOOH): 1.64; 1H-NMR (CDCl$_3$, 400 MHZ, δ in ppm): 1.85 and 2.65 (in each case m, 1H, 1H from CH$_2$); 2.40 (br, 3H, CH$_3$); 2.85 and 2.95 (in each case m, 1H, 1H from CH$_2$); 5.05-5.50 (m, 4H, CH, NH$_2$, NH); 7.15-7.30 (m, 4H, Ar—H) |
| 1.25 | solid, m.p.: 213.3° C.; logp (HCOOH): 1.55; 1H-NMR (CDCl$_3$, 400 MHZ, δ in ppm): 2.10 and 2.25 (in each case m, 1H, 1H from CH$_2$); 2.40 (br, 3H, CH$_3$); 4.15 and 4.25 (in each case m, 1H, 1H from CH$_2$); 5.05-5.50 (m, 4H, CH, NH$_2$, NH); 6.80-6.90 and 7.15-7.25 (in each case m, 4H, Ar—H) |

-continued

Chemicophysical data:

| Compound | Description |
|---|---|
| 1.26 | wax-like; logp (HCOOH): 1.66; 1H-NMR (CDCl$_3$, 400 MHZ, δ in ppm): 2.10 and 2.25 (in each case m, 1H, 1H from CH$_2$); 2.40 (br, 3H, CH$_3$); 4.25 and 4.35 (in each case m, 1H, 1H from CH$_2$); 5.15-5.55 (m, 4H, CH, NH$_2$, NH); 6.80 and 7.00 (in each case m, 3H, Ar—H) |
| 1.27 | solid, m.p.: 158.8° C.; logp (HCOOH): 2.51; 1H-NMR (CDCl$_3$, 400 MHZ, δ in ppm): 1.15 (d, 6H, CH$_3$); 2.10 and 2.25 (in each case m, 1H, 1H from CH$_2$); 2.40 (br, 3H, CH$_3$); 2.80 (sept., 1H, CH); 4.15 and 4.25 (in each case m, 1H, 1H from CH$_2$); 5.05-5.55 (m, 4H, CH, NH$_2$, NH); 6.80 (d, 1H, Ar—H); 7.05 (d, 2H, Ar—H) |
| 1.28 | wax-like; logp (HCOOH): 2.68; 1H-NMR (CDCl$_3$, 400 MHZ, δ in ppm): 1.20 (d, 6H, CH$_3$); 1.85 and 2.60 (in each case m, 1H, 1H from CH$_2$); 2.40 (br, 3H, CH$_3$); 2.80 (m, 3H, CH and CH$_2$); 5.05-5.55 (m, 4H, CH, NH$_2$, NH); 7.05 (m, 3H, Ar—H) |
| 1.29 | solid; m.p.: 205.8° C.; logp (HCOOH): 3.43; 1H-NMR (CDCl$_3$, 400 MHZ, δ in ppm): 1.85 (m, 3H, 1H from CH$_2$; CH$_2$); 2.05 (m, 1H, 1H from CH$_2$); 2.80 (m, 2H, CH$_2$); 5.25 (t, 1H, CH); 5.60 (br, 2H, NH$_2$); 5.80 (br, 1H, NH); 7.05-7.30 (m, 4H, Ar—H) |
| 1.30 | wax-like; logp (HCOOH): 1.92; 1H-NMR (CDCl$_3$, 400 MHZ, δ in ppm): 1.85 (m, 2H, CH$_2$); 1.85 and 2.05 (in each case m, 1H, 1H from CH$_2$); 2.85 (m, 2H, CH$_2$); 5.05-5.50 (m, 4H, CH, NH$_2$, NH); 7.05-7.20 (m, 4H, Ar—H); 8.30 (s, 1H, PYR-H) |
| 1.35 | wax-like; logp (HCOOH): 2.35; 1H-NMR (CDCl$_3$, 400 MHZ, δ in ppm): 1.25 (d, 3H, CH$_3$); 2.25 (m, 1H, 1H from CH$_2$); 2.30 (br, 3H, CH$_3$); 2.50 (m, 1H, 1H from CH$_2$); 3.10 (dd, 1H, CH); 5.20-5.90 (m, 4H, CH, NH$_2$, NH); 6.95-7.20 (m, 3H, Ar—H); 8.00 (s, 1H, PYR-H) |
| 1.37 | wax-like; logp (HCOOH): 1.32; 1H-NMR (CDCl$_3$, 400 MHZ, δ in ppm): 1.85 (m, 2H, CH$_2$); 1.85 and 2.05 (in each case m, 1H, 1H from CH$_2$); 2.80 (m, 2H, CH$_2$); 4.95-5.50 (m, 4H, CH, NH$_2$, NH); 7.05-7.20 (m, 4H, Ar—H); 8.40 (s, 1H, PYR-H) |
| 1.38 | wax-like; logp (HCOOH): 1.25; 1H-NMR (CDCl$_3$, 400 MHZ, δ in ppm): 1.25 (m, 3H, CH$_3$); 2.30 (br, 3H, CH$_3$); 2.50 (m, 2H, CH$_2$); 3.05 (dd, 1H, CH); 5.15 (t, 1H, CH); 5.60 (br, 2H, NH$_2$); 5.95 (d, 1H, PYR-H); 6.95-7.10 (m, 3H, Ar—H); 7.55 (d, 1H, PYR-H); 9.70 (br, 1H, NH); |
| 1.39 | wax-like; logp (HCOOH): 1.86; 1H-NMR (CDCl$_3$, 400 MHZ, δ in ppm): 0.25 (s, 9H, CH$_3$); 1.85 (m, 2H, CH$_2$); 1.85 and 2.05 (in each case m, 1H, 1H from CH$_2$); 2.80 (m, 2H, CH$_2$); 5.05-5.40 (m, 4H, CH, NH$_2$, NH); 7.05-7.30 (m, 4H, Ar—H); 8.00 (s, 1H, PYR-H) |
| 1.41 | wax-like; logp (HCOOH): 1.12; 1H-NMR (DMSO, 400 MHZ, δ in ppm): 1.15 (d, 3H, CH$_3$); 2.25 (m, 1H, 1H from CH$_2$); 2.30 (br, 3H, CH$_3$); 2.40 (m, 1H, 1H from CH$_2$); 2.90 (dd, 1H, CH); 4.85-6.60 (m, 5H, CH, NH$_2$, NH, PYR-H); 6.85-7.10 (m, 3H, Ar—H) |
| 1.46 | wax-like; logp (HCOOH): 1.39; 1H-NMR (CDCl$_3$, 400 MHZ, δ in ppm): 1.25 (d, 3H, CH$_3$); 2.25 (m, 1H, 1H from CH$_2$); 2.30 (s, 3H, CH$_3$); 2.45 (s, 3H, CH$_3$); 2.50 (m, 1H, 1H from CH$_2$); 3.00 (dd, 1H, CH); 4.85-5.60 (m, 4H, CH, NH$_2$, NH); 6.95-7.10 (m, 3H, Ar—H) |
| 1.51 | wax-like; 1H-NMR (CDCl$_3$, 400 MHZ, δ in ppm): 1.25 (d, 3H, CH$_3$); 2.00 (s, 3H, CH$_3$); 2.30 (s, 3H, CH$_3$); 2.50 (m, 2H, CH$_2$); 3.05 (dd, 1H, CH); 5.10 (t, 1H, CH); 5.20-5.70 (br, 2H, NH$_2$); 6.95 (s, 1H, Ar—H), 7.10 (dd, 2H, Ar—H), 7.45 (s, 1H, PYR-H); 9.50 (d, 1H, NH); |
| 1.56 | wax-like; logp (HCOOH): 1.20; 1H-NMR (CDCl$_3$, 400 MHZ, δ in ppm): 1.25 (d, 3H, CH$_3$); 2.15 (m, 1H, 1H from CH$_2$); 2.25 (s, 3H, CH$_3$); 2.50 (m, 1H, 1H from CH$_2$); 3.00 (dd, 1H, CH); 4.80 (br, 2H, NH$_2$); 5.00 (br, 1H, NH); 5.10 (t, 1H, CH); 6.95-7.05 (m, 3H, Ar—H); 7.80 (s, 1H, PYR-H); |
| 1.61 | solid, m.p.: 126.9° C.; logp (HCOOH): 3.07; 1H-NMR (CDCl$_3$, 400 MHZ, δ in ppm): 1.25 (m, 6H, 2*CH$_3$); 2.20 (m, 1H, 1H from CH$_2$); 2.30 (s, 3H, CH$_3$); 2.50 (m, 1H, 1H from CH$_2$); 2.75 (m, 2H, CH$_2$); 3.05 (dd, 1H, CH); 5.0-5.50 (m, 4H, CH, NH$_2$, NH); 6.95-7.05 (m, 3H, Ar—H); |
| 1.62 | wax-like; logp (HCOOH): 2.18; 1H-NMR (CDCl$_3$, 400 MHZ, δ in ppm): 1.25 (t, 3H, CH$_3$); 1.85 (m, 1H, 1H from CH$_2$); 2.65 (m, 3H, CH$_2$ and 1H from CH$_2$); 2.90 (m, 1H, 1H from CH$_2$); 3.00 (m, 1H, 1H from CH$_2$); 5.0-5.50 (m, 4H, CH, NH$_2$, NH); 6.95-7.05 (m, 4H, Ar—H); |
| 1.63 | wax-like; logp (HCOOH): 2.49; 1H-NMR (CDCl$_3$, 400 MHZ, δ in ppm): 1.25 (t, 3H, CH$_3$); 1.85 (m, 3H, CH$_2$ and 1H from CH$_2$); 2.10 (m, 1H, 1H from CH$_2$); 2.60-2.90 (m, 4H, CH$_2$ and 2*1H from CH$_2$); 5.0-5.50 (m, 4H, CH, NH$_2$, NH); 6.95-7.05 (m, 4H, Ar—H); |
| 1.64 | wax-like; logp (HCOOH): 3.90; 1H-NMR (CDCl$_3$, 400 MHZ, δ in ppm): 1.25 (m, 9H, 3*CH$_3$); 2.25 (m, 1H, 1H from CH$_2$); 2.30 (s, 3H, CH$_3$); 2.50 (m, 1H, 1H from CH$_2$); 3.05 (dd, 1H, CH); 3.15 (m, 1H, CH); 5.00-5.50 (m, 4H, CH, NH$_2$, NH); 6.95-7.05 (m, 3H, Ar—H); |
| 1.65 | wax-like; 1H-NMR (CDCl$_3$, 400 MHZ, δ in ppm): 1.25 (m, 6H, 2*CH$_3$); 1.85 (m, 3H, CH$_2$ and 1H from CH$_2$); 2.60 (m, 1H, 1H from CH$_2$); 2.80-3.20 (m, 3H, CH and 2*1H from CH$_2$); 5.0-5.50 (m, 4H, CH, NH$_2$, NH); 6.95-7.05 (m, 4H, Ar—H); |
| 1.66 | wax-like; logp (HCOOH): 3.34; 1H-NMR (CDCl$_3$, 400 MHZ, δ in ppm): 1.25 (m, 6H, 2*CH$_3$); 1.85 (m, 3H, CH$_2$ and 1H from CH$_2$); 2.10 (m, 1H, 1H from CH$_2$); 2.80 (m, 2H, 2*CH); 2.80 (m, 1H, CH); 5.0-5.50 (m, 4H, CH, NH$_2$, NH); 6.95-7.05 (m, 4H, Ar—H); |
| 1.67 | wax-like; logp (HCOOH): 1.30; 1H-NMR (CDCl$_3$, 400 MHZ, δ in ppm): 1.25 (m, 3H, CH$_3$); 2.25 (m, 1H, 1H from CH$_2$); 2.30 (s, 3H, CH$_3$); 2.50 (m, 1H, 1H from CH$_2$); 3.05 (dd, 1H, CH); 3.15 (m, 1H, CH); 5.00-5.40 (m, 4H, CH, NH$_2$, NH); 6.95-7.05 (m, 3H, Ar—H); 7.90 (s, 1H, PYR-H); |
| 1.75 | wax-like; 1H-NMR (CDCl$_3$, 400 MHZ, δ in ppm): 1.25 (m, 3H, CH$_3$); 2.25 (m, 1H, 1H from CH$_2$); 2.30 (s, 3H, CH$_3$); 2.50 (m, 1H, 1H from CH$_2$); 3.0 (dd, 1H, CH); 5.00-5.40 (m, 4H, CH, NH$_2$, NH); 5.85 (s, 1H, PYR-H); 6.95-7.05 (m, 3H, Ar—H); |
| 1.76 | wax-like; 1H-NMR (CDCl$_3$, 400 MHZ, δ in ppm): 1.85 (m, 2H, 2*1H from CH$_2$); 2.10 (m, 1H, 1H from CH$_2$); 2.80 (m, 2H, 2*CH); 2.80 (m, 1H, CH); 5.0-5.50 (m, 4H, CH, NH$_2$, NH); 6.95-7.05 (m, 4H, Ar—H); |

-continued

Chemicophysical data:

| Compound | Description |
|---|---|
| 1.77 | solid; logp (HCOOH): 3.83; 1H-NMR (CDCl$_3$, 400 MHZ, δ in ppm): 1.25 (m, 3H, CH$_3$); 2.25 (m, 1H, 1H from CH$_2$); 2.30 (s, 3H, CH$_3$); 2.35 (s, 3H, CH$_3$); 2.50 (m, 1H, 1H from CH$_2$); 3.05 (dd, 1H, CH); 5.20 (t, 1H, CH); 5.50 (br, 2H, NH$_2$); 6.25 (br, 1H, NH); 6.95-7.05 (m, 3H, Ar—H); 7.25-7.40 (m, 4H, Ar—H); |
| 1.78 | solid; logp (HCOOH): 3.41; 1H-NMR (CDCl$_3$, 400 MHZ, δ in ppm): 1.85-2.05 (br, 4H, CH$_2$, CH$_2$); 2.40 (s, 3H, CH$_3$); 2.80 (m, 2H, CH$_2$); 4.95-5.50 (m, 3H, CH, NH$_2$); 6.40 (br, 1H, NH); 7.05-7.45 (m, 8H, Ar—H); |
| 1.79 | wax-like; 1H-NMR (CDCl$_3$, 400 MHZ, δ in ppm): 1.85 (br, 1H, 1H from CH$_2$); 2.40 (br, 3H, CH$_3$); 2.45 (br, 1H, 1H from CH$_2$); 2.80 (m, 2H, CH$_2$); 5.20-5.70 (m, 4H, CH, NH$_2$); 7.15-7.45 (m, 8H, Ar—H); |
| 1.80 | wax-like; 1H-NMR (CDCl$_3$, 400 MHZ, δ in ppm): 1.25 (m, 3H, CH$_3$); 2.25 (m, 1H, 1H from CH$_2$); 2.30 (s, 3H, CH$_3$); 2.35 (s, 3H, CH$_3$); 2.50 (m, 1H, 1H from CH$_2$); 3.05 (dd, 1H, CH); 5.20-5.70 (m, m, 4H, CH, NH$_2$, NH); 6.95-7.10 (m, 3H, Ar—H); 7.60 (m, 1H, Ar—H); 7.75 (m, 1H, Ar—H); 8.15 (m, 2H, Ar—H); |
| 1.81 | wax-like; 1H-NMR (CDCl$_3$, 400 MHZ, δ in ppm): 1.85-2.05 (br, 4H, CH$_2$, CH$_2$); 2.80 (m, 2H, CH$_2$); 5.20-5.70 (m, m, 4H, CH, NH$_2$, NH); 6.95-7.10 (m, 3H, Ar—H); 7.60 (m, 1H, Ar—H); 7.75 (m, 1H, Ar—H); 8.15 (m, 2H, Ar—H); |
| 1.82 | wax-like; 1H-NMR (CDCl$_3$, 400 MHZ, δ in ppm): 1.85 (br, 1H, 1H from CH$_2$); 2.65 (br, 1H, 1H from CH$_2$); 2.90 (m, 2H, CH$_2$); 5.20-5.70 (m, 4H, CH, NH$_2$); 6.95-7.10 (m, 3H, Ar—H); 7.60 (m, 1H, Ar—H); 7.75 (m, 1H, Ar—H); 8.15 (m, 2H, Ar—H); |
| 1.83 | wax-like; logp (HCOOH): 1.71; 1H-NMR (CDCl$_3$, 400 MHZ, δ in ppm): 1.25 (m, 3H, CH$_3$); 2.25 (m, 1H, 1H from CH$_2$); 2.30 (s, 3H, CH$_3$); 2.50 (m, 1H, 1H from CH$_2$); 3.05 (dd, 1H, CH); 5.10-5.70 (m, m, 4H, CH, NH$_2$, NH); 6.15 (s, 1H, PYR-H); 6.95-7.10 (m, 3H, Ar—H); 7.50 (m, 3H, Ar—H); 7.75 (m, 2H, Ar—H); |
| 1.84 | wax-like; logp (HCOOH): 2.63; 1H-NMR (CDCl$_3$, 400 MHZ, δ in ppm): 0.75 (m, 2H, CH$_2$); 1.45 (m, 2H, CH$_2$); 1.55 (br, 3H, CH$_3$); 1.85 (br, 3H, 1H from CH$_2$, CH$_2$); 2.10 (br, 1H, 1H from CH$_2$); 2.85 (m, 2H, CH$_2$); 5.20-5.70 (m, 4H, CH, NH$_2$); 6.95-7.10 (m, 3H, Ar—H); |
| 1.85 | wax-like; logp (HCOOH): 4.02; 1H-NMR (CDCl$_3$, 400 MHZ, δ in ppm): 1.70-2.10 (br, 6H, 3*CH$_2$); 2.20-2.50 (br, 2H, CH$_2$); 2.30 (s, 3H, CH$_3$); 2.85 (m, 2H, CH$_2$); 5.30 (t, 1H, CH); 5.60 (br, 2H, NH$_2$); 6.60 (br, 1H, NH); 6.95-7.10 (m, 7H, Ar—H); |
| 1.86 | wax-like; logp (HCOOH): 5.15; 1H-NMR (CDCl$_3$, 400 MHZ, δ in ppm): 1.25 (br, 2H, CH$_2$); 1.80-2.10 (br, 6H, 3*CH$_2$); 2.85 (m, 2H, CH$_2$); 5.20-5.70 (m, 4H, CH, NH$_2$); 6.95-7.50 (m, 6H, Ar—H); |
| 1.87 | wax-like; logp (HCOOH): 1.37; 1H-NMR (CDCl$_3$, 400 MHZ, δ in ppm): 1.25 (d, 3H, CH$_3$); 2.20 (m, 1H, 1H from CH$_2$); 2.30 (s, 3H, CH$_3$); 2.50 (m, 1H, 1H from CH$_2$); 3.00 (dd, 1H, CH); 5.00-5.20 (m, 4H, NH$_2$, NH, CH); 6.95-7.10 (m, 3H, Ar—H); 8.10 (br, 1H, PYR-H); |
| 1.91 | wax-like; logp (HCOOH): 1.66; 1H-NMR (CDCl$_3$, 400 MHZ, δ in ppm): 1.25 (d, 3H, CH$_3$); 2.20 (m, 1H, 1H from CH$_2$); 2.30 (s, 3H, CH$_3$); 2.50 (m, 1H, 1H from CH$_2$); 3.00 (s, 6H, 2*CH$_3$); 3.05 (dd, 1H, CH); 4.20 (br, 2H, NH$_2$); 4.70 (d, 1H, NH); 5.00 (s, 1H, PYR-H); 5.30 (t, 1H, CH); 5.20-5.70 (br, 2H, NH$_2$); 7.00 (dd, 2H, Ar—H); 7.10 (s, 1H, Ar—H); |
| 1.93 | wax-like; logp (HCOOH): 3.31; 1H-NMR (CDCl$_3$, 400 MHZ, δ in ppm): 0.75 (m, 2H, CH$_2$); 1.25 (d, 3H, CH$_3$); 1.50 (s, 3H, CH$_3$); 1.55 (m, 2H, CH$_2$); 2.30 (m, 1H, 1H from CH$_2$); 2.30 (s, 3H, CH$_3$); 2.50 (m, 1H, 1H from CH$_2$); 3.05 (dd, 1H, CH); 4.20 (br, 2H, NH$_2$); 4.70 (d, 1H, NH); 5.10-5.50 (m, 4H, CH, NH$_2$); 6.95 (s, 1H, Ar—H); 7.00 (dd, 2H, Ar—H); |
| 1.94 | wax-like; logp (HCOOH): 5.55; 1H-NMR (CDCl$_3$, 400 MHZ, δ in ppm): 1.25 (d, 3H, CH$_3$); 1.30 (m, 2H, CH$_2$); 1.80-2.00 (m, 2H, CH$_2$); 2.30 (s, 3H, CH$_3$); 2.50 (m, 1H, 1H from CH$_2$); 3.05 (dd, 1H, CH); 4.20 (br, 2H, NH$_2$); 4.70 (d, 1H, NH); 5.10-6.20 (m, 4H, CH, NH$_2$); 6.95-7.50 (m, 6H, Ar—H); |
| 1.96 | solid, m.p.: 132-133° C.; logp (HCOOH): 2.46; 1H-NMR (CDCl$_3$, 400 MHZ, δ in ppm): 1.00 (t, 3H, CH$_3$); 1.50 (m, 1H, 1H from CH$_2$); 1.80 (m, 1H, 1H from CH$_2$); 2.10 (m, 1H, 1H from CH$_2$); 2.30 (br, 3H, CH$_3$); 2.50 (m, 1H, 1H from CH$_2$); 3.10 (dd, 1H, CH); 5.00-5.80 (m, 4H, NH$_2$, NH, CH); 6.95-7.10 (m, 4H, Ar—H); |
| 1.97 | solid, m.p.: 124-125° C.; logp (HCOOH): 1.18; 1H-NMR (CDCl$_3$, 400 MHZ, δ in ppm): 1.80 (m, 3H, 3H from CH$_2$); 2.10 (m, 1H, 1H from CH$_2$); 2.80 (m, 2H, 2H from CH$_2$); 4.90-5.60 (m, 4H, NH$_2$, NH, CH); 7.00-7.40 (m, 4H, Ar—H); 7.90 (br, 1H, PYR-H); |
| 1.98 | wax-like, logp (HCOOH): 2.28; 1H-NMR (CDCl$_3$, 400 MHZ, δ in ppm): 0.25 (s, 9H, CH$_3$); 1.25 (d, 3H, CH$_3$); 2.20 (m, 1H, 1H from CH$_2$); 2.30 (s, 3H, CH$_3$); 2.50 (m, 1H, 1H from CH$_2$); 3.05 (dd, 1H, CH); 5.2-5.4 (4H, NH$_2$, NH, CH); 7.00 (dd, 2H, Ar—H); 7.10 (s, 1H, Ar—H); 8.1 (br, 1H, PYR-H); |
| 1.104 | solid, m.p.: 67-68° C.; logp (HCOOH): 3.65; 1H-NMR (CDCl$_3$, 400 MHZ, δ in ppm): 1.25 (d, 3H, CH$_3$); 2.30 (s, 3H, CH$_3$); 2.40 (m, 1H, 1H from CH$_2$); 2.50 (m, 1H, 1H from CH$_2$); 3.05 (dd, 1H, CH); 5.20 (br, 1H, CH); 5.60 (br, 2H, NH$_2$); 6.00 (br, 1H, NH) 7.00-7.60 (m, 7H, Ar—H); |
| 1.105 | wax-like; logp (HCOOH): 1.27; 1H-NMR (CDCl$_3$, 400 MHZ, δ in ppm): 1.30 (d, 3H, CH$_3$); 2.20 (m, 1H, 1H from CH$_2$); 2.30 (s, 3H, CH$_3$); 2.50 (m, 1H, 1H from CH$_2$); 3.00 (dd, 1H, CH); 5.00-5.20 (m, 4H, NH$_2$, NH, CH); 6.95-7.10 (m, 3H, Ar—H); 7.90 (br, 1H, PYR-H); |
| 1.106 | solid; logp (HCOOH): 1.13; 1H-NMR (CDCl$_3$, 400 MHZ, δ in ppm): 1.80 (m, 3H, 3H from CH$_2$); 2.10 (m, 1H, 1H from CH$_2$); 2.80 (m, 2H, 2H from CH$_2$); 4.90-5.40 (m, 4H, NH$_2$, NH, CH); 7.00-7.40 (m, 4H, Ar—H); 7.90 (br, 1H, PYR-H); |
| 1.107 | wax-like, logp (HCOOH): 2.11; 1H-NMR (CDCl$_3$, 400 MHZ, δ in ppm): 1.25 (d, 3H, CH$_3$); 1.60 (m, 1H, 1H from CH$_2$); 2.30 (s, 3H, CH$_3$); 2.50 (m, 1H, 1H from CH$_2$); 3.05 (dd, 1H, CH); 5.0-5.6 (4H, NH$_2$, NH, CH); 7.00 (dd, 2H, Ar—H); 7.10 (s, 1H, Ar—H); 8.0-8.40 (br, 1H, PYR-H); |
| 1.108 | solid, m.p.: 130.8° C., logp (HCOOH): 1.64; 1H-NMR (CDCl$_3$, 400 MHZ, δ in ppm): 1.85 (m, 2H, CH$_2$); 1.85 and 2.05 (in each case m, 1H, 1H from CH$_2$); 2.80 (m, 2H, CH$_2$); 4.95-5.50 (m, 4H, CH, NH$_2$, NH); 7.05-7.20 (m, 4H, Ar—H); 8.0-8.40 (br, 1H, PYR-H) |

-continued

| Chemicophysical data: | |
|---|---|
| Compound | Description |
| 1.116 | wax-like; logp (HCOOH): 1.09; 1H-NMR (CDCl$_3$, 400 MHZ, δ in ppm): 1.80 (m, 3H, 3H from CH$_2$); 2.10 (m, 1H, 1H from CH$_2$); 2.80 (m, 2H, 2H from CH$_2$); 3.40 (s, 1H, 1H from CCH); 5.00-5.30 (m, 4H, NH$_2$, NH, CH); 7.00-7.40 (m, 4H, Ar—H); 8.10 (br, 1H, PYR-H); |
| 1.118 | wax-like; logp (HCOOH): 2.96; 1H-NMR (CDCl$_3$, 400 MHZ, δ in ppm): 1.30 (d, 3H, CH$_3$); 2.25 (m, 1H, 1H from CH$_2$); 2.30 (s, 3H, CH$_3$); 2.55 (m, 1H, 1H from CH$_2$); 3.10 (dd, 1H, CH); 3.95 (s, 3H, CH$_3$); 5.20 (br, 2H, NH$_2$); 5.50 (br, 1H, CH); 6.80 (br, 1H, PYR-H); 6.95-7.10 (m, 3H, Ar—H); 7.60 (br, 1H, NH); |
| 1.119 | solid, m.p.: 99° C.; logp (HCOOH): 1.43; 1H-NMR (CDCl$_3$, 400 MHZ, δ in ppm): 1.25 (d, 3H, CH$_3$); 2.20 (m, 1H, 1H from CH$_2$); 2.30 (s, 3H, CH$_3$); 2.50 (m, 1H, 1H from CH$_2$); 3.05 (dd, 1H, CH); 3.4 (s, 1H, C≡CH); 5.2-5.4 (4H, NH$_2$, NH, CH); 7.00 (dd, 2H, Ar—H); 7.10 (s, 1H, Ar—H); 8.1 (br, 1H, PYR-H); |
| 1.129 | solid, m.p.: 142-143° C.; logp (HCOOH): 2.43; 1H-NMR (CDCl$_3$, 400 MHZ, δ in ppm): 1.00 (t, 3H, CH$_3$); 1.50 (m, 1H, 1H from CH$_2$); 1.80 (m, 1H, 1H from CH$_2$); 2.10 (m, 1H, 1H from CH$_2$); 2.50 (m, 1H, 1H from CH$_2$); 3.10 (dd, 1H, CH); 5.00-5.80 (m, 4H, NH$_2$, NH, CH); 7.15-7.30 (m, 4H, Ar—H); 8.00 and 8.30 (br, 1H, PYR-H); |
| 1.184 | wax-like; logp (HCOOH): 1.58; 1H-NMR (CDCl$_3$, 400 MHZ, δ in ppm): 1.30 (d, 3H, CH$_3$); 2.25 (m, 1H, 1H from CH$_2$); 2.30 (s, 3H, CH$_3$); 2.40 (br, 3H, CH$_3$); 2.55 (m, 1H, 1H from CH$_2$); 3.00 (dd, 1H, CH); 5.20-5.80 (m, 3H, NH$_2$, CH); 6.95-7.10 (m, 3H, Ar—H); 8.40-8.80 (br, 2H, NH, PYR-H); |
| 1.212 | wax-like; logp (HCOOH): 2.54; 1H-NMR (CDCl$_3$, 400 MHZ, δ in ppm): 1.80-2.10 (m, 4H, 4H from CH$_2$); 2.80 (m, 2H, 2H from CH$_2$); 3.95 (br, 3H, CH$_3$); 5.30 (br, 2H, NH$_2$); 5.50 (br, 1H, CH); 6.80 (br, 1H, PYR-H); 6.95-7.10 (m, 3H, Ar—H); 7.60 (br, 1H, NH); |
| 1.214 | wax-like; logp (HCOOH): 1.59; 1H-NMR (CDCl$_3$, 400 MHZ, δ in ppm): 1.30 (d, 3H, CH$_3$); 2.30 (s, 3H, CH$_3$); 2.35 (m, 1H, 1H from CH$_2$); 2.55 (m, 1H, 1H from CH$_2$); 3.00 (dd, 1H, CH); 5.20-6.30 (m, 5H, NH$_2$, NH, CH, PYR-H); 6.80 (t, 1H, CF$_2$H); 6.95-7.10 (m, 3H, Ar—H); |
| 1.216 | wax-like; logp (HCOOH): 2.18; 1H-NMR (CDCl$_3$, 400 MHZ, δ in ppm): 1.80 (m, 1H, 1H from CH$_2$); 2.55 (m, 1H, 1H from CH$_2$); 2.85 (m, 1H, 1H from CH$_2$); 3.10 (m, 1H, 1H from CH$_2$); 5.20-5.80 (m, 4H, NH$_2$, NH, CH); 7.05-7.25 (m, 3H, Ar—H); 8.10 and 8.30 (br, 1H, PYR-H); |
| 1.217 | wax-like; logp (HCOOH): 2.21; 1H-NMR (CDCl$_3$, 400 MHZ, δ in ppm): 1.80 (m, 1H, 1H from CH$_2$); 2.50 (s, 3H, CH$_3$); 2.55 (m, 1H, 1H from CH$_2$); 2.85 (m, 1H, 1H from CH$_2$); 3.10 (m, 1H, 1H from CH$_2$); 5.20-5.80 (m, 4H, NH$_2$, NH, CH); 7.05-7.25 (m, 3H, Ar—H); |
| 1.221 | wax-like; logp (HCOOH): 1.98; 1H-NMR (CDCl$_3$, 400 MHZ, δ in ppm): 1.25 (d, 3H, CH$_3$); 2.25 (m, 1H, 1H from CH$_2$); 2.30 (s, 3H, CH$_3$); 2.55 (m, 1H, 1H from CH$_2$); 3.00 (dd, 1H, CH); 3.80 (s, 3H, OCH$_3$); 5.20-5.40 (m, 4H, NH$_2$, NH, CH,); 6.85-7.30 (m, 7H, Ar—H); 8.10 (br, 1H, PYR-H); |
| 1.222 | wax-like; logp (HCOOH): 1.04; 1H-NMR (CDCl$_3$, 400 MHZ, δ in ppm): 1.25 (d, 3H, CH$_3$); 2.25 (m, 1H, 1H from CH$_2$); 2.30 (s, 3H, CH$_3$); 2.50 (m, 1H, 1H from CH$_2$); 3.00 (dd, 1H, CH); 4.50 (s, 2H, CH$_2$OH); 5.20-5.40 (m, 4H, NH$_2$, NH, CH,); 6.95-7.10 (m, 3H, Ar—H); 8.10 (br, 1H, PYR-H); |
| 1.224 | wax-like; logp (HCOOH): 3.37; 1H-NMR (CDCl$_3$, 400 MHZ, δ in ppm): 1.80 (m, 1H, 1H from CH$_2$); 2.10 (m, 1H, 1H from CH$_2$); 2.40 and 2.45 (2s, 3H, CH$_3$); 2.70 and 2.80 (2s, 3H, CH$_3$); 2.85 (m, 2H, 2H from CH$_2$); 5.10 and 5.20 (2br, 2H, NH$_2$); 6.10 and 6.35 (2t, 1H, CH); 7.00-7.25 (m, 4H, Ar—H); |
| 1.237 | wax-like; logp (HCOOH): 1.50; 1H-NMR (CDCl$_3$, 400 MHZ, δ in ppm): 1.80 (m, 1H, 1H from CH$_2$); 2.65 (m, 1H, 1H from CH$_2$); 2.85 (m, 1H, 1H from CH$_2$); 3.10 (dd, 1H, 1H from CH$_2$); 5.00-5.60 (m, 4H, NH$_2$, NH, CH); 7.15-7.25 (m, 4H, Ar—H); 8.10 and 8.30 (br, 1H, PYR-H); |
| 1.238 | wax-like; logp (HCOOH): 2.02; 1H-NMR (CDCl$_3$, 400 MHZ, δ in ppm): 1.15 (t, 3H, CH$_3$); 2.05 (m, 1H, 1H from CH$_2$); 2.20 (m, 1H, 1H from CH$_2$); 2.50 (t, 3H, CH$_3$); 4.15 (m, 1H, 1H from CH$_2$O); 4.25 (m, 1H, 1H from CH$_2$O); 5.10-5.20 (m, 2H, NH$_2$); 5.50 (br, 1H, CH); 6.20 (br, 1H, NH); 6.80 (d, 1H, Ar—H); 7.00-7.10 (m, 2H, Ar—H); 7.80 and 8.20 (br, 1H, PYR-H); |
| 1.239 | wax-like; logp (HCOOH): 1.46 |
| 1.241 | wax-like; logp (HCOOH): 2.83; 1H-NMR (CDCl$_3$, 400 MHZ, δ in ppm): 1.30 (s, 3H, CH$_3$); 1.40 (s, 3H, CH$_3$); 1.80 (m, 1H, 1H from CH$_2$); 2.25 (m, 1H, 1H from CH$_2$); 5.00-5.50 (m, 4H, NH$_2$, NH, CH); 6.80 (d, 1H, Ar—H); 7.05 (d, 1H, Ar—H); 8.15 (br, 1H, PYR-H); |
| 1.243 | wax-like; logp (HCOOH): 1.93; 1H-NMR (CDCl$_3$, 400 MHZ, δ in ppm): 0.95 (d, 3H, CH$_3$); 2.55 (m, 1H, 1H from CH$_2$); 2.85 (m, 1H, 1H from CH$_2$); 3.05 (dd, 1H, CH); 4.90-5.60 (m, 4H, NH$_2$, NH, CH,); 6.85-7.10 (m, 3H, Ar—H); 8.10-8.30 (br, 1H, PYR-H); |
| 1.245 | wax-like; logp (HCOOH): 1.93; 1H-NMR (CDCl$_3$, 400 MHZ, δ in ppm): 1.80 (m, 1H, 1H from CH$_2$); 2.65 (m, 1H, 1H from CH$_2$); 2.85 (m, 1H, 1H from CH$_2$); 3.00 (dd, 1H, 1H from CH$_2$); 5.00-5.60 (m, 4H, NH$_2$, NH, CH); 7.15-7.25 (m, 3H, Ar—H); 8.10-8.30 (br, 1H, PYR-H); |
| 1.245 | wax-like; logp (HCOOH): 1.68; 1H-NMR (CDCl$_3$, 400 MHZ, δ in ppm): 1.25 (d, 3H, CH$_3$); 2.25 (m, 1H, 1H from CH$_2$); 2.30 (s, 3H, Ar—CH$_3$); 2.50 (m, 1H, 1H from CH$_2$); 2.70 (s, 3H, Het-CH$_3$); 3.05 (dd, 1H, CH); 5.10-5.30 (m, 4H, NH$_2$, NH, CH); 6.95-7.10 (m, 3H, Ar—H); 7.30 (s, 1H, Het-H); 8.10-8.20 (br, 1H, PYR-H); |
| 1.247 | wax-like; logp (HCOOH): 2.60; 1H-NMR (CDCl$_3$, 400 MHZ, δ in ppm): 1.25 (d, 3H, CH$_3$); 2.30 (s, 3H, Ar—CH$_3$); 2.50 (m, 2H, 2H from CH$_2$); 3.05 (dd, 1H, CH); 5.10 (m, 1H, CH); 6.00 (br, 2H, NH$_2$); 6.95-7.10 (m, 3H, Ar—H); 7.50-7.70 (m, 4H, Ar—H); 7.70 (s, 1H, NH); 7.90 (s, 1H, PYR-H); |
| 1.248 | wax-like; logp (HCOOH): 2.71; 1H-NMR (CDCl$_3$, 400 MHZ, δ in ppm): 1.25 (d, 3H, CH$_3$); 2.30 (s, 3H, Ar—CH$_3$); 2.50 (m, 2H, 2H from CH$_2$); 3.05 (dd, 1H, CH); 5.15 (m, 1H, CH); 6.00 (br, 2H, NH$_2$); 6.95-7.60 (m, 7H, Ar—H, NH); 7.95 (s, 1H, PYR-H); |

-continued

Chemicophysical data:

| Compound | Description |
|---|---|
| 1.249 | wax-like; logp (HCOOH): 1.73; 1H-NMR (CDCl$_3$, 400 MHZ, δ in ppm): 1.00 (d, 6H, 2*CH$_3$); 1.25 (d, 3H, CH$_3$); 1.90 (m, 1H, CH(CH$_3$)$_2$); 2.20 (m, 1H, 1H from CH$_2$); 2.30 (s, 3H, Ar—CH$_3$); 2.40 (d, 2H, CCCH$_2$); 2.50 (m, 1H, 1H from CH$_2$); 3.05 (dd, 1H, CH); 5.10-5.30 (m, 4H, NH$_2$, NH, CH); 6.95-7.10 (m, 3H, Ar—H); 7.95 (s, 1H, PYR-H); |
| 1.251 | wax-like; logp (HCOOH): 1.48; 1H-NMR (CDCl$_3$, 400 MHZ, δ in ppm): 1.00 (t, 3H, CH$_3$); 1.25 (d, 3H, CH$_3$); 1.80 (m, 2H, CH$_2$CH$_3$); 2.20 (m, 1H, 1H from CH$_2$); 2.30 (s, 3H, Ar—CH$_3$); 2.50 (m, 1H, 1H from CH$_2$); 3.05 (dd, 1H, CH); 4.55 (m, 1H, CHOH); 5.10-5.30 (m, 4H, NH$_2$, NH, CH); 6.95-7.10 (m, 3H, Ar—H); 8.10 (br, 1H, PYR-H); |
| 1.252 | wax-like; logp (HCOOH): 1.59; 1H-NMR (CDCl$_3$, 400 MHZ, δ in ppm): 1.25 (d, 3H, CH$_3$); 2.10 (s, 3H, C(=O)—CH$_3$); 2.20 (m, 1H, 1H from CH$_2$); 2.30 (s, 3H, Ar—CH$_3$); 2.50 (m, 1H, 1H from CH$_2$); 3.00 (dd, 1H, CH); 4.90 (s, 2H, CH2O); 5.10-5.30 (m, 4H, NH$_2$, NH, CH); 6.95-7.10 (m, 3H, Ar—H); 8.10 (br, 1H, PYR-H); |
| 1.254 | wax-like; logp (HCOOH): 1.75; 1H-NMR (CDCl$_3$, 400 MHZ, δ in ppm): 2.10 (s, 3H, C(=O)—CH$_3$); 2.30 (s, 3H, Ar—CH$_3$); 2.65 (m, 1H, 1H from CH$_2$); 2.80 (m, 1H, 1H from CH$_2$); 2.90 (dd, 1H, CH); 5.00-5.70 (m, 4H, NH$_2$, NH, CH); 6.95-7.10 (m, 3H, Ar—H); 8.10-8.30 (br, 1H, PYR-H); |
| 1.255 | wax-like; logp (HCOOH): 2.03; 1H-NMR (CDCl$_3$, 400 MHZ, δ in ppm): 2.10-2.65 (m, 10H); 2.50 (m, 3H); 2.80 (m, 2H, 2H from CH$_2$); 5.00-5.50 (m, 4H, NH$_2$, NH, CH); 7.05-7.40 (m, 4H, Ar—H); |
| 1.257 | solid, m.p.: 171-172° C.; logp (HCOOH): 1.04; 1H-NMR (CDCl$_3$, 400 MHZ, δ in ppm): 2.05 (m, 1H, 1H from CH$_2$); 3.35 (m, 1H, 1H from CH$_2$); 4.45 (m, 1H, 1H from CHOH); 4.80-6.10 (m, 5H, NH$_2$, NH, CH, OH); 7.10-7.25 (m, 4H, Ar—H); 8.00-8.30 (br, 1H, PYR-H); |
| 1.261*HCl | solid, m.p.: 225-226° C.; 1H-NMR (CDCl$_3$, 400 MHZ, δ in ppm): 1.25 (d, 3H, CH$_3$); 2.30 (s, 3H, Ar—CH$_3$); 2.50 (m, 2H, 2H from CH$_2$); 3.10 (m, 1H, CH); 5.15 (t, 1H, CH); 6.00 (br, 2H, NH$_2$); 6.90 (s, 1H, Ar—H); 7.00-7.10 (dd, 2H, Ar—H); 8.00 (s, 1H, PYR-H); 8.70 (s, 1H, NH); |
| 1.266*HCl | solid; 1H-NMR (CDCl$_3$, 400 MHZ, δ in ppm): 1.25 (d, 3H, CH$_3$); 2.25 (s, 3H, Ar—CH$_3$); 2.50 (m, 2H, 2H from CH$_2$); 2.75 (s, 3H, PYR-CH$_3$); 3.10 (m, 1H, CH); 5.15 (t, 1H, CH); 6.20 (br, 2H, NH$_2$); 6.90 (s, 1H, Ar—H); 7.00-7.10 (dd, 2H, Ar—H); 8.70 (s, 1H, NH); |
| 1.271 | wax-like; logp (HCOOH): 2.60; 1H-NMR (CDCl$_3$, 400 MHZ, δ in ppm): 1.85 (m, 3H, 3H from CH$_2$); 2.00 (m, 1H, 1H from CH$_2$); 2.25 (s, 3H, Ar—CH$_3$); 2.30 (s, 3H, Ar—CH$_3$); 2.60 (m, 2H, 2H from CH$_2$); 5.10-5.90 (m, 4H, NH$_2$, NH, CH); 6.90-7.00 (m, 2H, Ar—H); 8.10-8.40 (m, 1H, PYR-H); |
| 1.273 | wax-like; logp (HCOOH): 2.57; 1H-NMR (CDCl$_3$, 400 MHZ, δ in ppm): 1.85 (m, 3H, 3H from CH$_2$); 2.00 (m, 1H, 1H from CH$_2$); 2.25 (s, 3H, Ar—CH$_3$); 2.30 (s, 3H, Ar—CH$_3$); 2.40 (s, 3H, PYR-CH$_3$); 2.60 (m, 2H, 2H from CH$_2$); 5.10-5.90 (m, 4H, NH$_2$, NH, CH); 6.90-7.00 (2s, 2H, Ar—H); |
| 1.274 | wax-like; logp (HCOOH): 2.07; 1H-NMR (CDCl$_3$, 400 MHZ, δ in ppm): 1.70-2.20 (m, 8H, 8H from CH$_2$); 2.70-2.90 (m, 4H, 4H from CH$_2$); 5.00-5.90 (m, 5H, NH$_2$, NH, 2*CH); 6.60 (m, 1H, PYR-H); 7.10-7.50 (m, 8H, Ar—H); 7.70 (br, 1H, C(=O)NH); |
| 1.255 | wax-like; logp (HCOOH): 2.03; 1H-NMR (CDCl$_3$, 400 MHZ, δ in ppm): 2.10-2.65 (m, 10H); 2.50 (m, 3H); 2.80 (m, 2H, 2H from CH$_2$); 5.00-5.50 (m, 4H, NH$_2$, NH, CH); 7.05-7.40 (m, 4H, Ar—H); |

B. Formulation Examples a) A dusting composition is obtained by mixing 10 parts by weight of a compound of the formula (I) and/or salts thereof and 90 parts by weight of talc as inert substance, and comminuting in a crushing mill.

b) A readily water-dispersible, wettable powder is obtained by mixing 25 parts by weight of a compound of the formula (I) and/or salts thereof, 64 parts by weight of kaolin-containing quartz as inert substance, 10 parts by weight of potassium lignosulfonate and 1 part by weight of sodium oleoylmethyltaurate as wetting agent and dispersant and grinding in a pin mill.

c) A readily water-dispersible dispersion concentrate is obtained by mixing 20 parts by weight of a compound of the formula (I) and/or salts thereof with 6 parts by weight of alkylphenol polyglycol ether (®Triton X 207), 3 parts by weight of isotridecanol polyglycol ether (8 EO) and 71 parts by weight of paraffinic mineral oil (boiling range e.g. ca. 255 to more than 277° C.) and grinding in an attrition ball mill to a fineness below 5 microns.

d) An emulsifiable concentrate is obtained from 15 parts by weight of a compound of the formula (I) and/or salts thereof, 75 parts by weight of cyclohexanone as solvent and 10 parts by weight of oxethylated nonylphenol as emulsifier.

e) Water-dispersible granules are obtained by mixing
  75 parts by weight of a compound of the formula (I) and/or salts thereof,
  10 parts by weight of calcium lignosulfonate,
  5 parts by weight of sodium lauryl sulfate,
  3 parts by weight of polyvinyl alcohol and
  7 parts by weight of kaolin,
  grinding on a pin mill and granulating the powder in a fluidized bed by spraying on water as granulation liquid.

f) Water-dispersible granules are also obtained by homogenizing and precomminuting
  25 parts by weight of a compound of the formula (I) and/or salts thereof,
  5 parts by weight of sodium 2,2'-dinaphthylmethane-6,6'-disulfonate,
  2 parts by weight of sodium oleoylmethyltaurate,
  1 part by weight of polyvinyl alcohol,
  17 parts by weight of calcium carbonate and
  50 parts by weight of water on a colloid mill, then grinding on a bead mill and atomizing and drying the suspension obtained in this way in a spray tower by means of a one-component nozzle.

C. Biological Examples

Description of the Experiment

1. Pre-Emergence Herbicidal Effect and Crop Plant Compatibility

Seeds of monocotyledonous or dicotyledonous weed plants or crop plants are planted in wood-fiber pots in sandy loam and covered with earth. The compounds according to the invention, formulated in the form of wettable powders (WP) or as emulsion concentrates (EC), are then applied as aqueous suspension or emulsion at a water application rate of 600 to 800 l/ha (converted) with the addition of 0.2% of wetting agent to the surface of the covering earth. The dosage of the compounds according to the invention is given in grams per hectare.

Following the treatment, the pots are placed in a greenhouse and kept under good growth conditions for the test plants. The visual scoring of the damage on the test plants is carried out after an experiment time of 3 weeks in comparison with untreated controls (herbicidal effect in percent (%): 100% effect=plants have died, 0% effect=as control plants).

The following abbreviations are used in the tables below:

| ABUTH: | *Abutilon theophrasti* | ALOMY: | *Alopecurus myosuroides* |
|---|---|---|---|
| AMARE: | *Amaranthus retroflexus* | AVEFA: | *Avena fatua* |
| CYPES: | *Cyperus esculentus* | ECHCG: | *Echinochloa crus-galli* |
| LOLMU: | *Lolium multiflorum* | MATIN: | *Matricaria inodora* |
| POLCO: | *Polygonum convolvulus* | SETVI: | *Setaria viridis* |
| STEME: | *Stellaria media* | VERPE: | *Veronica persica* |
| VIOTR: | *Viola tricolor* | | |

TABLE 1

Pre-emergence herbicidal effect

| Example No. | Dosage | ABUTH | ALOMY | AMARE | AVEFA | CYPES | ECHCG | LOLMU | MATIN | POLCO | SETVI | STEME | VERPE | VIOTR |
|---|---|---|---|---|---|---|---|---|---|---|---|---|---|---|
| 1.17 | 320 | 100 | 100 | 100 | 90 | 90 | 100 | 100 | 100 | | 100 | 100 | 100 | |
| 1.18 | 320 | 100 | 100 | 100 | 90 | 80 | 100 | 100 | 100 | | 100 | 100 | 100 | |
| 1.25 | 320 | | 100 | 100 | | 100 | 100 | 100 | 100 | | 100 | 100 | 100 | 90 |
| 1.26 | 320 | 80 | 100 | 100 | 90 | | 100 | 100 | 100 | 90 | 100 | 100 | 100 | 100 |
| 1.30 | 320 | | 100 | 100 | 100 | | 100 | 100 | 100 | 100 | 100 | 100 | 100 | 100 |
| 1.35 | 320 | 100 | 100 | 100 | 100 | 100 | 100 | 100 | 100 | 100 | 100 | 100 | 100 | 100 |
| 1.37 | 320 | | | 100 | | | 100 | 100 | 90 | | | 100 | 100 | |
| 1.46 | 320 | 80 | 80 | 100 | | | 90 | 100 | 100 | | 100 | 100 | 100 | 100 |
| 1.46 | 320 | 100 | 80 | 100 | 80 | | 100 | 100 | 100 | 100 | 100 | 100 | 100 | 100 |
| 1.51 | 320 | | | | | | | 100 | 100 | | | 100 | 100 | |
| 1.56 | 320 | | 100 | 100 | 100 | 80 | 100 | 100 | 100 | 95 | 100 | 100 | 100 | 100 |
| 1.61 | 320 | | 100 | 100 | 90 | | 100 | | 90 | 100 | 90 | 100 | 100 | 100 |
| 1.62 | 320 | | 80 | | | | 100 | 80 | 90 | | 90 | 100 | 100 | 100 |
| 1.63 | 320 | | 100 | 90 | 80 | | 100 | | 100 | 100 | 100 | 100 | 100 | 100 |
| 1.67 | 320 | 90 | 95 | 100 | 80 | | 100 | 95 | 100 | 100 | 100 | 100 | 100 | 100 |
| 1.75 | 320 | | 100 | 100 | 90 | | 100 | 95 | 100 | 100 | 95 | 100 | 100 | 100 |
| 1.76 | 320 | | | 90 | | | | | 100 | | | 100 | 100 | |
| 1.94 | 320 | | 80 | 90 | 80 | | 90 | 80 | 85 | 80 | 90 | 100 | 100 | 100 |
| 1.96 | 320 | | 100 | 100 | 80 | | 100 | 100 | 100 | 100 | 100 | 100 | 100 | 100 |
| 1.97 | 320 | | 80 | 100 | | | 100 | 100 | 100 | | 100 | 100 | 100 | 100 |
| 1.98 | 320 | | | 80 | | 100 | | | 80 | | 80 | 100 | 100 | 100 |
| 1.105 | 320 | 100 | 100 | 100 | 80 | 100 | 100 | 100 | 100 | 100 | 100 | 100 | 100 | 100 |
| 1.106 | 320 | | 100 | 100 | | | 90 | 100 | 90 | | 100 | 100 | 100 | |
| 1.120 | 320 | | 100 | 100 | 80 | | 100 | 90 | 100 | 100 | 100 | 100 | 100 | 100 |
| 1.121 | 320 | | 80 | 100 | | | 100 | 90 | 100 | 100 | 100 | 100 | 100 | 100 |
| 1.123 | 320 | | | 100 | | | 80 | | 100 | | | 100 | 100 | 100 |
| 1.124 | 320 | | | 100 | | | | | 90 | 90 | 80 | 100 | 100 | 100 |
| 1.125 | 320 | | 80 | 90 | | | 90 | | 95 | 90 | 90 | 100 | 100 | 100 |
| 1.126 | 320 | | | 100 | | | 95 | | 100 | 90 | 85 | 100 | 100 | 100 |
| 1.129 | 320 | 80 | 100 | 100 | 90 | 80 | 100 | 100 | 100 | 100 | 100 | 100 | 100 | 100 |

As the results show, the compounds according to the invention have a good herbicidal pre-emergence effectiveness in respect of a broad spectrum of weed grasses and weeds. For example, the compounds in table 1 have very good herbicidal effect in respect of harmful plants such as *Avena fatua, Stellaria media, Echinochloa crus-galli, Lolium multiflorum, Setaria viridis, Abutilon theophrasti, Amaranthus retroflexus* and *Alopecurus myosuroides* in the pre-emergence method at an application rate of 0.32 kg and less active substance per hectare. The compounds according to the invention are therefore suitable in the pre-emergence method for controlling undesired plant growth.

2. Post-Emergence Herbicidal Effect and Crop Plant Compatibility

Seeds of monocotyledonous or dicotyledonous weed plants or crop plants are planted in wood-fiber pots in sandy loam, covered with earth and grown in a greenhouse under good growth conditions. 2 to 3 weeks after sowing, the test plants are treated in the one-leaf stage. The compounds according to the invention, formulated in the form of wettable powders (WP) or as emulsion concentrates (EC), are then sprayed onto the green plant parts as aqueous suspension or emulsion at a water application rate of 600 to 800 l/ha (converted) with the addition of 0.2% of wetting agent. The dosage of the compounds according to the invention is given in grams per hectare.

After ca. 3 weeks' standing time of the test plants in the greenhouse under optimum growth conditions, the effect of the preparations is scored visually in comparison with untreated controls (herbicidal effect in percent (%): 100% effect=plants have died, 0% effect=as control plants).

TABLE 2

Post-emergence herbicidal effect

| Example No. | Dosage | ABUTH | ALOMY | AMARE | AVEFA | ECHCG | LOLMU | MATIN | PHBPU | POLCO | SETVI | STEME | VERPE | VIOTR |
|---|---|---|---|---|---|---|---|---|---|---|---|---|---|---|
| 1.17 | 320 | 87 | 90 | 97 | 80 | 93 | 93 | 85 | 90 | 80 | 90 | 97 | 87 | 90 |
| 1.18 | 320 | 85 | 85 | 85 | | 87 | 87 | 80 | 80 | | 90 | 93 | 83 | 85 |
| 1.23 | 320 | 80 | | 80 | | 100 | 90 | | 80 | 100 | 90 | 90 | 90 | 90 |
| 1.24 | 320 | | | | | 90 | 100 | 80 | | | | 100 | 90 | |
| 1.25 | 320 | | 90 | 90 | | 90 | 95 | | | | | 100 | 95 | |
| 1.26 | 320 | 80 | 85 | 85 | | 90 | 90 | 80 | 90 | 80 | | 90 | 95 | 85 |
| 1.28 | 320 | 90 | | 90 | | 90 | | | | 90 | | | 90 | 90 |
| 1.30 | 320 | | 95 | 93 | 100 | 100 | 100 | 80 | | 80 | 95 | 80 | 90 | |
| 1.35 | 320 | 95 | 100 | 93 | 95 | 100 | 90 | 85 | 90 | 90 | 95 | 95 | 95 | 90 |
| 1.37 | 320 | 85 | | 100 | | 80 | | | 80 | | | 95 | 90 | 80 |
| 1.46 | 320 | 100 | | 100 | | | | | | | 90 | 90 | 90 | 90 |
| 1.56 | 320 | | 85 | 80 | 80 | 90 | 93 | | 90 | | 80 | 80 | 90 | |
| 1.61 | 320 | 80 | | | | 90 | | | | | | 90 | 90 | 80 |
| 1.62 | 320 | | 80 | | | 90 | 90 | | 80 | 80 | | 80 | 80 | |
| 1.63 | 320 | | | | | 80 | | | | | 80 | 80 | 80 | |
| 1.67 | 320 | 90 | 85 | 90 | | 95 | 87 | 80 | 93 | 85 | 87 | 90 | 85 | 80 |
| 1.75 | 320 | | | 90 | | 85 | | | 90 | 80 | | 87 | 85 | |
| 1.96 | 320 | 85 | 80 | 85 | | 85 | 90 | | 90 | 85 | 85 | 95 | 85 | 85 |
| 1.97 | 320 | | | 80 | | 80 | 80 | | | | 80 | 80 | 80 | |
| 1.105 | 320 | 90 | 80 | 90 | 90 | 100 | 90 | 90 | 90 | 80 | 90 | 90 | | 80 |
| 1.106 | 320 | | 80 | 80 | | 90 | 90 | | | | 80 | 80 | 80 | |
| 1.120 | 320 | 90 | | 90 | | 100 | | 80 | 100 | 80 | 85 | 85 | 90 | 90 |
| 1.126 | 320 | | | | | 80 | | | 80 | | | 90 | 85 | |
| 1.129 | 320 | 90 | 90 | 90 | 80 | 100 | 90 | | | 90 | 90 | 90 | 90 | 80 |

As the results show, compounds according to the invention have good herbicidal post-emergence effectiveness in respect of a broad spectrum of weed grasses and weeds. For example, the compounds in table 2 have a very good herbicidal effect towards harmful plants such as *Avena fatua, Stellaria media, Echinochloa crus-galli, Lolium multiflorum, Setaria viridis, Abutilon theophrasti, Amaranthus retroflexus* and *Alopecurus myosuroides* in the post-emergence method at an application rate of 0.32 kg and less active substance per hectare. The compounds according to the invention are therefore suitable in the post-emergence method for controlling undesired plant growth.

The invention claimed is:

1. A herbicidal compound of formula (I) and/or an agrochemically compatible salt thereof

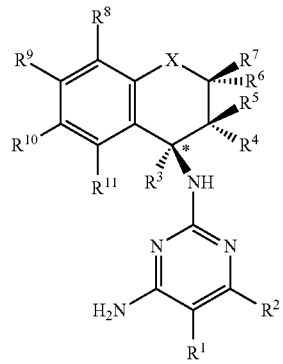

In which
$R^1$ is selected from the group consisting of halogen, hydroxy, cyano, nitro, amino, C(O)OH, C(O)NH$_2$;

($C_1$-$C_6$)-alkyl, ($C_1$-$C_6$)-haloalkyl, ($C_1$-$C_6$)-alkylcarbonyl, ($C_1$-$C_6$)-haloalkylcarbonyl, ($C_1$-$C_6$)-alkylcarbonyloxy, ($C_1$-$C_6$)-haloalkylcarbonyloxy, ($C_1$-$C_6$)-alkylcarbonyl-($C_1$-$C_4$)-alkyl;

($C_1$-$C_6$)-alkoxy, ($C_1$-$C_6$)-haloalkoxy, ($C_1$-$C_6$)-alkoxycarbonyl, ($C_1$-$C_6$)-haloalkoxycarbonyl, ($C_1$-$C_6$)-alkoxycarbonyl-($C_1$-$C_6$)-alkyl, ($C_1$-$C_6$)-haloalkoxycarbonyl-($C_1$-$C_6$)-alkyl, ($C_1$-$C_6$)-alkoxycarbonyl-($C_1$-$C_6$)-haloalkyl, ($C_1$-$C_6$)-haloalkoxycarbonyl-($C_1$-$C_6$)-haloalkyl;

($C_2$-$C_6$)-alkenyl, ($C_2$-$C_6$)-haloalkenyl, ($C_2$-$C_6$)-alkenylcarbonyl, ($C_2$-$C_6$)-haloalkenylcarbonyl, ($C_2$-$C_6$)-alkenyloxy, ($C_2$-$C_6$)-haloalkenyloxy, ($C_2$-$C_6$)-alkenyloxycarbonyl, ($C_2$-$C_6$)-haloalkenyloxycarbonyl;

($C_2$-$C_6$)-alkynyl, ($C_2$-$C_6$)-haloalkynyl, ($C_2$-$C_6$)-alkynylcarbonyl, ($C_2$-$C_6$)-haloalkynylcarbonyl, ($C_2$-$C_6$)-alkynyloxy, ($C_2$-$C_6$)-haloalkynyloxy, ($C_2$-$C_6$)-alkynyloxycarbonyl, ($C_2$-$C_6$)-haloalkynyloxycarbonyl;

tri($C_1$-$C_6$)-alkylsilyl-($C_2$-$C_6$)-alkynyl, di($C_1$-$C_6$)-alkylsilyl-($C_2$-$C_6$)-alkynyl, mono($C_1$-$C_6$)-alkylsilyl-($C_2$-$C_6$)-alkynyl; phenylsilyl-($C_2$-$C_6$)-alkynyl;

($C_6$-$C_{14}$)-aryl, ($C_6$-$C_{14}$)-aryloxy, ($C_6$-$C_{14}$)-arylcarbonyl and ($C_6$-$C_{14}$)-aryloxycarbonyl, which may in each case be substituted on the aryl moiety by halogen, ($C_1$-$C_6$)-alkyl and/or ($C_1$-$C_6$)-haloalkyl;

($C_6$-$C_{14}$)-aryl-($C_1$-$C_6$)-alkyl, ($C_6$-$C_{14}$)-aryl-($C_1$-$C_6$)-alkoxy, ($C_6$-$C_{14}$)-aryl-($C_1$-$C_6$)-alkylcarbonyl, ($C_6$-$C_{14}$)-aryl-($C_1$-$C_6$)-alkylcarbonyloxy, ($C_6$-$C_{14}$)-aryl-($C_1$-$C_6$)-alkoxycarbonyl, ($C_6$-$C_{14}$)-aryl-($C_1$-$C_6$)-alkoxycarbonyloxy;

mono(($C_1$-$C_6$)-alkyl)amino, mono(($C_1$-$C_6$)-haloalkyl)amino, di(($C_1$-$C_6$)-alkyl)amino, di(($C_1$-$C_6$)-haloalkyl)amino, (($C_1$-$C_6$)-alkyl-($C_1$-$C_6$)-haloalkyl)amino, N—(($C_1$-$C_6$)-alkanoyl)amino, N—(($C_1$-$C_6$)-haloalkanoyl)amino, aminocarbonyl-($C_1$-$C_6$)-alkyl, di($C_1$-$C_6$)-alkylaminocarbonyl-($C_1$-$C_6$)-alkyl;

mono(($C_1$-$C_6$)-alkyl)aminocarbonyl, mono(($C_1$-$C_6$)-haloalkyl)aminocarbonyl, di(($C_1$-$C_6$)-alkyl)aminocarbonyl, di(($C_1$-$C_6$)-haloalkyl)aminocarbonyl, (($C_1$-$C_6$)-alkyl-($C_1$-$C_6$)-haloalkyl)aminocarbonyl, N—(($C_1$-$C_6$)-alkanoyl)aminocarbonyl, N—(($C_1$-$C_6$)-haloalkanoyl)aminocarbonyl, mono(($C_6$-$C_{14}$)-aryl)aminocarbonyl, di(($C_6$-$C_{14}$)-aryl)aminocarbonyl, ($C_1$-$C_6$)-alkoxy-($C_1$-$C_6$)-alkyl, ($C_1$-$C_6$)-alkoxy-($C_1$-$C_6$)-alkoxy, ($C_1$-$C_6$)-alkoxycarbonyl-($C_1$-$C_6$)-alkoxy;

($C_3$-$C_8$)-cycloalkyl, which may be optionally substituted on the cycloalkyl radical by ($C_1$-$C_6$)-alkyl and/or halogen; ($C_3$-$C_8$)-cycloalkoxy, ($C_3$-$C_8$)-cycloalkyl-($C_1$-$C_6$)-alkyl, ($C_3$-$C_8$)-cycloalkyl-($C_1$-$C_6$)-haloalkyl, ($C_3$-$C_8$)-cycloalkyl-($C_1$-$C_6$)-alkoxy, ($C_3$-$C_8$)-cycloalkyl-($C_1$-$C_6$)-haloalkoxy, ($C_3$-$C_8$)-cycloalkylcarbonyl, ($C_3$-$C_8$)-cycloalkoxycarbonyl, ($C_3$-$C_8$)-cycloalkyl-($C_1$-$C_6$)-alkylcarbonyl, ($C_3$-$C_8$)-cycloalkyl-($C_1$-$C_6$)-haloalkylcarbonyl, ($C_3$-$C_8$)-cycloalkyl-($C_1$-$C_6$)-alkoxycarbonyl, ($C_3$-$C_8$)-cycloalkyl-($C_1$-$C_6$)-haloalkoxycarbonyl, ($C_3$-$C_8$)-cycloalkylcarbonyloxy, ($C_3$-$C_8$)-cycloalkoxycarbonyloxy, ($C_3$-$C_8$)-cycloalkyl-($C_1$-$C_6$)-alkylcarbonyloxy, ($C_3$-$C_8$)-cycloalkyl-($C_1$-$C_6$)-haloalkylcarbonyloxy, ($C_3$-$C_8$)-cycloalkyl-($C_1$-$C_6$)-alkoxycarbonyloxy, ($C_3$-$C_8$)-cycloalkyl-($C_1$-$C_6$)-haloalkoxycarbonyloxy;

($C_3$-$C_8$)-cycloalkenyl, ($C_3$-$C_8$)-cycloalkenyloxy, ($C_3$-$C_8$)-cycloalkenyl-($C_1$-$C_6$)-alkyl, ($C_3$-$C_8$)-cycloalkenyl-($C_1$-$C_6$)-haloalkyl, ($C_3$-$C_8$)-cycloalkenyl-($C_1$-$C_6$)-alkoxy, ($C_3$-$C_8$)-cycloalkenyl-($C_1$-$C_6$)-haloalkoxy, ($C_3$-$C_8$)-cycloalkenylcarbonyl, ($C_3$-$C_8$)-cycloalkenyloxycarbonyl, ($C_3$-$C_8$)-cycloalkenyl-($C_1$-$C_6$)-alkylcarbonyl, ($C_3$-$C_8$)-cycloalkenyl-($C_1$-$C_6$)-haloalkylcarbonyl, ($C_3$-$C_8$)-cycloalkenyl-($C_1$-$C_6$)-alkoxycarbonyl, ($C_3$-$C_8$)-cycloalkenyl-($C_1$-$C_6$)-haloalkoxycarbonyl, ($C_3$-$C_8$)-cycloalkenylcarbonyloxy, ($C_3$-$C_8$)-cycloalkenyloxycarbonyloxy, ($C_3$-$C_8$)-cycloalkenyl-($C_1$-$C_6$)-alkylcarbonyloxy, ($C_3$-$C_8$)-cycloalkenyl-($C_1$-$C_6$)-haloalkylcarbonyloxy, ($C_3$-$C_8$)-cycloalkenyl-($C_1$-$C_6$)-alkoxycarbonyloxy, ($C_3$-$C_8$)-cycloalkenyl-($C_1$-$C_6$)-haloalkoxycarbonyloxy;

hydroxy-($C_1$-$C_6$)-alkyl, hydroxy-($C_1$-$C_6$)-alkoxy, cyano-($C_1$-$C_6$)-alkoxy, cyano-($C_1$-$C_6$)-alkyl;

($C_1$-$C_6$)-alkylsulfonyl, ($C_1$-$C_6$)-alkylthio, ($C_1$-$C_6$)-alkylsulfinyl, ($C_1$-$C_6$)-haloalkylsulfonyl, ($C_1$-$C_6$)-haloalkylthio, ($C_1$-$C_6$)-haloalkylsulfinyl, ($C_1$-$C_6$)-alkylsulfonyl-($C_1$-$C_6$)-alkyl, ($C_1$-$C_6$)-alkylthio-($C_1$-$C_6$)-alkyl, ($C_1$-$C_6$)-alkylsulfinyl-($C_1$-$C_6$)-alkyl, ($C_1$-$C_6$)-haloalkylsulfonyl-($C_1$-$C_6$)-alkyl, ($C_1$-$C_6$)-haloalkylthio-($C_1$-$C_6$)-alkyl, ($C_1$-$C_6$)-haloalkylsulfinyl-($C_1$-$C_6$)-alkyl, ($C_1$-$C_6$)-alkylsulfonyl-($C_1$-$C_6$)-haloalkyl, ($C_1$-$C_6$)-alkylthio-($C_1$-$C_6$)-haloalkyl, ($C_1$-$C_6$)-alkylsulfinyl-($C_1$-$C_6$)-haloalkyl, ($C_1$-$C_6$)-haloalkylsulfonyl-($C_1$-$C_6$)-haloalkyl, ($C_1$-$C_6$)-haloalkylthio-($C_1$-$C_6$)-haloalkyl, ($C_1$-$C_6$)-haloalkylsulfinyl-($C_1$-$C_6$)-haloalkyl, ($C_1$-$C_6$)-alkylsulfonyloxy, ($C_1$-$C_6$)-haloalkylsulfonyloxy, ($C_1$-$C_6$)-alkylthiocarbonyl, ($C_1$-$C_6$)-haloalkylthiocarbonyl, ($C_1$-$C_6$)-alkylthiocarbonyloxy, ($C_1$-$C_6$)-haloalkylthiocarbonyloxy, ($C_1$-$C_6$)-alkylthio-($C_1$-$C_6$)-alkyl, ($C_1$-$C_6$)-alkylthio-($C_1$-$C_6$)-alkoxy, ($C_1$-$C_6$)-alkylthio-($C_1$-$C_6$)-alkylcarbonyl, ($C_1$-$C_6$) alkylthio-($C_1$-$C_6$)-alkylcarbonyloxy, ($C_4$-$C_{14}$)-arylsulfonyl, ($C_6$-$C_{14}$)-arylthio, ($C_6$-$C_{14}$)-arylsulfinyl, ($C_3$-$C_8$)-cycloalkylthio, ($C_3$-$C_8$)-alkenylthio, ($C_3$-$C_8$)-cycloalkenylthio, and ($C_3$-$C_6$)-alkynylthio;

$R^2$ is selected from the group consisting of hydrogen, halogen, hydroxy, cyano, nitro, amino, C(O)OH, C(O)NH$_2$;

($C_1$-$C_6$)-alkyl, ($C_1$-$C_6$)-haloalkyl, ($C_1$-$C_6$)-alkylcarbonyl, ($C_1$-$C_6$)-haloalkylcarbonyl, ($C_1$-$C_6$)-alkylcarbonyloxy, ($C_1$-$C_6$)-haloalkylcarbonyloxy, ($C_1$-$C_6$)-alkylcarbonyl-($C_1$-$C_4$)-alkyl;

($C_1$-$C_6$)-alkoxy, ($C_1$-$C_6$)-haloalkoxy, ($C_1$-$C_6$)-alkoxycarbonyl, haloalkoxycarbonyl, ($C_1$-$C_6$)-alkoxycarbonyl-($C_1$-$C_6$)-alkyl, ($C_1$-$C_6$)-haloalkoxycarbonyl-($C_1$-$C_6$)-alkyl, ($C_1$-$C_6$)-alkoxycarbonyl-($C_1$-$C_6$)-haloalkyl, ($C_1$-$C_6$)-haloalkoxycarbonyl-($C_1$-$C_6$)-haloalkyl;

($C_2$-$C_6$)-alkenyl, ($C_2$-$C_6$)-haloalkenyl, ($C_2$-$C_6$)-alkenylcarbonyl, ($C_2$-$C_6$)-haloalkenylcarbonyl, ($C_2$-$C_6$)-alkenyloxy, ($C_2$-$C_6$)-haloalkenyloxy, ($C_2$-$C_6$)-alkenyloxycarbonyl, ($C_2$-$C_6$)-haloalkenyloxycarbonyl;

($C_2$-$C_6$)-alkynyl, ($C_2$-$C_6$)-haloalkynyl, ($C_2$-$C_6$)-alkynylcarbonyl, ($C_2$-$C_6$)-haloalkynylcarbonyl, ($C_2$-$C_6$)-alkynyloxy, ($C_2$-$C_6$)-haloalkynyloxy, ($C_2$-$C_6$)-alkynyloxycarbonyl, ($C_2$-$C_6$)-haloalkynyloxycarbonyl;

tri($C_1$-$C_6$)-alkylsilyl-($C_2$-$C_6$)-alkynyl, di($C_1$-$C_6$)-alkylsilyl-($C_2$-$C_6$)-alkynyl, mono($C_1$-$C_6$)-alkylsilyl-($C_2$-$C_6$)-alkynyl; phenylsilyl-($C_7$-$C_6$)-alkynyl;

($C_6$-$C_{14}$)-aryl, ($C_6$-$C_{14}$)-aryloxy, ($C_6$-$C_{14}$)-arylcarbonyl and ($C_6$-$C_{14}$)-aryloxycarbonyl, which may in each case be substituted on the aryl moiety by halogen, ($C_1$-$C_6$)-alkyl and/or ($C_1$-$C_6$)-haloalkyl;

($C_6$-$C_{14}$)-aryl-($C_1$-$C_6$)-alkyl, ($C_6$-$C_{14}$)-aryl-($C_1$-$C_6$)-alkoxy, ($C_6$-$C_{14}$)-aryl-($C_1$-$C_6$)-alkylcarbonyl, ($C_6$-$C_{14}$)-aryl-($C_1$-$C_6$)-alkylcarbonyloxy, ($C_6$-$C_{14}$)-aryl-($C_1$-$C_6$)-alkoxycarbonyl, ($C_6$-$C_{14}$)-aryl-($C_1$-$C_6$)-alkoxycarbonyloxy;

mono(($C_1$-$C_6$)-alkyl)amino, mono(($C_1$-$C_6$)-haloalkyl)amino, di(($C_1$-$C_6$)-alkyl)amino, di(($C_1$-$C_6$)-haloalkyl)amino, (($C_1$-$C_6$)-alkyl-($C_1$-$C_6$)-haloalkyl)amino, N—(($C_1$-$C_6$)-alkanoyl)amino, N—(($C_1$-$C_6$)-halo alkanoyl)amino, aminocarbonyl-($C_1$-$C_6$)-alkyl, di($C_1$-$C_6$)-alkylaminocarbonyl-($C_1$-$C_6$)-alkyl;

mono(($C_1$-$C_6$)-alkyl)aminocarbonyl, mono(($C_1$-$C_6$)-haloalkyl)aminocarbonyl, di(($C_1$-$C_6$)-alkyl)aminocarbonyl, di(($C_1$-$C_6$)-haloalkyl)aminocarbonyl, (($C_1$-$C_6$)-alkyl-($C_1$-$C_6$)-haloalkyl)aminocarbonyl, N—(($C_1$-$C_6$)-alkanoyl)aminocarbonyl, N—(($C_1$-$C_6$)-haloalkanoyl)aminocarbonyl, mono(($C_6$-$C_{14}$)-aryl)aminocarbonyl, di(($C_6$-$C_{14}$)-aryl)aminocarbonyl, $(C_1-C_6)$-alkoxy-$(C_1-C_6)$-alkyl, $(C_1-C_6)$-alkoxy-$(C_1-C_6)$-alkoxy, $(C_1-C_6)$-alkoxycarbonyl-$(C_1-C_6)$-alkoxy;

$(C_3-C_8)$-cycloalkyl, which may be optionally substituted on the cycloalkyl radical by $(C_1-C_6)$-alkyl and/or halogen; $(C_3-C_8)$-cycloalkoxy, $(C_3-C_8)$-cycloalkyl-$(C_1-C_6)$-alkyl, $(C_3-C_8)$-cycloalkyl-$(C_1-C_6)$-haloalkyl, $(C_3-C_8)$-cycloalkyl-$(C_1-C_6)$-alkoxy, $(C_3-C_8)$-cycloalkyl-$(C_1-C_6)$-haloalkoxy, $(C_3-C_8)$-cycloalkylcarbonyl, $(C_3-C_8)$-cycloalkoxycarbonyl, $(C_3-C_8)$-cycloalkyl-$(C_1-C_6)$-alkylcarbonyl, $(C_3-C_8)$-cycloalkyl-$(C_1-C_6)$-haloalkylcarbonyl, $(C_3-C_8)$-cycloalkyl-$(C_1-C_6)$-alkoxycarbonyl, $(C_3-C_8)$-cycloalkyl-$(C_1-C_6)$-haloalkoxycarbonyl, $(C_3-C_8)$-cycloalkylcarbonyloxy, $(C_3-C_8)$-cycloalkoxycarbonyloxy, $(C_3-C_8)$-cycloalkyl-$(C_1-C_6)$-alkylcarbonyloxy, $(C_3-C_8)$-cycloalkyl-$(C_1-C_6)$-haloalkylcarbonyloxy, $(C_1-C_8)$-cycloalkyl-$(C_1-C_6)$-alkoxycarbonyloxy, $(C_3-C_8)$-cycloalkyl-$(C_1-C_6)$-haloalkoxycarbonyloxy;

$(C_3-C_8)$-cycloalkenyl, $(C_3-C_8)$-cycloalkenyloxy, $(C_3-C_8)$-cycloalkenyl-$(C_1-C_6)$-alkyl, $(C_3-C_8)$-cycloalkenyl-$(C_1-C_6)$-haloalkyl, $(C_3-C_8)$-cycloalkenyl-$(C_1-C_6)$-alkoxy, $(C_3-C_8)$-cycloalkenyl-$(C_1-C_6)$-haloalkoxy, $(C_3-C_8)$-cycloalkenylcarbonyl, $(C_3-C_8)$-cycloalkenyloxycarbonyl, $(C_3-C_8)$-cycloalkenyl-$(C_1-C_6)$-alkylcarbonyl, $(C_3-C_8)$-cycloalkenyl-$(C_1-C_6)$-haloalkylcarbonyl, $(C_3-C_8)$-cycloalkenyl-$(C_1-C_6)$-alkoxycarbonyl, $(C_3-C_8)$-cycloalkenyl-$(C_1-C_6)$-haloalkoxycarbonyl, $(C_3-C_8)$-cycloalkenylcarbonyloxy, $(C_3-C_8)$-cycloalkenyloxycarbonyloxy, $(C_3-C_8)$-cycloalkenyl-$(C_1-C_6)$-alkylcarbonyloxy, $(C_3-C_8)$-cycloalkenyl-$(C_1-C_6)$-haloalkylcarbonyloxy, $(C_3-C_8)$-cycloalkenyl-$(C_1-C_6)$-alkoxycarbonyloxy, $(C_3-C_8)$-cycloalkenyl-$(C_1-C_6)$-haloalkoxycarbonyloxy;

hydroxy-$(C_1-C_6)$-alkyl, hydroxy-$(C_1-C_6)$-alkoxy, cyano-$(C_1-C_6)$-alkoxy, cyano-$(C_1-C_6)$-alkyl;

$(C_1-C_6)$-alkylsulfonyl, $(C_1-C_6)$-alkylthio, $(C_1-C_6)$-alkylsulfinyl, $(C_1-C_6)$-haloalkylsulfonyl, $(C_1-C_6)$-haloalkylthio, $(C_1-C_6)$-haloalkylsulfinyl, $(C_1-C_6)$-alkylsulfonyl-$(C_1-C_6)$-alkyl, $(C_1-C_6)$-alkythio-$(C_1-C_6)$-alkyl, $(C_1-C_6)$-alkylsulfinyl-$(C_1-C_6)$-alkyl, $(C_1-C_6)$-haloalkylsulfonyl-$(C_1-C_6)$-alkyl, $(C_1-C_6)$-haloalkylthio-$(C_1-C_6)$-alkyl, $(C_1-C_6)$-haloalkylsulfinyl-$(C_1-C_6)$-alkyl, $(C_1-C_6)$-alkylsulfonyl-$(C_1-C_6)$-haloalkyl, $(C_1-C_6)$-alkylthio-$(C_1-C_6)$-haloalkyl, $(C_1-C_6)$-alkylsulfinyl-$(C_1-C_6)$-haloalkyl, $(C_1-C_6)$-haloalkylsulfonyl-$(C_1-C_6)$-haloalkyl, $(C_1-C_6)$-haloalkylthio-$(C_1-C_6)$-haloalkyl, $(C_1-C_6)$-haloalkylsulfinyl-$(C_1-C_6)$-haloalkyl, $(C_1-C_6)$-alkylsulfonyloxy, $(C_1-C_6)$-haloalkylsulfonyloxy, $(C_1-C_6)$-alkylthiocarbonyl, $(C_1-C_6)$-haloalkylthiocarbonyl, $(C_1-C_6)$-alkylthiocarbonyloxy, $(C_1-C_6)$-haloalkylthiocarbonyloxy, $(C_1-C_6)$-alkylthio-$(C_1-C_6)$-alkyl, $(C_1-C_6)$-alkylthio-$(C_1-C_6)$-alkoxy, $(C_1-C_6)$-alkylthio-$(C_1-C_6)$-alkylcarbonyl, $(C_1-C_6)$-alkylthio-$(C_1-C_6)$-alkylcarbonyloxy, $(C_4-C_{14})$-arylsulfonyl, $(C_6-C_{14})$-arylthio, $(C_6-C_{14})$-arylsulfinyl, $(C_3-C_8)$-cycloalkylthio, $(C_3-C_8)$-alkenylthio, $(C_3-C_8)$-cycloalkenylthio, and $(C_1-C_6)$-alkynylthio;

Or the radicals $R^1$ and $R^2$ together may form a $(C_2-C_6)$-alkylene group, which may comprise one or more oxygen and/or sulfur atoms, where the $(C_2-C_6)$-alkylene group may be mono- or polysubstituted by halogen and the respective halogen substituents may be identical or different; and $R^3$ is selected from the group consisting of hydrogen, $(C_1-C_6)$-alkyl and $(C_1-C_6)$-haloalkyl;

$R^4$ and $R^5$ in each case independently of one another are selected from the group consisting of hydrogen, $(C_1-C_6)$-alkyl, $(C_1-C_6)$-haloalkyl, hydroxy, $(C_1-C_6)$-alkoxy and $(C_1-C_6)$-haloalkoxy; or the radicals $R^4$ and $R^5$, together with the carbon atom to which they are bonded, may form a three- to seven-membered ring;

$R^6$ and $R^7$ in each case independently of one another are selected from the group consisting of hydrogen, $(C_1-C_6)$-alkyl, $(C_1-C_6)$-haloalkyl, $(C_1-C_6)$-alkoxy, $(C_1-C_6)$-haloalkoxy, $(C_6-C_{14})$-aryl, $(C_6-C_{14})$-aryloxy, $(C_6-C_{14})$-arylcarbonyl and $(C_6-C_{14})$-aryloxycarbonyl; or the radicals $R^6$ and $R^7$ together may form a $(C_2-C_7)$-alkylene group, which may comprise one or more oxygen and/or sulfur atoms, where the $(C_2-C_7)$-alkylene group may be mono- or polysubstituted by halogen and the respective halogen substituents may be identical or different, $R^8$, $R^9$, $R^{10}$ and $R^{11}$, independently of one another, are in each case selected from the group consisting of hydrogen, halogen, cyano, $(C_1-C_6)$-alkyl, $(C_1-C_6)$-alkylcarbonyl, $(C_1-C_6)$-alkyloxycarbonyl, $(C_1-C_6)$-alkylaminocarbonyl, $(C_1-C_6)$-dialkylaminocarbonyl, $(C_1-C_6)$-haloalkyl, $(C_1-C_6)$-alkoxy, $(C_1-C_6)$-haloalkoxy, $(C_2-C_6)$-alkynyl, $(C_2-C_6)$-haloalkynyl, $(C_2-C_6)$-alkynylcarbonyl, $(C_2-C_6)$-haloalkynylcarbonyl, $(C_2-C_6)$-alkynyloxy, $(C_2-C_6)$-haloalkynyloxy, $(C_2-C_6)$-alkynyloxycarbonyl and $(C_2-C_6)$-haloalkynyloxycarbonyl and nitro;

X is selected from the group consisting of a chemical bond, $CH_2$, O, S, carbonyl, NH, $CR^{12}R^{13}$, and $NR^{14}$;

$R^{12}$ and $R^{13}$ in each case independently of one another are selected from the group consisting of hydrogen, $(C_1-C_6)$-alkyl and $(C_1-C_6)$-haloalkyl;

$R^{14}$ is selected from the group consisting of hydrogen, $(C_1-C_6)$-alkyl, and $(C_1-C_6)$-haloalkyl; and wherein the stereochemical configuration on the carbon atom indicated by (*) is (R).

2. A herbicidal compound of the formula (I) as claimed in claim 1, wherein the radical X is selected from the group consisting of $CH_2$, O and a chemical bond.

3. A herbicidal compound of the formula (I) as claimed in claim 1, wherein the radical $R^1$ is selected from the group consisting of halogen, cyano, $C(=O)NH_2$, $NO_2$, $(C_1-C_6)$-alkyl, $(C_1-C_6)$-haloalkyl, $(C_3-C_6)$-cyclopropyl, $(C_1-C_6)$-alkoxy, $(C_1-C_6)$-thioalkyl, $(C_1-C_6)$-alkylthio, $(C_2-C_6)$-alkynyl, mono$(C_1-C_6)$-alkylamino, di$(C_1-C_6)$-alkylamino and tri $(C_1-C_6)$-alkylsilyl-$(C_2-C_6)$-alkynyl.

4. A herbicidal compound of the formula (I) as claimed in claim 1, wherein the radical $R^2$ is selected from the group consisting of hydrogen, halogen, $(C_1-C_6)$-alkylphenyl; $(C_6-C_{14})$-aryl, which may be substituted on the aryl radical by $(C_1-C_6)$-alkyl, $(C_6-C_{14})$-haloalkyl and/or halogen; $C_6$-aryl-$(C_1-C_6)$-haloalkyl, $(C_1-C_6)$-alkyl, $(C_1-C_6)$-haloalkyl, $(C_1-C_6)$-alkoxy, $(C_1-C_6)$-alkoxy-$(C_1-C_6)$-alkyl; $(C_3-C_6)$-cycloalkyl, which may be substituted on the cycloalkyl radical by $(C_1-C_6)$-alkyl, $(C_6-C_{14})$-haloaryl and/or halogen; 1-$(C_1-C_6)$-alkylcyclopropyl, 1-(($C_1-C_6$)-alkyl-$C_6$-aryl)cyclopropyl, 1-(monohalophenyl)cyclopropyl, 1-(dihalophenyl)cyclopropyl, mono $(C_1-C_6)$-alkylamino, di$(C_1-C_6)$-alkylamino, $(C_1-C_6)$-thioalkyl, $(C_1-C_6)$-alkylthio, $(C_1-C_6)$-alkoxy and amino.

5. A herbicidal compound of the formula (I) as claimed in claim 1, wherein the radicals $R^1$ and $R^2$, together with the carbon atoms to which they are bonded, form a five- or six-membered ring, which may be interrupted by one or two heteroatoms selected from the group consisting of oxygen and sulfur.

6. A herbicidal compound of the formula (I) as claimed in claim 1, wherein the radical $R^3$ is hydrogen or $(C_1-C_6)$-alkyl.

7. A herbicidal compound of the formula (I) as claimed in claim 1, wherein the radicals $R^4$ and $R^5$, in each case independently of one another, are selected from the group consisting of hydrogen, $(C_1-C_6)$-alkyl, hydroxy, cyclopropyl and $(C_1-C_6)$-alkoxy.

8. A herbicidal compound of the formula (I) as claimed in claim 1, wherein the radicals $R^4$ and $R^5$, together with the carbon atom to which they are bonded, form a three- to seven-membered ring.

9. A herbicidal compound of the formula (I) as claimed in claim 1, wherein the radicals $R^6$ and $R^7$, independently of one another, are selected from the group consisting of hydrogen, $(C_1-C_6)$-alkyl and $(C_6-C_{14})$-aryl.

10. A herbicidal compound of the formula (I) as claimed in claim 1, wherein the radical $R^8$ is selected from the group consisting of hydrogen, $(C_1-C_6)$-alkyl and halogen.

11. A herbicidal compound of the formula (I) as claimed in claim 1, wherein the radical $R^9$ is selected from the group consisting of hydrogen and $(C_1-C_6)$-alkyl.

12. A herbicidal compound of the formula (I) as claimed in claim 1, wherein the radical $R^{10}$ is selected from the group consisting of hydrogen, $(C_1-C_6)$-alkyl, di$(C_1-C_6)$-alkylamino, halogen, $(C_2-C_6)$-alkenyl, $(C_2-C_6)$-alkynyl, $(C_1-C_6)$-alkyl-$(C_2-C_6)$-alkynyl, $(C_1-C_6)$-alkoxy-$(C_1-C_6)$-alkyl-$(C_2-C_6)$-alkynyl, cyano, $(C_1-C_6)$-alkoxycarbonyl and aminocarbonyl.

13. A herbicidal compound of the formula (I) as claimed in claim 1, wherein the radical $R^{11}$ is selected from the group consisting of hydrogen and $(C_1-C_6)$-alkyl.

14. A process for the preparation of a herbicidal compound of formula (I)

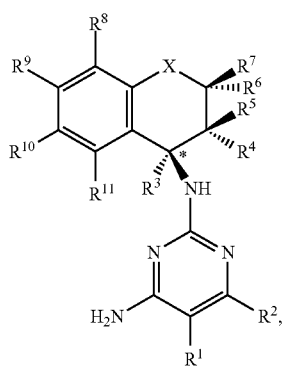

and/or salt thereof according to claim 1, which comprises
(1) reacting a compound of formula (II)

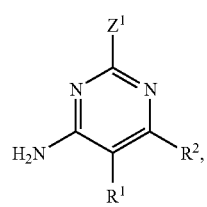

wherein $Z^1$ is an exchangeable radical or a leaving group, with an amine of formula (III) or an acid addition salt thereof

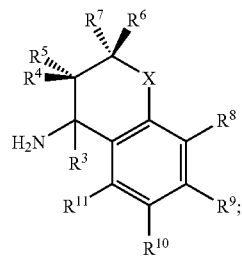

(2) reacting a derivative of formula (I) where $R^1$, $R^2$ or $R^{10}$=halogen, with acetylene or trimethylsilyl-protected acetylene with transition metal catalysis, in a protic or aprotic solvent and the addition of a base at a temperature from 20 to 150° C. to give a compound of formula (I) where $R^1$, $R^2$ or $R^{10}$=alkynyl;

(3) saponifying a derivative of formula (I) where $R^1$=CN with acidic or basic catalysis and converting carboxylic acids obtained into acid chlorides and, converting into amides;

(4) converting a derivative of formula (I) where $R^2$=halogen in a protic or aprotic solvent and addition of a base at a temperature from 100 to 200° C. through reaction with an alcoholate or amine to give a compound of formula (I) where $R^2$=alkoxyalkyl or aminoalkyl or diaminoalkyl.

15. A herbicidal or plant growth regulating composition, which comprises one or more herbicidal compounds of the formula (I) or salts thereof as claimed in claim 1.

16. A method for controlling harmful plants or for regulating the growth of plants, which comprises applying an effective amount of one or more herbicidal compounds of the formula (I) or salts thereof as claimed in claim 1 to plants, plant parts, plant seeds and/or to an area under cultivation.

17. A herbicidal compound of the formula (I) as claimed in claim 2, wherein the radical $R^1$ is selected from the group consisting of halogen, cyano, C(=O)NH$_2$, NO$_2$, $(C_1-C_6)$-alkyl, $(C_1-C_6)$-haloalkyl, $(C_3-C_6)$-cyclopropyl, $(C_1-C_6)$-alkoxy, $(C_1-C_6)$-thioalkyl, $(C_1-C_6)$-alkylthio, $(C_2-C_6)$-alkynyl, mono$(C_1-C_6)$-alkylamino, di$(C_1-C_6)$-alkylamino and tri $(C_1-C_6)$-alkylsilyl-$(C_2-C_6)$-alkynyl.

18. A herbicidal compound of the formula (I) as claimed in claim 2, wherein the radical $R^2$ is selected from the group consisting of hydrogen, halogen, $(C_1-C_6)$-alkylphenyl; $(C_6-C_{14})$-aryl, which may be substituted on the aryl radical by $(C_1-C_6)$-alkyl, $(C_6-C_{14})$-haloalkyl and/or halogen; $C_6$-aryl-$(C_1-C_6)$-haloalkyl, $(C_1-C_6)$-alkyl, $(C_1-C_6)$-haloalkyl, $(C_1-C_6)$-alkoxy, $(C_1-C_6)$-alkoxy-$(C_1-C_6)$-alkyl; $(C_3-C_6)$-cycloalkyl, which may be substituted on the cycloalkyl radical by $(C_1-C_6)$-alkyl, $(C_6-C_{14})$-haloaryl and/or halogen; 1-$(C_1-C_6)$-alkylcyclopropyl, 1-(($C_1-C_6$)-alkyl-$C_6$-aryl)cyclopropyl, 1-(monohalophenyl)cyclopropyl, 1-(dihalophenyl)cyclopropyl, mono $(C_1-C_6)$-alkylamino, di$(C_1-C_6)$-alkylamino, $(C_1-C_6)$-thioalkyl, $(C_1-C_6)$-alkylthio, $(C_1-C_6)$-alkoxy and amino.

19. A herbicidal compound of the formula (I) as claimed in claim 2, wherein the radicals $R^1$ and $R^2$, together with the carbon atoms to which they are bonded, form a five- or six-membered ring, which may be interrupted by one or two heteroatoms selected from the group consisting of oxygen and sulfur.

20. A herbicidal compound of the formula (I) as claimed in claim 2, wherein the radical $R^3$ is hydrogen or $(C_1-C_6)$-alkyl.

21. A herbicidal compound according to claim 1, selected from the group consisting of
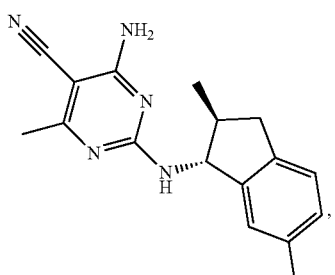
(compound 120)
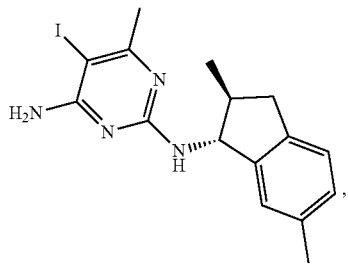
(compound 17)
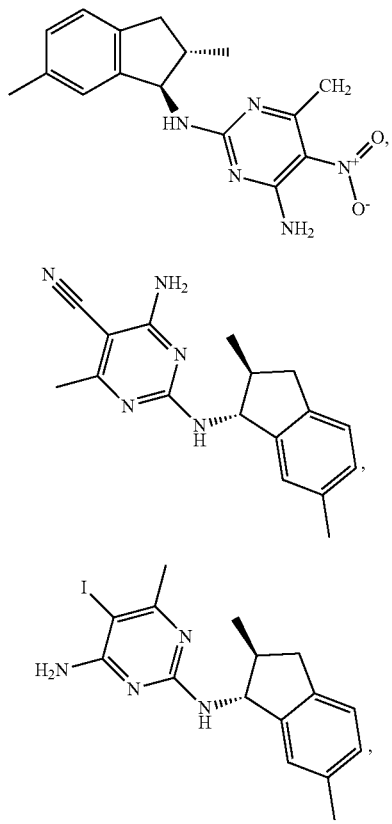
(compound 46)
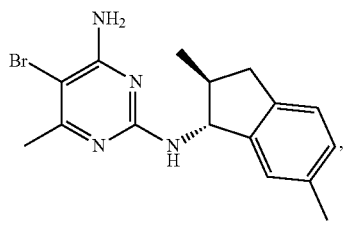
(compound 110)
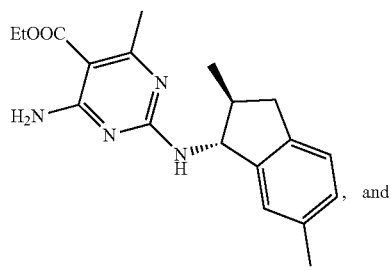
(compound 59)
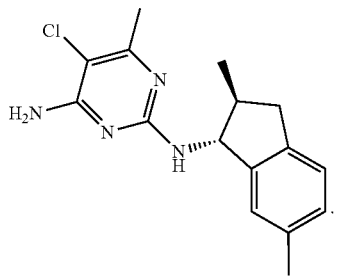
\* \* \* \* \*